US012673064B2

(12) United States Patent
Birkett et al.

(10) Patent No.: US 12,673,064 B2
(45) Date of Patent: Jul. 7, 2026

(54) BIODEGRADABLE DRUG-POLYMER CONJUGATE

(71) Applicant: POLYACTIVA PTY LTD, Melbourne (AU)

(72) Inventors: Stephen Lonsdale Birkett, Langwarrin (AU); Andrew Craig Donohue, Bentleigh East (AU); Asha Marina D'Souza, Carnegie (AU); Sarah Man Yee Ng, Berwick (AU); Adrian Sulistio, Glen Iris (AU); Russell John Tait, Balwyn (AU); David Valade, Glenroy (AU); Alan Naylor, Royston (GB); Jason Watling, Cheltenham (AU); Carmen Vittoria Scullino, Moonee Ponds (AU)

(73) Assignee: POLYACTIVA PTY LTD, Melbourne (AU)

( * ) Notice: Subject to any disclaimer, the term of this patent is extended or adjusted under 35 U.S.C. 154(b) by 1082 days.

(21) Appl. No.: 17/762,021

(22) PCT Filed: Sep. 19, 2019

(86) PCT No.: PCT/AU2019/051003

§ 371 (c)(1),
(2) Date: Mar. 18, 2022

(87) PCT Pub. No.: WO2021/051149

PCT Pub. Date: Mar. 25, 2021

(65) Prior Publication Data

US 2022/0401455 A1 Dec. 22, 2022

(51) Int. Cl.

*A61K 31/558* (2006.01)
*A61K 9/00* (2006.01)

(Continued)

(52) U.S. Cl.

CPC .......... *A61K 31/558* (2013.01); *A61K 31/559* (2013.01); *A61K 47/542* (2017.08); *A61K 47/545* (2017.08); *A61K 47/60* (2017.08)

(58) Field of Classification Search

None

See application file for complete search history.

(56) References Cited

U.S. PATENT DOCUMENTS

2012/0122964 A1 5/2012 Kambe et al.
2013/0310438 A1 11/2013 Maruyama et al.

(Continued)

FOREIGN PATENT DOCUMENTS

WO WO-2014/134689 A1 9/2014
WO WO-2018/165710 A1 9/2018
WO WO-2018/165711 A1 9/2018

OTHER PUBLICATIONS

Ogawa et al. "Discovery of G Protein-Biased EP2 Receptor Agonists" ACS Medicinal Chemistry Letters, vol. 7, pp. 306-311 (2016).

(Continued)

*Primary Examiner* — Ha S Nguyen

(74) *Attorney, Agent, or Firm* — Foley & Lardner LLP

(57) ABSTRACT

A drug-polymer conjugate, which is a copolymer of at least one monomer of formula (I) where: X may be the same or different at each occurrence and represents a terminal functional group comprising an alkyne or an azide; Q is independently selected at each occurrence and may be present or absent and when present, represents a linking group; R is selected from the group consisting of linear or branched hydrocarbon, optionally substituted aryl and optionally substituted heteroaryl; D is a releasable bicyclic prostaglandin; L is a linker group; and at least one co-monomer of Formula III J-$(Y^1\text{-}A)_n$, J represents a linking functional group, n is 2 to 8 preferably 3 to 8; $Y^1$ comprises a polyether of formula $(OR^a)_m$ wherein $R^a$ is independently ethylene, propylene and (Continued)

butylene and m is from 1 to 300 (preferably 2 to 300) and the polyether is in chain with one or more groups which are preferably selected from one or more of optionally substituted straight or branched $C_1$ to $C_{10}$ alkylene, amino, ether, ester, amide, carbonate and carbamate; A may be the same or different at each occurrence and represents a group comprising a terminal functional group comprising an alkyne or an azide functionality, wherein said terminal functional group is complementary to the terminal functional group X of formula (I) providing triazole moieties from reaction of X and A.

26 Claims, 2 Drawing Sheets

(51) Int. Cl.

| | |
|---|---|
| ***A61K 31/559*** | (2006.01) |
| ***A61K 47/54*** | (2017.01) |
| ***A61K 47/59*** | (2017.01) |
| ***A61K 47/60*** | (2017.01) |
| ***A61K 47/69*** | (2017.01) |
| ***A61P 27/06*** | (2006.01) |
| ***C08G 73/08*** | (2006.01) |

(56) References Cited

U.S. PATENT DOCUMENTS

| | | | |
|---|---|---|---|
| 2013/0324577 | A1 | 12/2013 | Kambe et al. |
| 2017/0182173 | A1 | 6/2017 | Ng et al. |

OTHER PUBLICATIONS

Sugimoto et al., "Discovery of Novel Seven-Membered Prostacyclin Analogues as Potent and Selective Prostaglandin FP and EP3 Dual Agonists," ACS Medicinal Chemistry Letters, vol. 8, pp. 107-112 (2007).

Yamane et al., "IOP-Lowering Effect of ONO-9054, A Novel Dual Agonist of Prostanoid EP3 and FP Receptors, in Monkeys," vol. 56, No. 4, pp. 2547-2552 (2015).

BIODEGRADABLE DRUG-POLYMER CONJUGATE

CROSS-REFERENCE TO RELATED APPLICATIONS

The present application is the U.S. National Stage of International Application No. PCT/AU2019/051003, filed Sep. 19, 2019.

FIELD

The invention relates to a drug-polymer conjugate, to a drug-monomer conjugate for use in preparation thereof and to an implant containing the drug-polymer conjugate.

BACKGROUND

Polymer-drug conjugates containing a drug covalently bound to a polymer are of interest for the targeted and controlled delivery of therapeutic agents. In the treatment of many different conditions, the site-specific delivery of a drug directly to or near a desired site of action in the body of a subject can be highly desirable to improve the efficacy and/or safety of the drug. Certain sites in a subject may require sophisticated delivery vehicles to overcome barriers for effective drug delivery. For example, the eye has a limited volume for administration and requires a pharmaceutical product with a high drug loading to ensure that adequate doses of drug can be delivered while keeping product volume to a minimum. Despite the limited volume it is desirable to be able to deliver drug to the site continuously and in a controlled manner over an extended period of time. Administration to the target site generally involves injection of the product. Consequently it is both an advantage and desirable for the product to biodegrade and disappear at the target site after treatment is provided, obviating the need for removal at the end of therapy. Such removal typically requires surgical intervention.

Prostaglandin (PG) analogues are very effective at reducing intraocular pressure (IOP) in a variety of animals and in humans with relatively few side effects. The mechanisms of action of several PG-analogues, their prodrugs and analogues have been studied in rabbits, cats, monkeys and humans. The most common PG-analogues marketed around the world to reduce intraocular pressure and treat glaucoma are latanoprost, bimatoprost and travoprost, all PGF2 alpha agonists. PGF2 alpha agonists have been shown to lower intraocular pressure by means of an increase in uveoscleral outflow. Another class of PG-analogues are the EP receptor agonists. EP receptor agonists have been shown to lower intraocular pressure by a different mechanism that involves an increase in trabecular network outflow. The selective EP4 receptor agonist 3,7-dithia-PGE1 reduced IOP and total outflow resistance in monkeys without affecting uveoscleral outflow or aqueous flow. Omidenepag isopropyl (DE-117, Santen Pharmaceuticals) is an EP2 receptor agonist that has completed phase 2a trials, where it was shown that a 0.002% dosage proved more effective than latanoprost 0.005% at week 1 and provided similar reduction in IOP to latanoprost through week 4. More recently, PG-analogues with a dual mechanism of action have been developed. For example, Ono Pharmaceutical Co. Ltd., Japan developed Sepetaprost (marketed by Santen) a dual PGF2 alpha and EP3 agonist that lowers intraocular pressure by means of increased uveoscleral outflow and trabecular outflow.

Prostaglandins are a family of molecules designed to bind to a prostaglandin receptor and are used to treat gastrointestinal acid related disorders such as duodenal and gastric ulcers, as abortifacients or uterotonics to induce labour or prevent past partum haemorrhage, and to treat ocular hypertension. ProstaglandinProstaglandins exert an ocular hypotensive effect by increasing uveoscleral outflow of aqueous humour.

Prostaglandins are used in the treatment of glaucoma are presently formulated as eye drops, which if administered conscientiously to the affected eye will lower intraocular pressure. This in turn can slow the progression of glaucoma. The prostaglandins are administered as eye drops, either alone (i.e. as a single agent) or in combination. In some cases the prostaglandins and administered in combination with β-blockers that exert their effect through a different mechanism and may provide an additive effect in reducing intraocular pressure. For example, some pharmaceutical preparations used in the treatment of glaucoma, such as Xalacom™ eye drops marketed by Pfizer and Ganfort™ eye drops marketed by Allergan, contain a prostaglandin in combination with a β-blocker.

Unfortunately, as glaucoma is an asymptomatic disease many patients do not use their drops conscientiously, compromising therapy. A recent study by Friedman et al. (Friedman et al. IOVS 2007:48, 5052-5057) showed that adherence to glaucoma treatment options is poor with only 59% of patients in possession of an ocular hypotensive agent at 12 months, and only 10% of patients used such medication continuously. Patient compliance in glaucoma therapy is therefore an issue.

Unfortunately, as ocular surgery is more prevalent in the elderly many patients do not have the drop competence to administer their drops effectively, compromising therapy. A recent study by An et al showed that drop competence in the elderly is poor with only 7.4% of patients capable of administering their drops effectively following cataract surgery (An J A, Kasner O, Samek D A, Levesque V. *Evaluation of eye drop administration by inexperienced patient after cataract surgery*. J Cataract Refract Surg. 2014; 40:1857-1861). Drop competence in post-surgical drop therapy is therefore an issue.

Drug delivery systems have been developed to aid in the administration and/or sustained delivery of agents (such as drugs) to a desired site of action. One mode of delivering a drug to a subject involves the use of a polymer in association with the drug so that it can be delivered to and/or retained at a specific location.

One form of a polymer/drug delivery system utilises an admixture of a polymer with a drug, where the drug is blended with the polymer matrix. However, such admixtures generally result in poor control over the release of the drug, with a "burst effect" often occurring immediately after administration and significant changes in the physical properties of the admixture occurring as the drug is released (Sjoquist, B.; Basu, S.; Byding, P.; Bergh, K.; Stjernschantz, J. Drug Metab. Dispos. 1998, 26, 745). In addition, such admixtures have limited dose loading capacity, resulting in a prohibitively large device for convenient administration to some sites in a subject.

Another form of a polymer/drug delivery system is based on the polymerisation of a drug so as to incorporate the drug molecule as part of the backbone of a polymer chain. Such a system is described in U.S. Pat. No. 6,613,807, WO2008/128193, WO94/04593 and U.S. Pat. No. 7,122,615. However, such polymer systems generally provide inefficient delivery of the drug, as release of the drug relies on breakdown of the polymer backbone. Furthermore, breakdown of the polymer backbone produces inactive intermediates. Such intermediates can complicate regulatory approval, which may require the safety of the intermediates to be demonstrated.

Another approach for preparing polymer-drug conjugates involves the covalent attachment of drug molecules to a pre-formed polymer backbone. Examples of such polymer conjugates have been reviewed in Nature Reviews: Drug Discovery 2003:2, 347-360. However, this approach can also be problematic. In particular, steric and thermodynamic constraints can affect the amount of drug that can be covalently attached, and also impact on the distribution of the drug along the polymer backbone. These factors can, in turn, reduce control over the release of the drug. Furthermore, the use of a pre-formed polymer backbone provides limited scope for modification of the polymer conjugate after attachment of the drug, should the properties of the conjugate need to be adjusted to improve drug release and/or to aid patient comfort, particularly in the eye.

A further consideration with a polymer/drug delivery system is the safety and tolerability of the polymer system. Poor tolerability can come about from the chemistry of the polymer (e.g. acidic by-products with PLA or PLGA systems) or the physical properties of the polymer (e.g. non-biodegradable systems, hard materials with sharp edges). The polymer systems most commonly recognised as safe and well tolerated are the polyether class, such as polyethylene glycol, or polypropylene glycol. Such polymers are chemically inert, metabolically stable and produce soft, deformable materials. They also have low immunogenicity. All features that make them an excellent candidate for polymer/drug delivery systems. All such polymers are typically hydrophilic, which contributes to their good safety and tolerability also limits their use as a base polymer for a polymer/drug delivery system. Hydrophilic polymers, such as polyethers, provide little or no diffusivity barrier for control of drug release, particularly over longer periods of weeks or months. Furthermore, hydrophilic polymers are often water soluble so are rapidly cleared from the site. The chemical and metaboloic stability of polyethers is another barrier to their use in polymer/drug delivery systems. Such stable systems are cleared from the body intact, so need to be soluble in water to be cleared. Hydrogels have generally been found to be of limited use as drug delivery systems as there is still little or no diffusivity barrier to control rate of release of a drug.

It would be desirable to provide new polymer-drug conjugates, which address or ameliorate one or more disadvantages or shortcomings associated with existing materials and/or their method of manufacture, or to at least provide a useful alternative to such materials and their method of manufacture.

SUMMARY

In one aspect the invention provides a drug-polymer conjugate, which is a copolymer of at least one monomer of formula (I):

(I)

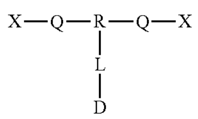

where:

X may be the same or different at each occurrence and represents a terminal functional group comprising an alkyne or an azide;

Q is independently selected at each occurrence and may be present or absent and when present, represents a linking group;

R is selected from the group consisting of linear or branched hydrocarbon, optionally substituted aryl and optionally substituted heteroaryl;

D is a releasable bicyclic prostaglandin;

L is a linker group;

and at least one co-monomer of Formula III $$J\text{-}(Y^1\text{-}A)_n \qquad \text{III}$$

J represents a linking functional group, n is 2 to 8, preferably 3 to 8;

$Y^1$ comprises a polyether of formula $(OR^a)_m$ wherein $R^a$ is independently ethylene, propylene and butylene and m is from 1 to 300 (preferably 2 to 300) and the polyether is in chain with one or more groups which are preferably selected from one or more of optionally substituted straight or branched $C_1$ to $C_{10}$ alkylene, amino, ether, ester, amide, carbonate and carbamate;

A may be the same or different at each occurrence and represents a group comprising a terminal functional group comprising an alkyne or an azide functionality, wherein said terminal functional group is complementary to the terminal functional group X of formula (I) providing triazole moieties from reaction of X and A.

The presence of at least 3 groups of three ($Y^1$-A) arranged about J provides a three dimensional network structure to the polymer. This network structure provides a solid polymeric scaffold for delivery of the active which can be moulded into suitable shapes for introduction to localised sites within the body so as to deliver the drug payload to the required site. The polymer conjugate may be adapted to remain at the site of the body to which it is introduced. Despite the solid nature of the polymer network the structure including the multi-arm cores of the network comprising oxyalkylene polymer segments $(OR^a)_m$ provides controlled release of the active agent over a period of time which may avoid the need for repeated administration of the active agent. The polymer backbone may be adapted to biodegrade. In this way the solid polymer-conjugate may be adapted to biodegrade to smaller segments after the desired treatment period to provide clearance of the polymer from the site of delivery.

The bicyclic prostaglandin may be of formula (X)

(X)

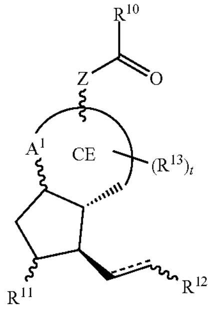

wherein:

CE is a 6 or 7 membered cyclic ether or cyclic thioether which may be saturated or include one double bond, the ring is typically closed by a chain 3 or 4 carbon atoms;

$A^1$ is oxygen or sulfur;

------ represents a double or single bond which is independently selected in each case;

$R^{12}$ is $C_{1-6}$ alkyl optionally substituted with 1 to 5 (preferably 1 to 3 substituents) selected from the group consisting of hydroxyl, oxo, halo, $C_{1-4}$ alkoxy, ring 2, —O-ring 2 and —S-ring 2 wherein ring 2 is selected from optionally substituted, aromatic or non-aromatic, carbocyclic and heterocyclic rings.

and one of $R^{10}$, $R^{11}$ and $R^{12}$ is linked to the polymer backbone and wherein:

$R^{11}$ and $R^{12}$ when linked to the polymer backbone comprise the alcohol residue of an ester or carbonate linking group and $R^{10}$ when linked to the polymer backbone forms the acid residue of an ester or anhydride linking group; and $R^{10}$ when not linked to the backbone is selected from the group consisting of —OH, —O($C_{1-6}$ alkyl), and —$NR^aR^b$ where $R^a$ and $R^b$ are each independently selected from the group consisting of H, $C_{1-6}$ alkyl and $C_{1-4}$ alkylsulfonyl; and the group —O—($C_{1-6}$ alkyl)-O—$NO_2$;

$R^{11}$ when not linked to the polymer backbone is hydroxyl or halo;

$R^{13}$ is selected from halo, $C_{1-4}$alkyl and $C_{1-4}$alkoxy and t is 0, 1 or 2; and Z is selected from the group consisting of;

—$(CH_2)_m$— wherein m is from 1 to 10 preferably 2 to 4;

—$(CH_2)_n$—CH═CH— wherein n is from 1 to 6, preferably 1 or 2;

—$(CH_2)_p$-$A^1$-$CH_2$— wherein $A^1$ is oxygen or sulfur and p is 1 to 4; and the group ring 1 selected from optionally substituted, aromatic or non-aromatic, carbocyclic and heterocyclic rings.

The drug-polymer conjugate of any one of the previous claims, wherein the bicyclic prostaglandin is of formula (Xa) or (Xb):

(Xa)

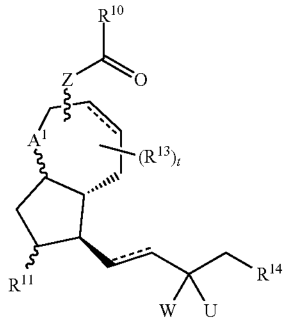

or

-continued (Xb)

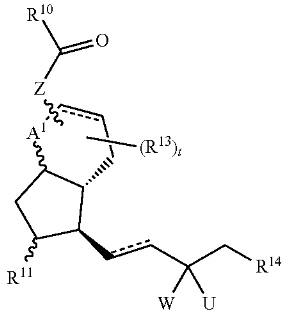

where:

$A^1$ is oxygen or sulfur;

------ represents a double or single bond which is independently selected in each case;

W and U are selected from the group consisting of where W and U together form oxo (═O), where W and U are each halo, and where W is $R^{15}$ and U is hydrogen;

$R^{14}$ is selected from the group consisting of $C_{1-6}$ alkyl, $C_{1-4}$ alkoxy, $C_{1-4}$ alkyl substituted by ring 2, $C_{1-4}$ alkoxy substituted by ring 2 and —O-ring 2 wherein ring 2 is selected from the group consisting of optionally substituted, aromatic or non-aromatic, carbocyclic and heterocyclic rings; and one of $R^{10}$, $R^{11}$ and $R^{15}$ is linked to the polymer backbone and wherein:

$R^{11}$ and $R^{15}$ when linked to the polymer backbone are the alcohol residue of an ester or carbonate linking group and $R^{10}$ when linked to the polymer backbone forms the acid residue of an ester or anhydride linking group; and $R^{10}$ when not linked to the backbone is selected from the group consisting of —OH, —O($C_{1-6}$ alkyl), and —$NR^aR^b$ where $R^a$ and $R^b$ are each independently selected from the group consisting of H, $C_{1-6}$ alkyl and $C_{1-4}$ alkylsulfonyl; and the group —O—($C_{1-6}$ alkyl)-O—$NO_2$;

$R^{11}$ when not linked to the polymer backbone is hydroxyl or halo;

when $R^{15}$ is not linked to the backbone then W is hydroxy and U is hydrogen, or W and U are each fluoro, or W and U together form oxo;

$R^{13}$ is selected from halo, $C_{1-4}$alkyl and $C_{1-4}$alkoxy and t is 0, 1 or 2; and Z is selected from the group consisting of;

—$(CH_2)_m$— wherein m is from 1 to 10 preferably 2 to 4;

—$(CH_2)_n$—CH═CH— wherein n is from 1 to 6, preferably 1 or 2;

—$(CH_2)_p$-$A^1$-$CH_2$— wherein $A^1$ is oxygen or sulfur and p is 1 to 4; and ring 1 selected from optionally substituted, aromatic or non-aromatic, carbocyclic and heterocyclic rings.

In a preferred aspect the bicyclic prostaglandin is of formula Xa-1;

(Xa-1)

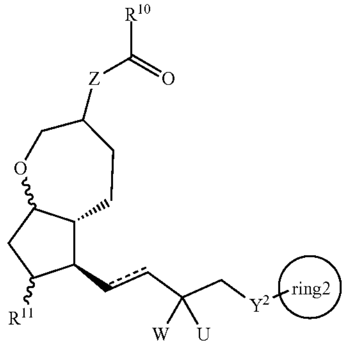

wherein

------ represents a double or single bond;

W and U are selected from the group consisting of where W and U together form oxo (=O), where W and U are each halo, and where W is $R^{15}$ and U is hydrogen;

one of $R^{10}$, $R^{11}$ and $R^{15}$ is linked to the polymer backbone and wherein:

$R^{11}$ and $R^{15}$ when linked to the polymer backbone are the alcohol residue of an ester or carbonate linking group and $R^{10}$ when linked to the polymer backbone forms the acid residue of an ester or anhydride linking group; and $R^{10}$ when not linked to the backbone is selected from the group consisting of —OH, —O($C_{1-6}$ alkyl), —$NR^aR^b$ where $R^a$ and $R^b$ are each independently selected from the group consisting of H, $C_{1-6}$ alkyl and the group $C_{1-4}$ alkylsulfonyl; and the group —O—($C_{1-6}$ alkyl)-O—$NO_2$;

$R^{11}$ when not linked to the polymer backbone is hydroxy or halo;

when $R^{15}$ is not linked to the backbone then W is hydroxy and U is hydrogen, or W and U are each fluoro, or W and U together form oxo;

$Y^2$ is selected from —$CH_2$—, oxygen and sulfur;

ring 2 is selected from optionally substituted, aromatic or non-aromatic carbocylic and heterocyclic rings; and Z is selected from the group consisting of;

—$(CH_2)_m$— wherein m is from 1 to 10 preferably 2 to 4;

—$(CH_2)_n$—CH=CH— wherein n is from 1 to 6, preferably 1 or 2;

—$(CH_2)_p$-$A^1$-$CH_2$— wherein $A^1$ is oxygen or sulfur and p is 1 to 4; and the group ring 1 selected from optionally substituted, aromatic or non-aromatic, carbocyclic and heterocyclic rings.

In a preferred embodiment $R^{10}$ is linked to the polymer backbone and forms an ester functional group with linker L.

In one set of embodiments the drug-polymer conjugate D is of formula Xa-2

(Xa-2)

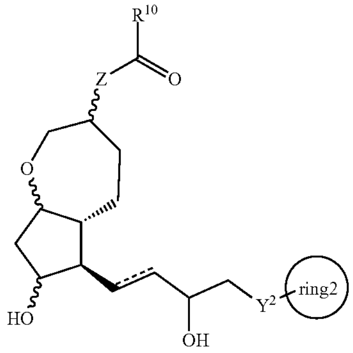

wherein $R^{10}$ is the bond to linker L and is —OH in the released bicyclic prostaglandin;

Z is selected from the group consisting of;

—$(CH_2)_m$— wherein m is from 1 to 10 preferably 2 to 4;

—$(CH_2)_n$—CH=CH— wherein n is from 1 to 6, preferably 1 or 2;

—$(CH_2)$p-A-CH2- wherein A is oxygen or sulfur; and the group ring 1 selected from optionally substituted, aromatic or non-aromatic, carbocyclic and heterocyclic rings;

------ represents a double or single bond;

$Y^2$ is selected from —$CH_2$—, oxygen or sulfur; and ring 2 is selected from optionally substituted, aromatic or non-aromatic, carbocyclic and heterocyclic rings.

In a further embodiment of formula Xb the dicyclic prostaglandin is of formula Xb-1 wherein the substituents are defined as for formula Xb (Xb-1)

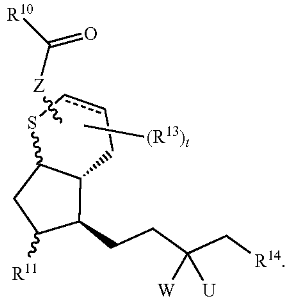

In a preferred embodiment $R^{10}$ is linked to the polymer backbone and forms an ester link with linker L thus providing a monomer of formula I having the formula Ia (Ia)

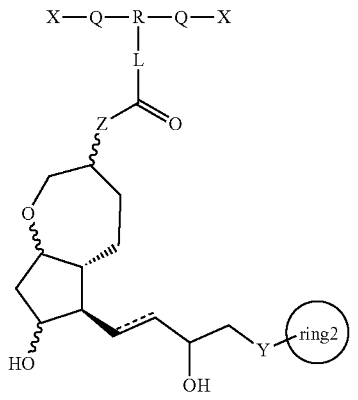

where L comprises oxygen forming the alcohol portion of an ester with the carboxylic acid portion of the bicyclic prostaglandin acid.

In one embodiment the drug-polymer conjugate comprises a polymer backbone with a plurality of biodegradable groups. Specific examples of the biodegradable groups are backbone segments of Formula (II):

(II)

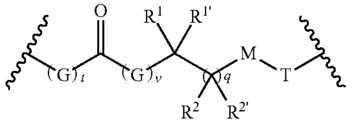

wherein

G are independently selected from oxygen and $NR^{16}$ where $R^{16}$ is hydrogen or $C_1$ to $C_4$ alkyl;

each of t and v are independently 0 or 1 and at least one of t and v is 1 (preferably one of t and v is 1 and the other is 0);

$R^1$, $R^{1'}$, $R^2$ and $R^{2'}$ are independently selected from the group consisting of hydrogen, alkyl, alkoxy and alkoxyalkyl, and wherein one of the pairs of $R^1$, $R^1$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and

T is a triazole moiety.

In one embodiment and at least one of $R^1$, $R^{1'}$, $R^2$ and $R^{2'}$ is not hydrogen. We have found that the presence of the substituents moderates biodegradation to allow controlled release over an extended period where prolonged treatment of for example over 15 days such as over 30 days or over 60 days is desirable.

The biodegradable group may be present as Q in the drug-monomer conjugate of formula (I), in the comonomer of as part of the group Y in formula (III) or in both the drug monomer and the comonomer.

Examples of the group Q which may be present in the drug monomer include groups of formula:

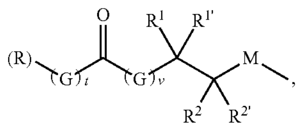

including groups of formula:

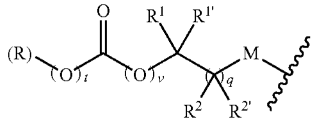

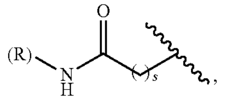

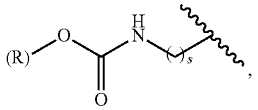

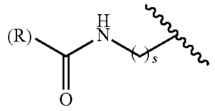

and

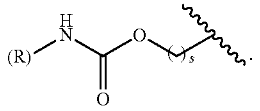

wherein

G are independently selected from oxygen and $NR^{16}$ where $R^{16}$ is hydrogen or $C_1$ to $C_4$ alkyl;

each of t and v are independently 0 or 1 and at least one of t and v is 1 (preferably one of t and v is 1 and the other is 0);

$R^1$, $R^{1'}$, $R^2$ and $R^{2'}$ are independently selected from the group consisting of hydrogen, alkyl, alkoxy and alkoxyalkyl, and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and

S is from 0 to 10, preferably 0 to 6.

More specific examples of Q may be selected from the group consisting of:

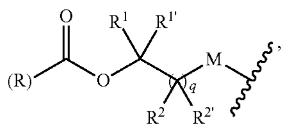

-continued

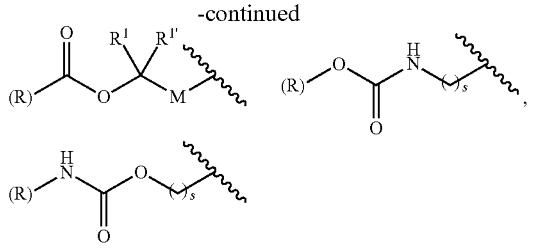

In one aspect the drug-polymer conjugate is a co-polymer of a drug-monomer conjugate of formula (I) is of formula (IV)

(IV)

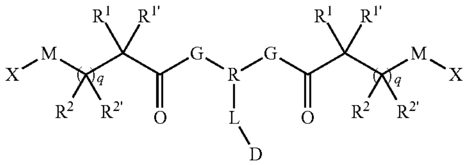

G are independently selected from oxygen and $NR^{16}$ where $R^{16}$ is hydrogen or $C_1$ to $C_4$ alkyl;

M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1;

X may be the same or different at each occurrence and is a terminal functional group comprising an alkyne or an azide;

R is selected from the group consisting of optionally substituted linear or branched hydrocarbon, optionally substituted aryl and optionally substituted heteroaryl;

L is a linker group; and

D is a releasable drug selected from bicyclic prostaglandins.

It will be understood by those skilled in the art that reaction of the alkyne group and azide provides a triazole link in the backbone of the polymer.

In one embodiment the monomer of formula (I) is of formula IVa (IVa)

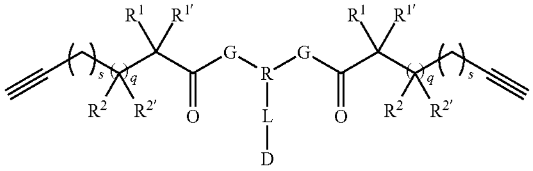

wherein R, $R^1$, $R^{1'}$, $R^2$, $R^{2'}$, R, G, L, D and q are as defined above and s is from 0 to 10 preferably 0 to 6 such as 0, 1, 2 or 3.

The drug-polymer conjugate of any one of claim 1 to 5, wherein the co-monomer of Formula III has the formula IIIa $$J\text{-}((OR^a)_m\text{—}B\text{-}A)_n \qquad \text{(IIIa)}$$

wherein

A may be the same or different at each occurrence and represents a group comprising a terminal functional group comprising an alkyne or an azide functionality, wherein the alkyne or azide functionality in the terminal functional group is complementary to the alkyne or azide functionality in a terminal functional group X present on a monomer of formula (I);

J represents a bond, oxygen or linking functional group, $R^a$ is selected from ethylene, propylene, butylene and mixtures thereof;

m is 1 to 300;

n is 3 to 8;

B is a bond, oxygen, the group of formula -MOC(O)N(H)M'-, -MOC(O)OM'-MC(O)NHM'-, the group formula selected from (VIa), (VIb), (VIc) and (VId):

(VIa)

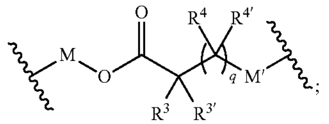

(VIb)

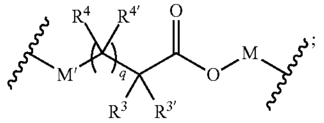

I (VIc)

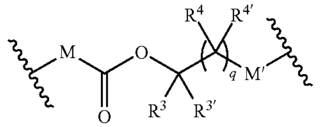

or (VId)

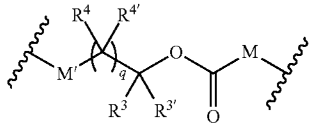

wherein M and M' are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and wherein in the monomers of formula, (VIa), (VIb), (VIc) and (VId) the groups R3, R3', R4 and R4' are independently selected from the group consisting of hydrogen, alkyl, alkoxy, alkoxy-alkyl, amino, alkyl amino, dialkylamino, amino-alkyl, alkylamino-alkyl, dialkylamino-alkyl wherein one of the pairs of $R^3$, $R^{3'}$, $R^4$, $R^{4'}$, may between the members of the pair form a carbocycle or heterocycle of 3 to 6 constituent ring members wherein the heterocycle may comprise from 1 to 3 constituent heteroatom ring members selected from oxygen and nitrogen which nitrogen may optionally be substituted by $C_1$ to $C_6$ alkyl.

The functional group B in formula IIIa in one embodiment is selected from the group consisting a bond, oxygen, the group of formula -MOC(O)N(H)M' and the group formula selected from (VIa) and (VIb).

In one aspect the conjugate is a copolymer of monomers of formula II and IIIa wherein at least one of $R^1$, $R^{1'}$, $R^2$, $R^{2'}$, $R^3$, $R^{3'}$, $R^4$ and $R^{4'}$ present in the monomers is not hydrogen. Without wishing to be bound by theory the presence of the substituents in a position alpha or beta to the ester (particularly alpha) is believed to moderate the susceptibility of the ester to hydrolysis and accordingly moderates biodegradation of the drug-polymer conjugate The drug-polymer conjugate in one set of embodiments comprises network branched segments of formula (XXX):

(XXX)

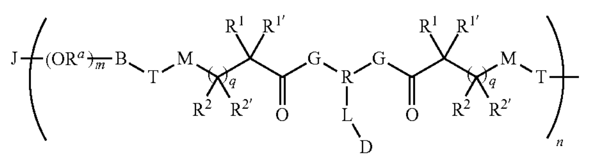

wherein n is 3 to 8 and is the number of branches of the bracketed group about J and the groups J, R, $R^a$, $R^1$, $R^{1'}$, $R^2$, $R^{2'}$, T, M, L, G and D and the integers m, q and n are as above defined and B is as defined for formula (IIIa).

The drug-polymer may contain a range of different groups R in the polymer backbone which are the group in the backbone to which the drug D is tethered via linking group L. The group R may in one set of embodiments be selected from the group consisting of straight and branched chain hydrocarbon of from 1 to 12 carbon atoms,

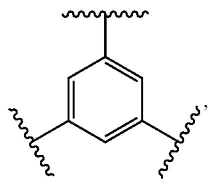
,
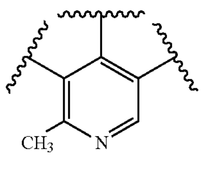
or

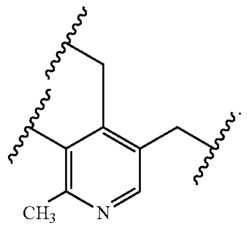
.

In one set of embodiments the drug-polymer conjugate is a co-polymer of a drug conjugate monomer of formula (IV)

(IV)

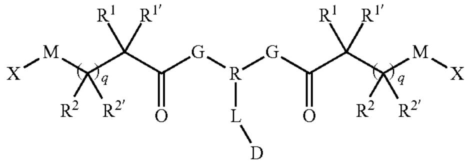

G is independently selected from oxygen and $NR^{16}$ where $R^{16}$ is hydrogen or $C_1$ to $C_4$ alkyl;

M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

X is a terminal functional group comprising an alkyne or an azide;

R is selected from the group consisting of optionally substituted linear or branched hydrocarbon, optionally substituted aryl and optionally substituted heteroaryl;

L is a linker group; and

D is a releasable drug selected from bicyclic prostaglandins;

and a co-monomer of Formula IIIa $$J\text{-}((OR^a)_m\text{—}B\text{-}A)_n \qquad \text{IIIa}$$

where:

A may be the same or different at each occurrence and represents a group comprising a terminal functional group comprising an alkyne or an azide functionality, wherein the alkyne or azide functionality in the terminal functional group is complementary to the alkyne or azide functionality in a terminal functional group X present on a monomer of formula (II);

J represents a linking functional group, preferably an optionally substituted hydrocarbon or hydrocarbon ether or polyether of from 2 to 4 hydrocarbon units; $R^a$ at each occurrence may be ethylene, propylene or butylene;

m is from 1 to 300;

n is from 3 to 8 (preferably 3 or 4);

B is a bond, oxygen, the group of formula -MOC(O)N(H)M'- or the group formula (VIa)

(VIa)

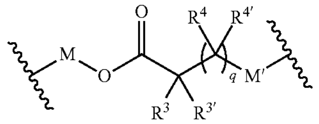

wherein

M and M' are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group $N(R^w)$ wherein $R^w$ is selected from hydrogen and $C_1$ to $C_4$ alkyl;

q is 0 or 1;

wherein in the monomers of formula (IV) and (111) the groups $R^1$, $R^{1'}$, $R^2$, $R^{2'}$, $R^3$, $R^{3'}$, $R^4$ and $R^{4'}$ are independently selected from the group consisting of hydrogen, alkyl, alkoxy, alkoxy-alkyl and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and one of the pairs of $R^3$, $R^{3'}$ and $R^4$, $R^{4'}$, may between the members of the pair form a carbocycle or heterocycle of 3 to 6 constituent ring members wherein the heterocycle may comprise from 1 to 3 constituent oxygen heteroatom ring members I.

Biodegradation of the polymer in vivo is controlled by the presence of substituents when at least one of $R^1$, $R^{1'}$, $R^2$, $R^{2'}$, $R^3$, $R^{3'}$, $R^4$ and $R^{4'}$ present in the monomers is not hydrogen and/or when the comonomer of formula (IIIa) is present and n is from 3 to 8 (preferably 3 or 4). This biodegradation chemistry introduced in the polymer backbone in formula (I) and (II) can be used to ensure the in-use life of the product is greater than the treatment period controlled by the pendant linker chemistry. Conversely, the backbone substitution and resultant biodegradation chemistry can be used to control the treatment period independently of the pendant linker chemistry by ensuring the rate of biodegradation is faster than the rate of drug release. Such a system ensures no loss of potency near the end of the in-use life of the product.

The invention further allows the product to maintain its integrity and have minimal loss of function during the treatment period, yet biodegrade and dissolve as soon as possible thereafter. Such a system may be used to provide a non-linear loss of mass with respect to time during its in-use lifetime with minimal mass loss attributable to the polymer backbone during the treatment period and rapid mass loss of the polymer backbone after the treatment period. A cross-linked or hyperbranched polymer architecture provided by co-monomer (IIIa) where n is 3 or more with biodegradation chemistry incorporated into the polymer architecture provides such a mass loss profile.

In the drug-polymer conjugates of the invention we have found that the polyether segments particularly in the network polymers (where n is 3 to 8) delivery would retains the hydrophilic, low immunogenic properties typical of such polyether, but the drug-polymer is rendered insoluble for the desired treatment period and is then able to biodegrade into soluble fragments thereafter.

Modification of the polyethers segments $(OR^a)_m$ into a network architecture provides a polymer conjugate that is insoluble in water but still generally sufficiently hydrophilic to form a hydrogel. The use of a multi-valent monomer component (III) in the reaction allows preparation of the insoluble polymer. By weight, such hydrogels are mostly liquid, yet they behave like solids due to a three-dimensional cross-linked network within the liquid. Covalent attachment the drug pendant to the polymer network chain of the hydrogel together with the chemistry of the linker provides a means for controlling the rate of drug release.

The combination of the linkage chemistry of the pendant drug to the polymer chain and the biodegradation chemistry incorporated into the polymer chain of the network provides a means to separately control the rate of drug release from the rate of biodegradation of the polymer. The treatment period of the product can then be determined by either the period of controlled drug release or the period its takes for the polymer to biodegrade, whichever comes sooner.

The modification of the branched polyether to introduce chemistry susceptible to hydrolysis (e.g. ester, amides, carbonates or carbamates) at points within the polymer chain facilitates polymer biodegradation. The introduction of such chemistry into any of the monomers used to produce a hydrogel may be used to provide efficient biodegradation of the hydrogel at the end of the treatment period.

The cross-linked hydrogel offers a further advantage by providing a non-linear loss of product mass compared with an equivalent linear polymer system. The underlying hydrolysis of a common biodegradation chemistry (e.g. ester) is the same, whether contained in a liner polymer or a cross-linked hydrogel. However, in the case of the hydrogel, the cross-linked architecture ensures no significant loss of product mass occurs until a critical proportion of all the biodegradation moieties within the polymer chain are cleaved. Rapid mass loss occurs once that critical level is achieved. Hence, the mass loss profile is non-linear with very little loss of mass until the critical proportion of cleavage occurs after which there is a rapid loss of mass. Such a system allows a product to be produced that has little or no mass loss during the treatment period and rapid mass loss after the treatment period.

DETAILED DESCRIPTION

Figure 1:
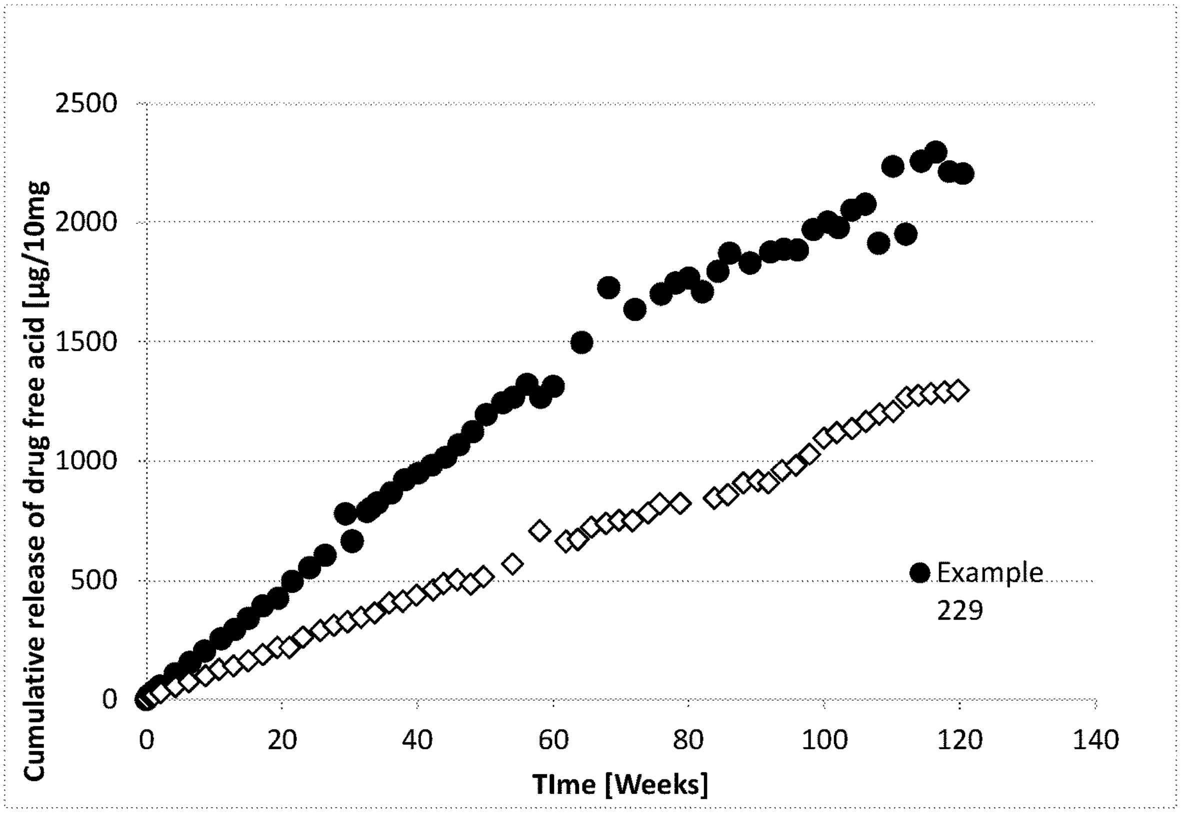
FIG. 1 is a graph having two plots showing the cumulative release (μg/10 mg) of drug free acid with time exposed to isotonic phosphate buffer (pH 7.4) at 37.0° C. from drug-polymer conjugates with a common linker (L), common co-monomer but a different Q-X moiety as described in Example 146.

The term "drug" refers to a substance for therapeutic use whose application (or one or more applications) involves: a chemical interaction, or physico-chemical interaction, with a subject's physiological system; or an action on an infectious agent, or on a toxin or other poison in a subject's body, or with biological material such as cells in vitro.

As used herein, the term "prodrug" refers to a derivative of the drug moiety, wherein the derivative may have little or none of the activity of the drug moiety per se yet is capable of being converted in vivo or in vitro into a drug moiety. An example of such derivatisation is the acetylation of one or more hydroxyl groups on a drug moiety, such that subsequent to being released in vivo the released prodrug is deacetylated to produce the drug moiety.

As used herein, the term "pharmaceutically acceptable salt" means those salts that are safe and effective for use in pharmaceutical preparations. Pharmaceutically acceptable salts include salts of acidic groups present in compounds of the invention. Suitable salts may include sodium, potassium, ammonium, calcium, diethylamine and piperazine salts and the like. Pharmaceutically acceptable salts are described in Stahl P H, Wermuth C G, editors. 2002. Handbook of pharmaceutical salts: Properties, selection and use. Weinheim/Zurich: Wiley-VCH/VHCA.

As used herein, it is contemplated that the term "bicyclic prostaglandin" includes, without limitation, natural bicyclic prostaglandins and bicyclic prostaglandin analogs. The bicyclic prostaglandins are generally present in the polymer-bicyclic prostaglandin conjugates and monomer bicyclic prostaglandin conjugates as the acid residue portion of an ester formed at the (D) end of the linker.

Polymers having drug s covalently attached thereto are sometimes referred to in the art as "polymer-drug conjugates". In some instances, it may be convenient to refer to a polymer-drug agent conjugate of the invention as a "drug-polymer conjugate", "drug-polymer conjugate", "drug-polymer conjugate", "polymer conjugate", "polymeric prodrug" or simply a "conjugate".

A hydrogel is a macromolecular polymer gel constructed of a network of cross-linked polymer chains. Hydrogels are synthesized hydrophilic monomers by either chain or step growth polymerisation, along with a functional crosslinker to promote network formation.

In one aspect, the present invention relates to a polymer-drug agent conjugate comprising a polymer backbone and a plurality of releasable drugs covalently bonded to and pendant from the polymer backbone. In accordance with this aspect, the polymer backbone comprises a plurality of triazole moieties.

Triazole moieties present in the polymer backbone of the polymer-drug conjugates, which are the product of an azide/alkyne coupling, are 1,2,3-triazole moieties.

1,2,3-Triazole moieties can be produced through the reaction of co-monomers having appropriate complementary terminal functional groups comprising alkyne and/or azide functionalities, under click reaction conditions. The terms "complementary terminal functionality" and "complementary terminal functional group" as used in the context of the present invention means a terminal chemical group that is capable of reacting with another chemical group to form a covalent intermolecular bond there between.

An appropriate click reaction for the formation of 1,2,3-triazoles is the Huisgen 1,3-dipolar cycloaddition of azides and alkynes (thermal) which gives a mixture of the 1,4 and 1,5 regioisomers of the 1,2,3-triazole. Click reactions suitable for forming triazole moieties may also be metal catalysed. For example, a Copper(I)-catalyzed Azide-Alkyne Cycloaddition (CuAAC) variant of the Huisgen cycloaddition of azides and terminal alkynes forms 1,2,3-triazoles. Use of a copper catalyst in the Huisgen cycloaddition reaction results in formation of a 1,4-substituted 1,2,3-triazole from azides and terminal alkynes, while use of a ruthenium catalyst enables use of terminal or internal alkynes and results in the formation of the alternate 1,5-regiosiomer. The use of a silver catalyst also results in the 1,4-substituted 1,2,3-triazole. Other metals that can be used include, but are not limited to, Ni, Pt, Pd, Rh, and Ir; the regiochemistry of the 1,2,3 triazole resulting from the use of these metal catalysts is less well defined Some exemplary click functional groups have been described by W. H. Binder and R. Sachsenhofer in Macromol. Rapid Commun., 2007, 28, 15-54, the disclosure of which is incorporated herein by reference.

In one aspect the invention provides a drug-polymer conjugate, which is a copolymer of at least one monomer of formula (I):

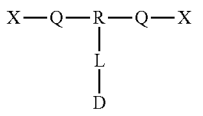

(I)

where:

X may be the same or different at each occurrence and represents a terminal functional group comprising an alkyne or an azide;

Q is independently selected at each occurrence and may be present or absent and when present, represents a linking group;

R is selected from the group consisting of linear or branched hydrocarbon, optionally substituted aryl and optionally substituted heteroaryl;

D is a releasable bicyclic prostaglandin drug;

L is a linker group;

and at least one co-monomer of Formula III $$J\text{-}(Y^1\text{-}A)_n \qquad \text{III}$$

J represents a linking functional group, n is 2 to 8, preferably 3 to 8;

$Y^1$ comprises a polyether of formula $(OR^a)_m$ wherein $R^a$ is independently ethylene, propylene and butylene and m is from 1 to 300 (preferably 2 to 300) and the polyether is in chain with one or more groups which are preferably selected from one or more of optionally substituted straight or branched $C_1$ to $C_{10}$ alkylene, amino, ether, ester, amide, carbonate and carbamate;

A may be the same or different at each occurrence and represents a group comprising a terminal functional group comprising an alkyne or an azide functionality, wherein said terminal functional group is complementary to the terminal functional group X of formula (I) providing triazole moieties from reaction of X and A.

The embodiment in which n is 3 to 8 provides particular advantages in controlling biodegradation of the polymer backbone while also providing a sold polymer which can be formed into a relatively dense article such as a pellet for placement at a site in the body of the subject where effective treatment with a bicyclic prostaglandin (and optionally also β-blocker) is required over a period of time such as at least 10 days, at least 20 days or at least 30 days.

Examples of the group Q which may be present in the drug monomer of formula (I) include groups of formula:

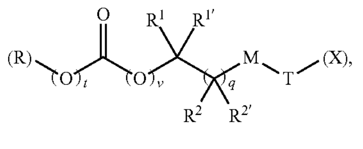

-continued

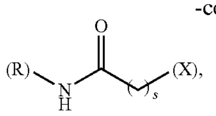

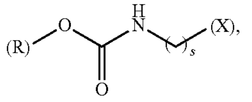

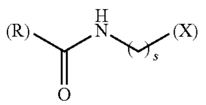

and

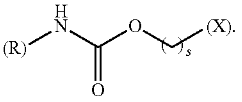

wherein each of t and v are independently 0 or 1 and at least one of t and v is 1 (preferably one of t and v is 1 and the other is 0);

$R^1$, $R^{1'}$, $R^2$ and $R^{2'}$ are independently selected from the group consisting of hydrogen, alkyl, alkoxy and alkoxyalkyl, and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and s is from 0 to 10, preferably 0 t0 6 such as 0, 1, 2 or 3.

More specific examples of Q may be selected from the group consisting of:

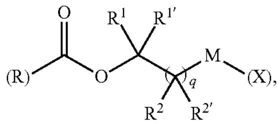

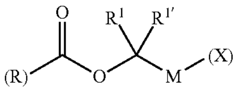

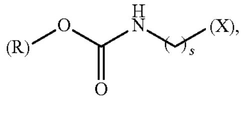

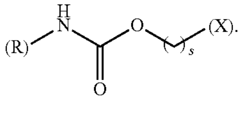

In one aspect the invention provides a drug-polymer conjugate comprising a polymer backbone and a plurality of drugs covalently bound to and pendant from the polymer backbone wherein the polymer backbone comprises a plurality of biodegradable groups of Formula (II):

(II)

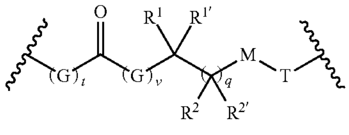

wherein:

G are independently selected from oxygen and $NR^{16}$ where $R^{16}$ is hydrogen or $C_1$ to $C_4$ alkyl;

each of t and v are independently 0 or 1 and at least one of t and v is 1 (preferably one of t and v is 1 and the other is 0); $R^1$, $R^{1'}$, $R^2$ and $R^{2'}$ are independently selected from the group consisting of hydrogen, alkyl, alkoxy and alkoxyalkyl, and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and q is 0 or 1; and M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

and

T is a triazole moiety.

The unit of formula (II) may be provided by the monomer of formula (I), the comonomer of formula III.

In one embodiment at least one of $R^1$, $R^{1'}$, $R^2$ and $R^{2'}$ is preferably not hydrogen. The presence of substituents has been found to regulate the rate of biodegradation and their use can allow the period of effective delivery to be determined in combination with the Network structure provided when n in the comonomer of formula (III) or (IIIa) is 3 to 8.

The compound of formula I includes a number of variables and may be in the form of any one of formulae (IIa), (IIb), (IIc), (IId) or combinations of two or more thereof in the polymer backbone:

(IIa)

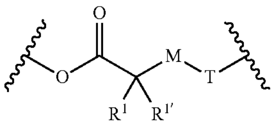

(IIb)

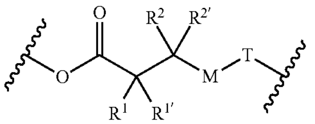

(IIc)

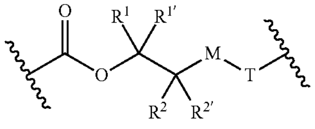

(IId)

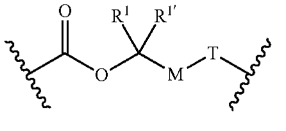

wherein the groups $R^1$, $R^{1'}$, $R^2$, $R^{2'}$, M and T are as herein defined in respect of formula II.

In one set of embodiments the drug-polymer conjugate comprising a plurality of polymer segments of formula V (V)

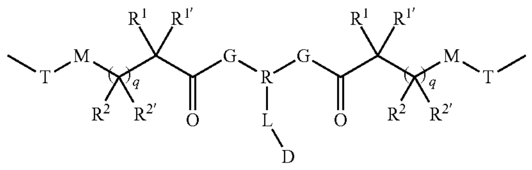

wherein $R^1$, $R^{1'}$, $R^2$ and $R^{2'}$ are independently selected from the group consisting of hydrogen, alkyl, alkoxy and alkoxyalkyl, and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and at least one of $R^1$, $R^{1'}$, $R^2$ and $R^{2'}$ present in the polymer is not hydrogen;

M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1;

R is selected from the group consisting of linear or branched hydrocarbon, optionally substituted aryl and optionally substituted heteroaryl;

L is a linker group; and

D is a releasable bicyclic prostaglandin drug; and

T is a triazole moiety.

In some embodiments of the co-monomer of formula III the group B is a bond, oxygen, the group of formula -MOC(O)N(H)M'- or the group formula (VIa)

(VIa)

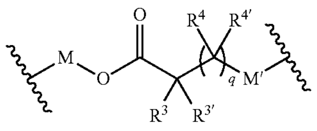

wherein

M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and wherein the groups $R^3$, $R^{3'}$, $R^4$ and $R^{4'}$ are selected from the group consisting of hydrogen, $C_1$ to $C_6$ alkyl, $C_1$ to $C_6$ alkoxy and $C_1$ to $C_6$ alkoxy-($C_1$ to $C_6$ alkyl) and wherein one of the pairs of $R^3$, $R^3$ and $R^4$, $R^{4'}$, may between the members of the pair form a carbocycle or heterocycle of 3 to 6 constituent ring members wherein the heterocycle may comprise from 1 to 3 constituent oxygen heteroatom ring members.

In some embodiments at least one of the groups R3, R3', R4 and R4' is other than hydrogen.

The segment of formula (VIa) may be oriented between the groups $(OR^a)_m$ and A and this may be of orientation (VIa) or (VIb):

(VIa)

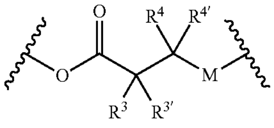

or (VIb)

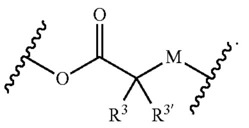

In this embodiment the resulting polymer comprises substituents $R^1$, $R^{1'}$, $R^2$, $R^{2'}$, $R^3$, $R^{3'}$, (and in the case of formula (IVa) $R^4$ and $R^{4'}$) at least one of which is not hydrogen. In some embodiments at least one of $R^1$, $R^{1'}$, $R^2$, $R^{2'}$ is other than hydrogen, in other embodiments at least one of $R^3$, $R^{3'}$, $R^4$ and $R^{4'}$ is other than hydrogen one in some embodiments at least one of the groups $R^1$, $R^{1'}$, $R^2$, $R^{2'}$ is other than hydrogen and at least one of $R^3$, $R^{3'}$, $R^4$ and $R^{4'}$ is other than hydrogen.

In some embodiments, the polymer backbone of the polymer-drug conjugate comprises at least one triazole moiety selected from the group consisting of formula (VIIa) and (VIIb)):

(VIIa)

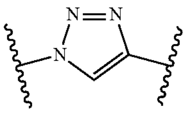

(VIIb)

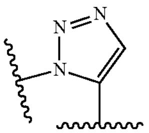

The backbone may comprise a multiplicity of triazole moiety such as (VIIa), (VIIb) and combinations thereof.

Additional co-monomers useful for the preparation of polymer-drug conjugates of the invention comprise terminal functional groups comprising an alkyne and/or an azide. One skilled in the relevant art would understand that under appropriate reaction conditions, an alkyne and an azide containing functional groups can covalently react to form a triazole moiety. Click reaction conditions have been described in for example, Chem. Rev. 2008, 108, 2952, Angew Chem Int Ed 2001, 40, 2004, Angew Chem Int Ed Engl. 2002, Jul. 15, 41(14): 2596-9, Aldrichimica Acta 2010, 43 (1) 15 and Accounts of Chemical Research 44 (9): 666-676.

The drug conjugated with the polymer backbone of the drug-polymer conjugate and in the monomer includes a bicyclic prostaglandins. The drug-polymer conjugate may comprise further actives such as β-blockers and combinations of two or more thereof. In some embodiments it is useful to have the two drug classes for specific treatments or to optimise treatment. Combinations of drugs from the bicyclic prostaglandin and -blocker classes are therapies that may be provided by conjugation of these two drugs to the same polymer backbone by, for example forming the polymer with a mixture of monomers of formula I where D is selected from bicyclic prostaglandins in at least one monomer and D is selected from β-blockers in at least one monomer. β-blockers are antagonists of β-adrenoreceptor sites and are used to treat or manage a range of conditions, including cardiac arrhythmias, hypertension, hypotension and glaucoma. Elevated intraocular pressure (ocular hypertension) is a risk factor for glaucoma. β-blockers can reduce intraocular pressure and exert an ocular hypotensive effect by reducing the production of aqueous humour in the eye. In further embodiments the drug polymer conjugate may comprise other prostaglandins such as the prostaglandin analogues disclosed in copending application WO2018/165711

In the monomer-drug conjugate of formula (I) each substituent X represents a group comprising a terminal functional group comprising an alkyne or azide functionality. The terminal functional group X may be the same or different at each occurrence. Where the terminal functional groups (X) are the same, the monomer will generally be a diazide or dialkynyl monomer.

One skilled in the relevant art would understand that the terms "alkyne" and "azide" represent the following structures:

Alkyne: $-C\equiv CH$

Azide: $-N=\overset{+}{N}=\overset{-}{N}$

In one embodiment the drug is conjugated to the polymer backbone via an ester linkage formed between the drug D and the linker L. For example in one embodiment the drug is covalently bonded to the linker by a carboxylic acid ester. The ester may comprise an acid portion —C(O)— derived from an acid functional group of the drug and an alcohol portion provided by the linker or an acid portion of the ester may be derived from the linker and the alcohol portion by the drug.

The drug moiety (D) in formula (I), (IV), (IVa) to (IVd), (V) and (XXX) comprises a bicyclic prostaglandin. The bicyclic prostaglandin may be of formula (X), (Xa), (Xb), (Xa-1) or (Xa-2).

Bicyclic prostaglandins as described herein constitute an α-chain, an ω-chain and a bicyclic ring structure, typically a cyclic ether, fused with the 5-membered ring, In one aspect, the present invention relates to a drug-polymer conjugate comprising a polymer backbone and a EP2 or EP3 class of bicyclic prostaglandins conjugated to the polymer backbone. The bicyclic prostaglandins are prostacyclin analogues and are believed to act as G protein-based EP2 receptor agonists.

Specific examples of bicyclic prostaglanding are described in US2012/0122964, EP2669280 and/or EP3480191 the contents of which are herein incorporated by reference.

Bicyclic prostaglandins delivered by polymer-drug conjugates of the invention comprise at least one functional group selected from the group consisting of a carboxylic acid group and a hydroxy group.

The carboxylic acid group and the hydroxy groups of the bicyclic prostaglandin of Formula Xa and Xb can serve as reactive functional groups for conjugation of the bicyclic prostaglandin drug to a polymer. In conjugating the drug to the polymer backbone, the bicyclic prostaglandin is conjugated to the polymer backbone via an ester link made up of the acid residue of the carboxylic acid and an alcohol residue of linker L or and acid residue of the linker and alcohol residue of the bicyclic bicyclic prostaglandin. The drug moiety (denoted D in formulae described herein) linked to the polymer is therefore an acid residue (in the case of conjugation at the 1 position) or an alcohol residue (in the case of conjugation at the alcohol group positions) of the ester, anhydride or carbonate linking group conjugating the bicyclic prostaglandin to the polymer backbone. The moiety represented by D may therefore be a releasable bicyclic prostaglandin.

The bicyclic prostaglandin may be conjugated to the polymer backbone via an ester (including [alkoxycarbonyl)oxy]alkyl ester), anhydride or carbonate linking group. Ester (including [alkoxycarbonyl)oxy]alkyl ester), anhydride and carbonate linking groups have been found to be hydrolytically labile in biological environments and can help to ensure that a sufficient amount of the drug is effectively released from the polymer conjugate to achieve therapeutic levels in the immediate vicinity of the polymer conjugate material.

When the bicyclic prostaglandin may be conjugated to the polymer backbone by an [alkoxycarbonyl)oxy]alkyl ester linking group, the [alkoxycarbonyl)oxy]alkyl ester group may link the drug at the carboxylic acid group of the drug providing an ester link.

When the bicyclic prostaglandin is conjugated to the polymer backbone by an anhydride linking group, the anhydride linking group may link the drug at the 1 position of the drug.

As used herein, the term "acid residue" is a reference to that part of an ester or anhydride linking group that is derived from a carboxylic acid functional group of a drug, after conjugation of the drug to the polymer backbone. The acid residue will generally have the structure —C(O)—. In the case of a bicyclic prostaglandin, the carboxylic acid group is located at the 1 position.

As used herein the term "alcohol residue" is a reference to that part of an ester or carbonate linking group that is derived from a hydroxy functional group of a drug, after conjugation of the drug to the polymer backbone. The alcohol residue will generally have the structure —O—. In the case of a bicyclic prostaglandin, the hydroxy group may those shown in formula Xa, Xa-1 and Xa-2.

Examples of the drug monomer conjugate of formula II wherein the drug is a bicyclic prostaglandin in acid residue form include monomers of formula (IVb) and (IVc):

(IVb)

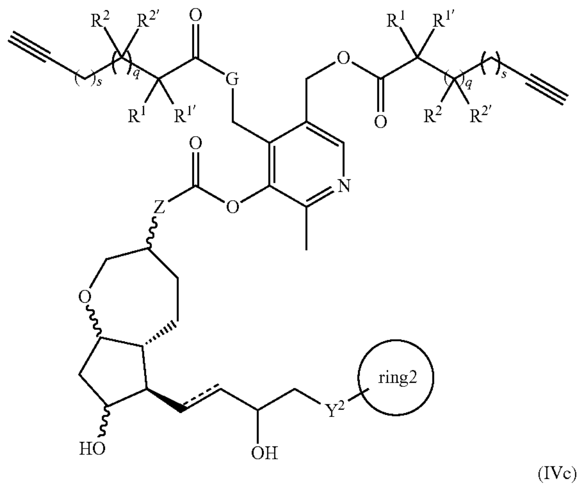

(IVc)

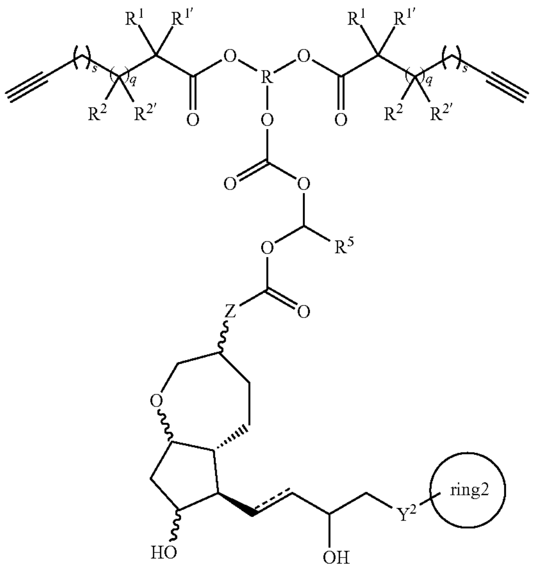

wherein the groups $R^1$, $R^{1'}$, $R^2$ and $R^{2'}$ are independently selected from the group consisting of hydrogen, $C_1$ to $C_6$ alkyl, $C_1$ to $C_6$ alkoxy and $C_1$ to $C_6$ alkoxy-($C_1$ to $C_6$ alkyl); and wherein one of the pairs of $R^1$, $R^1$ and $R^2$, $R^{2'}$, may between the members of the pair form a carbocycle or heterocycle of 3 to 6 constituent ring members wherein the heterocycle may comprise from 1 to 3 constituent heteroatom ring members selected from oxygen and nitrogen which nitrogen may be substituted by $C_1$ to $C_6$ alkyl;

s is from 0 to 6 (preferably 0 to 2);

q is 0 or 1;

$R^5$ is hydrogen or methyl;

Z is selected from the group consisting of;

—$(CH_2)_m$— wherein m is from 1 to 10 preferably 2 to 4;

—$(CH_2)_n$—CH═CH— wherein n is from 1 to 6, preferably 1 or 2;

—$(CH_2)_p$-A-$CH_2$— wherein A is oxygen or sulfur; and the group ring 1 is selected from optionally substituted, aromatic or non-aromatic, carbocyclic and heterocyclic rings;

------ represents a double or single bond;

$Y^2$ is selected from —$CH_2$—, oxygen or sulfur; and ring 2 is selected from optionally substituted, aromatic or non-aromatic, carbocyclic and heterocyclic rings.

In a particularly preferred embodiment at least one of $R^1$, $R^{1'}$, $R^2$ and $R^{2'}$ is other than hydrogen. The monomer in which at least one of $R^1$, $R^{1'}$, $R^2$ and $R^{2'}$ is other than hydrogen provides useful additional control of biodegradation in the monomer unit derived from these drub monomer conjugates.

Specific examples of the drug-polymer conjugate include conjugates of formula V (V)

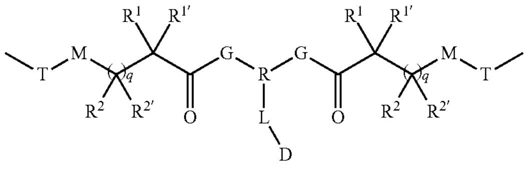

wherein the substituents are as hereinbefore defined except that D is selected from the specific bicyclic prostaglandins in the form of the acid residue as shown in Table 1.

Specific drug-monomers are of formula (II):

(IV)

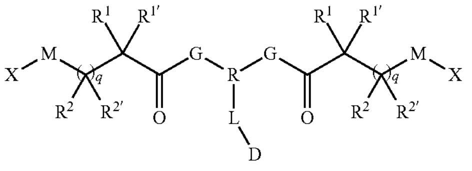

wherein the substituents are as hereinbefore defined except that D is selected from the specific bicyclic prostaglandins in the form of the acid residue as shown in Table 1.

TABLE 1

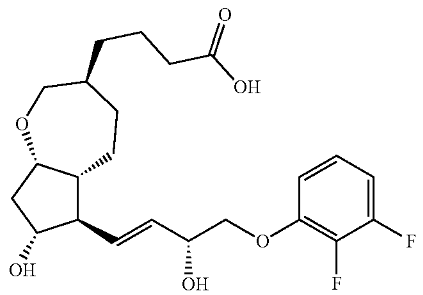 [SMILES: O=C(O)CCC[C@H]1CC[C@@H]2[C@@H](/C=C/[C@@H](O)COc3cccc(F)c3F)[C@H](O)C[C@@H]2OC1]

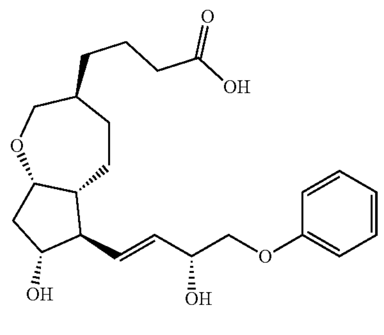 [SMILES: O=C(O)CCC[C@H]1CC[C@@H]2[C@@H](/C=C/[C@@H](O)COc3ccccc3)[C@H](O)C[C@@H]2OC1]

TABLE 1-continued
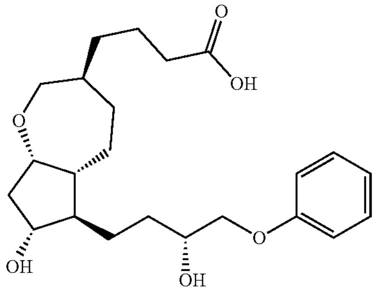 [SMILES: O=C(O)CCC[C@H]1CC[C@@H]2[C@@H](CC[C@@H](O)COc3ccccc3)[C@H](O)C[C@@H]2OC1]
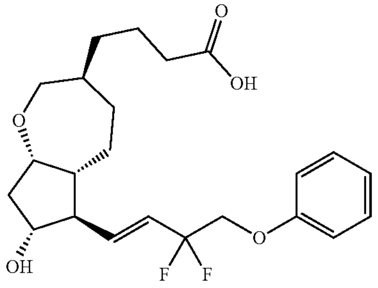 [SMILES: O=C(O)CCC[C@H]1CC[C@@H]2[C@@H](/C=C/C(F)(F)COc3ccccc3)[C@H](O)C[C@@H]2OC1]
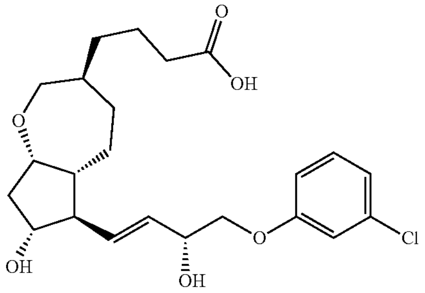 [SMILES: O=C(O)CCC[C@H]1CC[C@@H]2[C@@H](/C=C/[C@@H](O)COc3cccc(Cl)c3)[C@H](O)C[C@@H]2OC1]
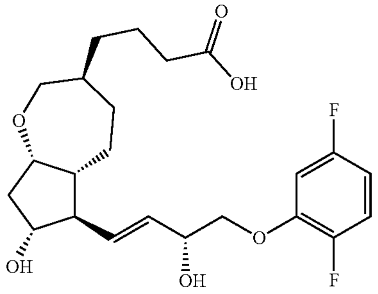 [SMILES: O=C(O)CCC[C@H]1CC[C@@H]2[C@@H](/C=C/[C@@H](O)COc3cc(F)ccc3F)[C@H](O)C[C@@H]2OC1]
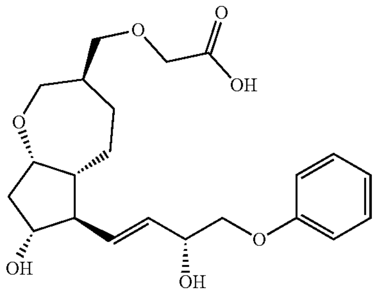 [SMILES: O=C(O)COC[C@H]1CC[C@@H]2[C@@H](/C=C/[C@@H](O)COc3ccccc3)[C@H](O)C[C@@H]2OC1]
TABLE 1-continued
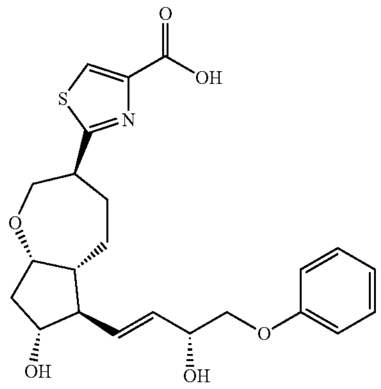 [SMILES: O=C(O)c1csc([C@H]2CC[C@@H]3[C@@H](/C=C/[C@@H](O)COc4ccccc4)[C@H](O)C[C@@H]3OC2)n1]
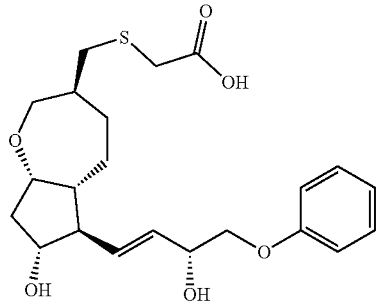 [SMILES: O=C(O)CSC[C@H]1CC[C@@H]2[C@@H](/C=C/[C@@H](O)COc3ccccc3)[C@H](O)C[C@@H]2OC1]
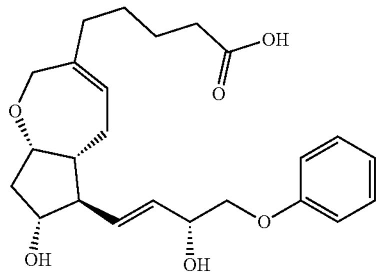 [SMILES: O=C(O)CCCCC1=CC[C@@H]2[C@@H](/C=C/[C@@H](O)COc3ccccc3)[C@H](O)C[C@@H]2OC1]
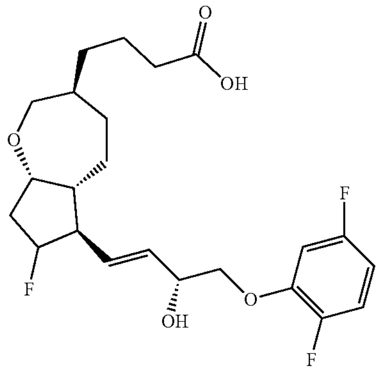 [SMILES: O=C(O)CCC[C@H]1CC[C@H]2[C@H](CC(F)[C@@H]2/C=C/[C@@H](O)COc2cc(F)ccc2F)OC1]

TABLE 1-continued

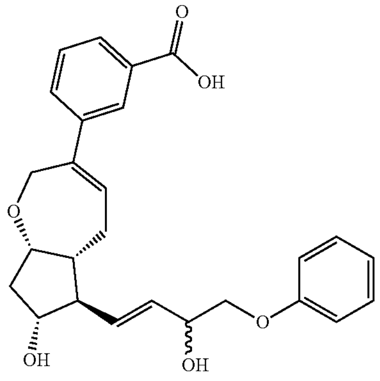 [SMILES: O=C(O)c1cccc(C2=CC[C@@H]3[C@@H](/C=C/C(O)COc4ccccc4)[C@H](O)C[C@@H]3OC2)c1]

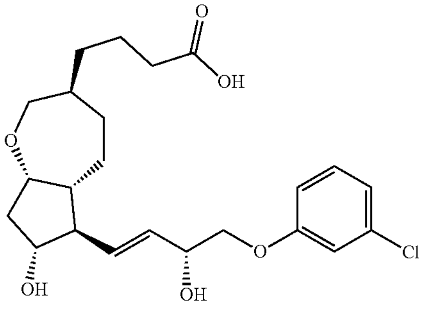 [SMILES: O=C(O)CCC[C@H]1CC[C@@H]2[C@@H](/C=C/[C@@H](O)COc3cccc(Cl)c3)[C@H](O)C[C@@H]2OC1]

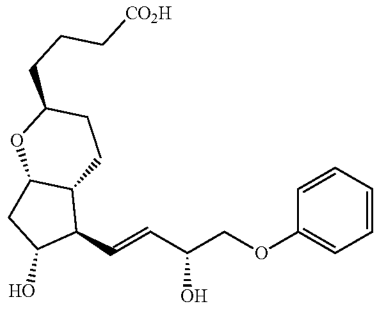 [SMILES: O=C(O)CCC[C@H]1CC[C@@H]2[C@@H](/C=C/[C@@H](O)COc3ccccc3)[C@H](O)C[C@@H]2O1]

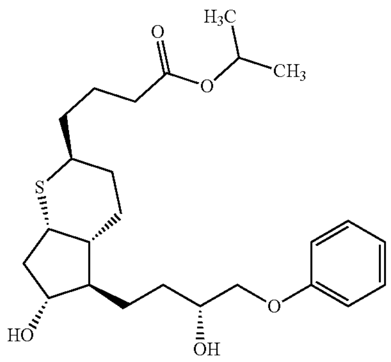 [SMILES: CC(C)OC(=O)CCC[C@H]1CC[C@@H]2[C@@H](CC[C@@H](O)COc3ccccc3)[C@H](O)C[C@@H]2S1]

TABLE 1-continued

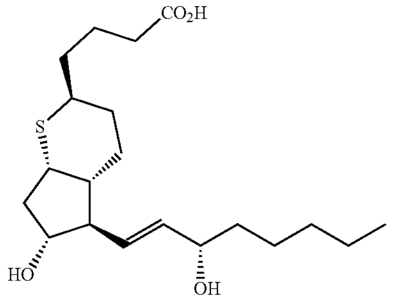 [SMILES: CCCCC[C@H](O)/C=C/[C@@H]1[C@H]2CC[C@H](CCCC(=O)O)S[C@H]2C[C@H]1O]

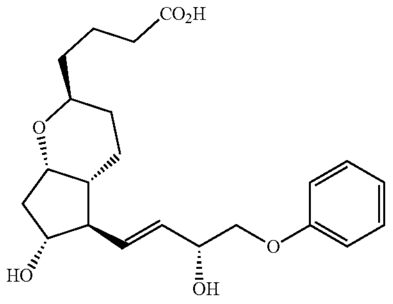 [SMILES: O=C(O)CCC[C@H]1CC[C@@H]2[C@@H](/C=C/[C@@H](O)COc3ccccc3)[C@H](O)C[C@@H]2O1]

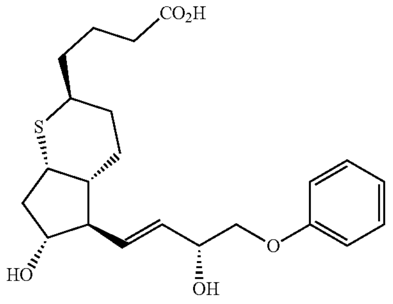 [SMILES: O=C(O)CCC[C@H]1CC[C@@H]2[C@@H](/C=C/[C@@H](O)COc3ccccc3)[C@H](O)C[C@@H]2S1]

In the embodiments if Table 1 the linker L may provide the alcohol portion (—O—) of the ester formed with the acid residue (C═O) of the carboxylic acid of the bicyclic prostaglandins.

The bicyclic prostaglandin in one embodiment is of the following formula and forms an ester with a linker L providing the alcohol portion of the ester wherein D is the acid residue of the carboxylic acid of the bicyclic prostaglandin

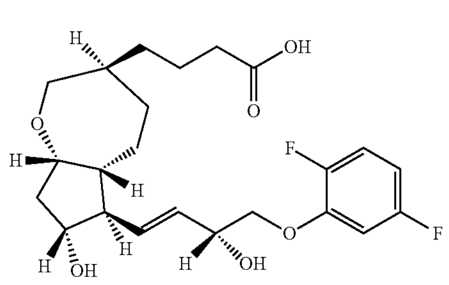 [SMILES: O=C(O)CCC[C@H]1CC[C@@H]2[C@@H](/C=C/[C@@H](O)COc3cc(F)ccc3F)[C@H](O)C[C@@H]2OC1]

Other specific examples of preferred bicyclic prostaglandins useful in forming the monomer and polymer conjugates of the invention include via conjugation via an ester formed with the acid residue of the bicyclic prostaglandin andoxygen (alcohol residue) present in the linker L include:

4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoic acid;

4-{(3S,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}butanoic acid;

4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoic acid;

4-{(2R,4aR,5R,6R,7aS)-6-hydroxy-5-[(1E,3R)-3-hydroxy-4-phenoxy-1-buten-1-yl]octahydrocyclopenta[b]thiopyran-2-yl} butanoic acid; and 4-{(2S,4aR,5R,6R,7aS)-5-[(1E,3R)-4-(4-fluorophenoxy)-3-hydroxy-1-buten-1-yl]-6-hydroxyoctahydrocyclopenta[b]thiopyran-2-yl} butanoic acid.

Specific examples of more preferred bicyclic prostaglandins which may be conjugated via an alcohol substituent on the bicyclic prostaglandins include:

ethyl 4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoate;

2-propanyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate;

2-propanyl 4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoate; and methyl 4-{(2S,4aR,5R,6R,7aS)-6-hydroxy-5-[(1E,3R)-3-hydroxy-4-phenoxy-1-buten-1-yl]octahydrocyclopenta[b]thiopyran-2-yl} butanoate.

Such compounds may form an ester with linker L via an alcohol residue of the bicyclic prostaglandin and an acid residue present in linker L.

In preferred embodiments the linker L may be of formula selected from the group consisting of (R) —O— (D);

(R) —OC(O)—Ar—O— (D);

(R) —NHC(O)—Ar—O— (D);

(R) —C(O)O—$C_{1-12}$alkylene-O— (D);

(R) —OC(O)O—$C_{1-12}$alkylene-O— (D)

(R) —OC(O)—$C_1$-$C_{12}$alkylene-O— (D).

In more preferred embodiments L is selected from (R) —O— (D);

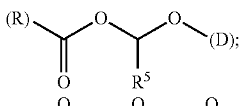

and

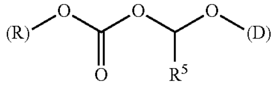

where $R^5$ is selected from hydrogen and $C_1$ to $C_6$ alkyl, preferably from the group consisting of hydrogen, methyl, ethyl, propyl, isopropyl, butyl, isobutyl, sec-butyl, and tert-butyl.

In one particularly preferred embodiment, L is (R) —O— (D); and R is selected from the group consisting of

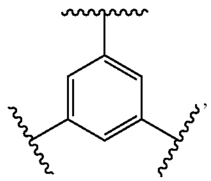

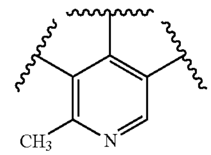

or

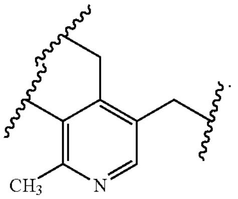

In a further particularly preferred embodiment, L is

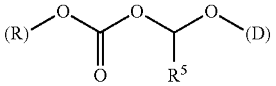

where $R^5$ is selected from hydrogen and $C_1$ to $C_6$ alkyl, preferably from the group consisting of hydrogen, methyl, ethyl, propyl, isopropyl, butyl, isobutyl, sec-butyl, and tert-butyl; and R is a saturated hydrocarbon of from 1 to 10 carbon atoms. More preferred $R^5$ are hydrogen and methyl.

Examples of suitable spacer moieties that may form part of L include the divalent form of a group selected from oxy (—O—), alkyl, alkenyl, alkynyl, aryl, acyl (including —C(O)—), carbocyclyl, heterocyclyl, heteroaryl, alkyloxy, alkenyloxy, alkynyloxy, aryloxy, acyloxy, carbocyclyloxy, heterocyclyloxy, heteroaryloxy, alkylthio, alkenylthio, alkynylthio, arylthio, acylthio, carbocyclylthio, heterocyclylthio, heteroarylthio, alkylalkenyl, alkylalkynyl, alkylaryl, alkylacyl, alkylcarbocyclyl, alkylheterocyclyl, alkylheteroaryl, alkyloxyalkyl, alkenyloxyalkyl, alkynyloxyalkyl, aryloxyalkyl, alkylacyloxy, alkyloxyacylalkyl, alkylcarbocyclyloxy, alkylheterocyclyloxy, alkylheteroaryloxy, alkylthioalkyl, alkenylthioalkyl, alkynylthioalkyl, arylthioalkyl, alkylacylthio, alkylcarbocyclylthio, alkylheterocyclylthio, alkylheteroarylthio, alkylalkenylalkyl, alkylalkynylalkyl, alkylarylalkyl, alkylacylalkyl, arylalkylaryl, arylalkenylaryl, arylalkynylaryl, arylacylaryl, arylacyl, arylcarbocyclyl, arylheterocyclyl, arylheteroaryl, alkenyloxyaryl, alkynyloxyaryl, aryloxyaryl, arylacyloxy, arylcarbocyclyloxy, arylheterocyclyloxy, arylheteroaryloxy, alkylthioaryl, alkenylthioaryl, alkynylthioaryl, arylthioaryl, arylacylthio, arylcarbocyclylthio, arylheterocyclylthio, and arylheteroarylthio, wherein where present the or each —$CH_2$— group in any alkyl chain may be replaced by a divalent group independently selected from —O—, —$OP(O)_2$—, —$OP(O)_2O$—, —S—, —S(O)—, —$S(O)_2O$—, —$OS(O)_2O$—, —N═N—, —$OSi(OR^b)_2O$—, —$Si(OR^b)_2O$—, —$OB(OR^b)O$—, —$B(OR^b)O$—, —$NR^b$—, —C(O)—, —C(O)O—, —OC(O)O—, —OC(O)$NR^b$— and —C(O)$NR^b$—, where the or each $R^b$ may be independently selected from hydrogen, alkyl, alkenyl, alkynyl, aryl, carbocyclyl, heteroaryl, heterocyclyl, arylalkyl, and acyl. The one or more $R^b$ groups may also be independently selected from hydrogen, $C_{1-18}$alkyl, $C_{1-18}$alkenyl, $C_{1-18}$alkynyl, $C_{6-18}$aryl, $C_{3-18}$carbocyclyl, $C_{3-18}$heteroaryl, $C_{3-18}$heterocyclyl, and $C_{7-18}$arylalkyl.

In some embodiments the spacer moiety may be branched. Where the spacer moiety is branched, two or more releasable drugs may be appended to the spacer moiety.

In the lists above defining groups (generally divalent) from which each spacer moiety may be selected, each alkyl, alkenyl, alkynyl, aryl, carbocyclyl, heteroaryl, and heterocyclyl moiety may be optionally substituted. For avoidance of any doubt, where a given spacer moiety contains two or more of such moieties (e.g. alkylaryl), each of such moieties may be optionally substituted with one, two, three or more optional substituents as herein defined.

In the lists above defining groups (generally divalent) from which the or each spacer moiety may be selected, where a given spacer moiety contains two or more subgroups (e.g. [group A][group B]), the order of the subgroups is not intended to be limited to the order in which they are presented. Thus, a spacer moiety with two subgroups defined as [group A][group B] (e.g. alkylaryl) is intended to also be a reference to a spacer moiety with two subgroups defined as [group B][group A] (e.g. arylalkyl).

Some specific examples of spacer moieties that may form part of L include: —O—; —C(O)—; —OC(O)— and optionally substituted: —OC(O)—$C_{1-18}$alkylene-C(O)—; —C(O)O—$C_1$-$C_{18}$alkylene-C(O)—; —O—Ar—C(O)O—; —O—Ar—C(O)—N$R^b$—; —O—Ar—; —O—Ar—; —C(O)O—Ar—C(O)O—; —C(O)O—Ar—C(O)—N$R^b$—; —C(O)O—Ar—; —C(O)O—Ar—; —N$R^b$C(O)—$C_1$-$C_{18}$alkylene-C(O)—; —C(O)O—$C_1$-$C_{18}$alkylene-O—; —OC(O)O—$C_1$-$C_{18}$alkylene-O—; —O—$C_1$-$C_{18}$alkylene-O—; —O—$C_1$-$C_{18}$alkylene-N$R^b$—; —OC(O)—$C_1$-$C_{18}$alkylene-N$R^b$—; —C(O)—$C_1$-$C_{18}$alkylene-N$R^b$—; —OC(O)—$C_1$-$C_{18}$alkylene-O—; —C(O)—$C_1$-$C_{18}$alkylene-O—; and —C(O)N$R^b$—$C_1$-$C_{18}$alkylene-N$R^b$— where $R^b$ is as defined above for the spacer moiety.

In one form of the invention, exemplary spacer moieties include: —O—; —C(O)—; —OC(O)O—$C_1$-$C_{18}$alkylene-O—; and —OC(O)—$C_{1-18}$alkylene-C(O)—, such as —OC(O)—$C_{2-3}$alkylene-C(O)—, —O—$C_{5-6}$Ar—C(O)O and —C(O)O—$C_{5-6}$Ar—C(O)O—.

The choice of spacer moieties will determine the spacing of the drugs from the polymer backbone. The skilled artisan would be capable of selecting the appropriate spacer moiety based on an evaluation of steric constraints, phase chemistry and surface chemistry. For example, larger drugs can be advantageously spaced from the monomer by the choice of a longer spacer moiety.

In the moieties of formulae (I), (IV), (V) and (XXX), the drug (D) is coupled to R through a cleavable linking group denoted by L. As used herein "linking group" refers to a generally divalent substituent group that couples D to R. The substituent group, generally the group linking L to D such as an ester, anhydride or carbonate, is cleavable so that the drug is releasable.

In some embodiments, the cleavable linking group represented by L is a cleavable covalent bond that directly couples the drug to the polymer backbone.

In other embodiments, the cleavable linking group represented by L comprises a spacer moiety and a cleavable covalent bond. The spacer moiety is attached to the polymer backbone while the cleavable covalent bond couples the spacer moiety to the drug. In some embodiments of a polymer-drug conjugate of the invention, it is a proviso that L does not include a triazole moiety. Thus, polymer conjugates of the invention do not include drugs coupled to the polymer backbone via a product of a click chemistry reaction.

The covalent bond coupling the drug (D) with the linking group (L) is not a carbon-carbon bond. Accordingly, the cleavable covalent bond will generally form part of a functional group selected from: esters; carbonates; and anhydrides. Of these functional groups, esters and carbonates are preferred. A skilled person would recognise that such groups are capable of being cleaved, for example hydrolytically, enzymatically, and/or by radical mechanisms, so as to release the drug.

The present invention preferably employs a group selected from ester, anhydride and carbonate linking groups to conjugate the drug to the polymer backbone as such linking groups have been found to be hydrolytically labile in biological environments. Such linking groups may also be generally more labile than other groups or moieties that may be present in the polymer-drug conjugate, such as for example, biodegradable moieties that may be present in the polymer backbone of polymer conjugates of some embodiments of the invention. Ester, anhydride and carbonate linking groups may further help to ensure that a sufficient amount of the drug is effectively released from the polymer conjugate to achieve therapeutic levels in the immediate vicinity of the polymer conjugate material.

Breakdown of the cleavable covalent bond can be promoted hydrolytically (i.e. hydrolytic cleavage) and may take place in the presence of water and an acid or a base. In some embodiments the cleavage may take place in the presence of one or more hydrolytic enzymes or other endogenous biological compounds that catalyze or at least assist in the cleavage process. For example, an ester bond may be hydrolytically cleaved to produce a carboxylic acid and an alcohol.

At the very least the drug will be releasable from the conjugate per se. However, as further described below, the polymer backbone may also biodegrade in vivo or in vitro such that the polymer backbone breaks into lower molecular weight fragments, with the drug remaining tethered to such a fragment(s) via L. In that case, the drug will nevertheless still be capable of being released or cleaved from L, which may or may not still be associated with the polymer conjugate per se.

As indicated above, drug as described herein may be coupled to a spacer moiety, which in turn is attached to the polymer backbone. As used herein, the terms "spacer", "spacer group" or "spacer moiety" refer to an atom or any straight chain or branched, symmetric or asymmetric compound capable of linking or coupling the drug to a polymer backbone.

In some embodiments, the "spacer", "spacer group" or "spacer moiety" refers to a substituent which is generally divalent. As outlined above, the covalent bond between the spacer moiety and the drug is cleavable so that the drug is releasable.

Examples of suitable spacer moieties that may form part of L include the divalent form of a group selected from oxy (—O—), alkyl, alkenyl, alkynyl, aryl, acyl (including —C(O)—), carbocyclyl, heterocyclyl, heteroaryl, alkyloxy, alkenyloxy, alkynyloxy, aryloxy, acyloxy, carbocyclyloxy, heterocyclyloxy, heteroaryloxy, alkylthio, alkenylthio, alkynylthio, arylthio, acylthio, carbocyclylthio, heterocyclylthio, heteroarylthio, alkylalkenyl, alkylalkynyl, alkylaryl, alkylacyl, alkylcarbocyclyl, alkylheterocyclyl, alkylheteroaryl, alkyloxyalkyl, alkenyloxyalkyl, alkynyloxyalkyl, aryloxyalkyl, alkylacyloxy, alkyloxyacylalkyl, alkylcarbocyclyloxy, alkylheterocyclyloxy, alkylheteroaryloxy, alkylthioalkyl, alkenylthioalkyl, alkynylthioalkyl, arylthioalkyl, alkylacylthio, alkylcarbocyclylthio, alkylheterocyclylthio, alkylheteroarylthio, alkylalkenylalkyl, alkylalkynylalkyl, alkylarylalkyl, alkylacylalkyl, arylalkylaryl, arylalkenylaryl, arylalkynylaryl, arylacylaryl, arylacyl, arylcarbocyclyl, arylheterocyclyl, arylheteroaryl, alkenyloxyaryl, alkynyloxyaryl, aryloxyaryl, arylacyloxy, arylcarbocyclyloxy, arylheterocyclyloxy, arylheteroaryloxy, alkylthioaryl, alkenylthioaryl, alkynylthioaryl, arylthioaryl, arylacylthio, arylcarbocyclylthio, arylheterocyclylthio, and arylheteroarylthio, wherein where present the or each —$CH_2$— group in any alkyl chain may be replaced by a divalent group independently selected from —O—, —$OP(O)_2$—, —$OP(O)_2O$—, —S—, —S(O)—, —$S(O)_2O$—, —$OS(O)_2O$—, —N═N—, —$OSi(OR^b)_2O$—, —$Si(OR^b)_2O$—, —$OB(OR^b)O$—, —$B(OR^b)O$—, —$NR^b$—, —C(O)—, —C(O)O—, —OC(O)O—, —OC(O)$NR^b$— and —C(O)$NR^b$—, where the or each $R^b$ may be independently selected from hydrogen, alkyl, alkenyl, alkynyl, aryl, carbocyclyl, heteroaryl, heterocyclyl, arylalkyl, and acyl. The one or more $R^b$ groups may also be independently selected from hydrogen, $C_{1-18}$alkyl, $C_{1-18}$alkenyl, $C_{1-18}$alkynyl, $C_{6-18}$aryl, $C_{3-18}$carbocyclyl, $C_{3-18}$heteroaryl, $C_{3-18}$heterocyclyl, and $C_{7-18}$arylalkyl.

In some embodiments the spacer moiety may be branched. Where the spacer moiety is branched, two or more releasable drugs may be appended to the spacer moiety.

In the lists above defining groups (generally divalent) from which each spacer moiety may be selected, each alkyl, alkenyl, alkynyl, aryl, carbocyclyl, heteroaryl, and heterocyclyl moiety may be optionally substituted. For avoidance of any doubt, where a given spacer moiety contains two or more of such moieties (e.g. alkylaryl), each of such moieties may be optionally substituted with one, two, three or more optional substituents as herein defined.

In the lists above defining groups (generally divalent) from which the or each spacer moiety may be selected, where a given spacer moiety contains two or more subgroups (e.g. [group A][group B]), the order of the subgroups is not intended to be limited to the order in which they are presented. Thus, a spacer moiety with two subgroups defined as [group A][group B] (e.g. alkylaryl) is intended to also be a reference to a spacer moiety with two subgroups defined as [group B][group A] (e.g. arylalkyl).

Some specific examples of spacer moieties that may form part of L include: —O—; —C(O)—; —OC(O)— and optionally substituted: —OC(O)—$C_{1-18}$alkylene-C(O)—; —C(O)O—$C_1$-$C_{18}$alkylene-C(O)—; —O—Ar—C(O)O—; —O—Ar—C(O)—$NR^b$—; —O—Ar—; —O—Ar—; —C(O)O—Ar—C(O)O—; —C(O)O—Ar—C(O)—$NR^b$—: —C(O)O—Ar—: —C(O)O—Ar—; —$NR^b$C(O)—$C_1$-$C_{18}$alkylene-C(O)—; —C(O)O—$C_1$-$C_{18}$alkylene-O—; —OC(O)O—$C_1$-$C_{18}$alkylene-O—; —O—$C_1$-$C_{18}$alkylene-O—; —O—$C_1$-$C_{18}$alkylene-$NR^b$—; —OC(O)—$C_1$-$C_{18}$alkylene-$NR^b$—; —C(O)—$C_1$-$C_{18}$alkylene-$NR^b$—; —OC(O)—$C_1$-$C_{18}$alkylene-O—; —C(O)—$C_1$-$C_{18}$alkylene-O—; and —C(O)$NR^b$—$C_1$-$C_{18}$alkylene-$Nb^a$— where $R^b$ is as defined above for the spacer moiety.

In one form of the invention, exemplary spacer moieties include: —O—; —C(O)—; —OC(O)O—$C_1$-$C_{18}$alkylene-O—; and —OC(O)—$C_{1-18}$alkylene-C(O)—, such as —OC(O)—$C_{2-3}$alkylene-C(O)—, —O—$C_{5-6}$Ar—C(O)O and —C(O)O—$C_{5-6}$Ar—C(O)O—.

The choice of spacer moieties will determine the spacing of the drug as from the polymer backbone. The skilled artisan would be capable of selecting the appropriate spacer moiety based on an evaluation of steric constraints, phase chemistry and surface chemistry. For example, larger drug moieties can be advantageously spaced from the monomer by the choice of a longer spacer moiety.

In some embodiments of a drug-polymer conjugate of the invention, when the drug (D) is a carboxylic acid such as a bicyclic prostaglandin linked to the polymer backbone, then L is of a formula selected from the group consisting of:

(R) —O— (D);
(R) —OC(O)—Ar—O— (D);
(R) —NHC(O)—Ar—O— (D);
(R) —C(O)O—$C_{1-12}$alkylene-O— (D);
(R) —OC(O)O—$C_{1-12}$alkylene-O— (D);
(R) —OC(O)—$C_1$-$C_{12}$alkylene-O— (D);
(R) —OC(O)—O— (D);
(R) —OC(O)—Ar—OC(O) —O— (D);
(R) —NHC(O)—Ar—OC(O)—O (D);
(R) —C(O)O—$C_1$-$C_{12}$alkylene-OC(O)—O (D); and
(R) —OC(O)—$C_1$-$C_{12}$alkylene-OC(O)— (D).

In one embodiment, when the drug is linked via an ester formed with a drug acid residue and an alcohol —O— portion of a linker L, then L may be selected from the group consisting of —O—; —OC(O)—; —OC(O)O—$C_1$-$C_6$alkylene-O—; —O—$C_6$-aryl-C(O)O—; —O—$C_6$-aryl-C(O)NH—; —O-Pyridoxine-; and —O-Phloroglucinol-.

In one embodiment R is an aromatic group selected from the group consisting of:

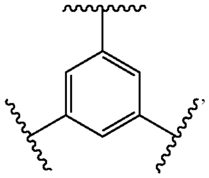
,
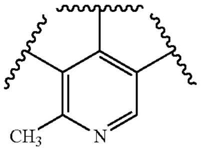
or
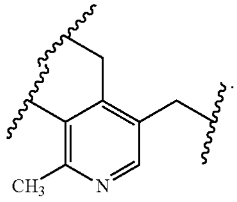
.

and linker L is of formula —O—.

In a further embodiment R is aliphatic of from 1 to 10 carbon atoms and L is of formula:

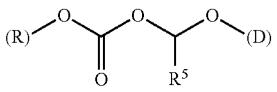

wherein $R^5$ is selected from the group consisting of hydrogen and $C_1$ to $C_6$ alkyl, preferably from the group consisting of hydrogen, methyl, ethyl, propyl, isopropyl, butyl, isobutyl, sec-butyl, and tert-butyl, more preferably hydrogen or methyl.

In some embodiments of a polymer-drug conjugate of the invention, when the drug (D) comprises an alcohol such as in the case of the hydroxyl groups in the bicyclic prostaglandin of formula Xa, then L may be of a formula selected from the group consisting of:

(R) —C(O) (D);
(R) —OC(O)— (D);
(R) —OC(O)—$C_1$-$C_{12}$alkylene-C(O)— (D);
(R) —NHC(O)—$C_1$-$C_{12}$alkylene-C(O)— (D);

(R) —OC(O)—$C_1$-$C_{12}$alkylene-OC(O)-(D);
(R) —NHC(O)—$C_1$-$C_{12}$alkylene-OC(O)— (D);
(R) —OC(O)—Ar—C(O)— (D);
(R) —NHC(O)—Ar—C(O)— (D);
(R) —OC(O)—Ar—OC(O)— (D);
(R) —NHC(O)—Ar—OC(O)— (D).

In a specific embodiment, when the hydroxyl groups of the bicyclic prostaglandin is linked to the polymer backbone, then L is —C(O)—; —C(O)O—$C_1$-$C_5$alkylene-O—; —C(O)—$C_{1-5}$alkylene-C(O)O—; —C(O)—$C_{1-5}$alkylene-C(O)NH—; —C(O)O—; —C(O)O—$C_6$-aryl-C(O)O—; —C(O)O—$C_6$-aryl-C(O)NH—; —C(O)O-Pyridoxine-; and —C(O)O-Phloroglucinol-.

In another set of embodiments, the monomer of complementary functionality may be a further monomer of formula (I). In such embodiments at least two monomers of formula (IV) may react together, provided the monomers of formula (I) have complementary terminal functionality.

In some embodiments monomers of formula (I) having complementary terminal functionality may be homofunctional. That is, each of the co-monomers may comprise one type of terminal functional group. The terminal functional groups of the co-monomers would be complementary and capable of reacting with one another to form a triazole moiety. For example, one co-monomer of formula (II) may comprise a terminal functional group comprising an alkyne functionality while the other co-monomer of formula (II) comprises a terminal functional group comprising an azide functionality. These co-monomers would be able to copolymerise under appropriate conditions to form a polymer conjugate having triazole moieties in the polymer backbone.

Examples of complementary monomers of formula (I) that are capable of copolymerizing to form a polymer-drug conjugate include a monomer of formula (I) where each group X is alkyne and a monomer of formula (I) wherein each group X is azide.

The monomers of formula (I) and (III) may react with one another in a mole ratio of 1:1.

The co-monomer for reaction with the drug-monomer conjugate is of formula III $$J\text{-}(Y^1\text{-}A)_n \qquad \text{(III)}$$

J represents a linking functional group, n is 2 to 8, preferably 3 to 8;

$Y^1$ comprises a polyether of formula $(OR^a)_m$ wherein $R^a$ is independently ethylene, propylene and butylene and m is from 1 to 300 (preferably 2 to 300) and the polyether is in chain with one or more groups which are preferably selected from one or more of optionally substituted straight or branched $C_1$ to $C_{10}$ alkylene, amino, ether, ester, amide, carbonate and carbamate;

A may be the same or different at each occurrence and represents a group comprising a terminal functional group comprising an alkyne or an azide functionality, wherein said terminal functional group is complementary to the terminal functional group X of formula (I) providing triazole moieties from reaction of X and A.

In the monomer of formula (III), A represents a group comprising a terminal functional group comprising an alkyne or an azide functionality. The azide or alkyne functionality present in terminal functional group of moiety "A" is complementary to the azide or alkyne functionality present in the terminal functional group of X in formula (I), such that upon reaction of the functional groups in A and X under click reaction conditions, a triazole moiety is formed.

In the monomer of formula (III) n is an integer and is at least 2. In some embodiments, n is an integer selected from the group consisting of 2, 3, 4, 5, 6, 7 and 8. Generally the network form of the copolymer is of particular advantage, in which case n is an integer from 3 to 8.

When n is 3 or more, the monomer of formula (III) is multifunctional and comprises 3 or more A moieties. In such embodiments, the monomer of formula (III) is a branched monomer. Monomers of formula (III) comprising at least three terminal functional groups provide branched or network architectures for the polymer conjugates of the invention.

As used herein, the term "group comprising a terminal functional group" encompasses embodiments where the group represents the terminal functional group per se, as well as embodiments where the terminal functional group is part of a larger chemical group.

The moiety "J" in formula (III) represents an optionally substituted linker group. In some embodiments J may be a divalent group. Alternatively, J may be multivalent and be a branched group. When a monomer of formula (I) and (III) copolymerise, J forms a linker segment in the polymer backbone of the conjugate.

In some embodiments, J may comprise a linker moiety selected from the group consisting of optionally substituted linear or branched aliphatic hydrocarbon, optionally substituted carbocyclyl, optionally substituted heterocyclyl, optionally substituted aryl, optionally substituted heteroaryl, an optionally substituted polymeric segment, and combinations thereof.

Optionally substituted linear or branched aliphatic hydrocarbon linker moieties may be selected from optionally substituted $C_1$ to $C_{20}$, $C_1$ to $C_{10}$ or $C_1$ to $C_6$ linear or branched aliphatic hydrocarbons. The aliphatic hydrocarbons may be saturated or unsaturated hydrocarbon.

Optionally substituted carbocyclyl linker moieties may have from 3 to 12, 3 to 8 or 5 to 6 carbon ring members.

Optionally substituted heterocyclyl linker moieties may have from 3 to 12, 3 to 8 or 5 to 6 ring members and 1, 2, 3, 4 or more heteroatoms as a part of the ring. The heteroatoms may be independently selected from the group consisting of O, N and S.

Optionally substituted aryl linker moieties may have from 3 to 12, 3 to 8 or 5 to 6 carbon ring members and at least one unsaturation.

Optionally substituted heteroaryl linker moieties may have from 3 to 12, 3 to 8 or 5 to 6 ring members and 1, 2, 3, 4 or more heteroatoms as a part of the ring. The heteroatoms may be independently selected from the group consisting of O, N and S. The heteroaryl linker moiety also has at least one unsaturation.

Exemplary polyethers include polymers of $C_2$ to $C_4$ alkylene diols, such as polyethylene glycol and polypropylene glycol, preferably polyethylene glycol.

Exemplary polyesters include polycaprolactone, poly(lactic acid), poly(glycolic acid) and poly(lactic-co-glycolic acid).

In one form, the polymeric linker moiety may comprise a biodegradable polymer. In general, biodegradable polymers comprise at least one biodegradable moiety.

Optionally substituted polymeric linker moieties may be of any suitable molecular weight, and the desired molecular weight may depend on the type of polymer and its properties. In some embodiments, J comprises a polymeric moiety having a molecular weight of not more than 1500.

In one set of embodiments, J comprises a polyether linker moiety derived from polyethylene glycol (PEG). The polyether segment may be derived from a PEG of suitable molecular weight. In some embodiments, the PEG has a molecular weight in the range of from about 200 to 10,000, preferably from about 200 to about 3000.

Typically J is selected from the group consisting of optionally substituted linear or branched aliphatic hydrocarbon, In one set of embodiments, J comprises a linker moiety derived from lysine, including the ethyl ester of lysine such as ethyl-2,6-bis(((3-azidopropoxy)carbonyl)amino)hexanoate ($ELDN_3$) the di(1-pentynol)urethane of the ethyl ester of lysine and the di(1-pentynol)urethane of the 1-pentynol ester of lysine.

In some embodiments, the group “J” in the formula (III) may comprise a functional group. The functional group may be selected from the group consisting of an amide, ether, ester, urethane, urea, and carbonate ester functional group. Such functional groups will generally be cleavable functional groups, which can degrade in a biological environment.

In a preferred embodiment the co-monomer is of formula III is of formula (IIIa)

$$J\text{-}((OR^a)_m\text{—}B\text{-}A)_n \quad \text{(IIIa)}$$

wherein

A may be the same or different at each occurrence and represents a group comprising a terminal functional group comprising an alkyne or an azide functionality, wherein the alkyne or azide functionality in the terminal functional group is complementary to the alkyne or azide functionality in a terminal functional group X present on a monomer of formula (I);

J represents a bond, oxygen or linking functional group, $R^a$ is selected from ethylene, propylene, butylene and mixtures thereof;

m is 1 to 300;

n is 3 to 8;

B is a bond, oxygen, the group of formula -MOC(O)N(H)M'-, -MOC(O)OM'- -MC(O)NHM'-, the group formula selected from (VIa), (VIb), (VIc) and (VId):

(VIa)

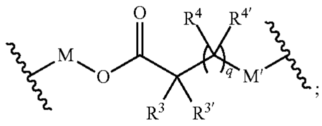

;

(VIb)

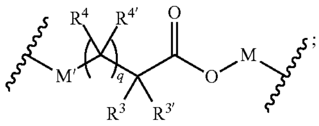

;

(VIc)

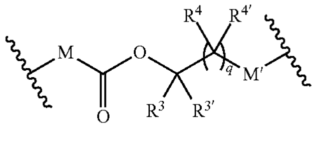

or (VIc)

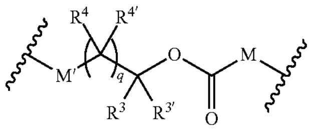

wherein M and M' are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and wherein in the monomers of formula, (VIa), (VIb), (VIc) and (VId) the groups $R^3$, $R^{3'}$, $R^4$ and $R^{4'}$ are independently selected from the group consisting of hydrogen, alkyl, alkoxy, alkoxy-alkyl, amino, alkyl amino, dialkylamino, amino-alkyl, alkylamino-alkyl, dialkylamino-alkyl wherein one of the pairs of $R^3$, $R^{3'}$, $R^4$, $R^{4'}$, may between the members of the pair form a carbocycle or heterocycle of 3 to 6 constituent ring members wherein the heterocycle may comprise from 1 to 3 constituent heteroatom ring members selected from oxygen and nitrogen which nitrogen may optionally be substituted by $C_1$ to $C_6$ alkyl.

In one set of embodiments the comonomer of formula (III) is of formula (IIIa)

$$J\text{-}((OR^a)_m\text{—}B\text{-}A)_n \quad \text{(IIIa)}$$

wherein

J is selected from an optionally substituted hydrocarbon or hydrocarbon ether or polyether of from 2 to 4 hydrocarbon units in each ether unit;

$R^a$ at each occurrence may be ethylene, propylene or butylene;

m is from 1 to 300, such as 1 to 100 or 1 to 50;

n is from 2 to 8 (preferably 2 to 4 such as 3 or 4);

B is a bond, oxygen, the group of formula -MOC(O)N(H)M'- or the group formula (IV)

(VIa)

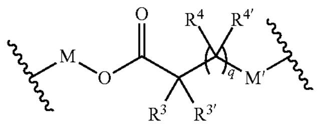

wherein

M and M' are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and wherein in the monomers of formula (III) and (IIIa) the groups $R^3$, $R^{3'}$, $R^4$ and $R^{4'}$ are independently selected from the group consisting of hydrogen, alkyl, alkoxy and alkoxyalkyl and wherein one of the pairs of $R^3$, $R^{3'}$, $R^4$, $R^{4'}$, may between the members of the pair form a carbocycle or heterocycle of 3 to 6 constituent ring members wherein the heterocycle may comprise from 1 to 3 constituent oxygen heteroatom ring members.

In a preferred embodiment of the co-monomer of formula (III) the integer n is at least three, such as from 3 to 8 and most preferably is 3 or 4. In this embodiment the resulting co-monomer has 3 or more arms with reactive terminal group resulting in reaction with the drug-monomer of formula II to form a polymer network comprising pendent drug moieties covalently linked to the network of polymer backbone.

The moiety of formula (VIa) may be of either orientation with respect to $(OR^a)_m$ and A.

In some embodiments, specifically when n is 3 to 8 in the monomer of formula (I), Q is present and each Q-X is independently selected from the following group:

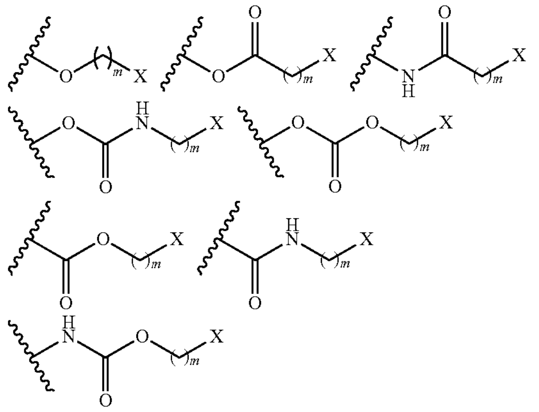

where m is from 0 to 10, preferably 0 to 6.

As described above specific example of the preferred group Q including in the monomer of formula (I) and the polymer segment of formula include:

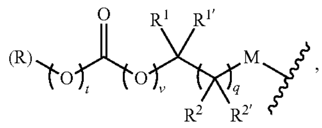,

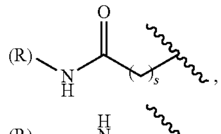, 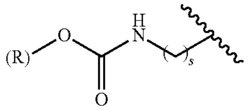,

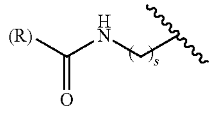 and 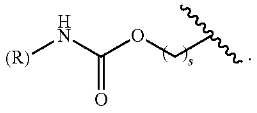.

wherein (R) indicates the end of the group attached to the group R and the opposite end is attached to (X);

each of t and v are independently 0 or 1 and at least one of t and v is 1 (preferably one of t and v is 1 and the other is 0);

$R^1$, $R^{1'}$, $R^2$ and $R^{2'}$ are independently selected from the group consisting of hydrogen, alkyl, alkoxy and alkoxyalkyl, and wherein one of the pairs of $R^1$, $R^1$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and s is from 0 to 10 preferably from 0 to 6.

Specific preferred examples of Q of this type include:

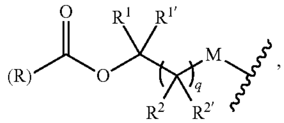,

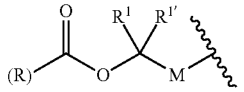 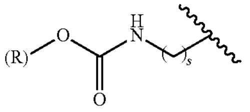

and

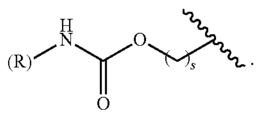.

When a monomer-drug conjugate having a linking group Q is used to prepare polymer conjugates of the invention, the linking group Q becomes incorporated into the polymer backbone. Thus any linking moieties and functional groups present in Q become part of the backbone of the polymer conjugate.

When Q comprises a functional group such as an amide, ether, ester, urethane, urea, and carbonate ester functional group, such functional groups will generally be cleavable functional groups and can provide points for erosion or degradation in the polymer backbone when a monomer-bioactive agent conjugate comprising such groups is used to form the polymer conjugate. The presence of cleavable groups derived from the functional groups in the polymer backbone can facilitate breakdown of the polymer conjugate, allowing formation of lower molecular weight polymer fragments.

In a preferred set of embodiments the drug-polymer conjugate which is a co-polymer of a drug conjugate monomer of formula (IV)

(IV)

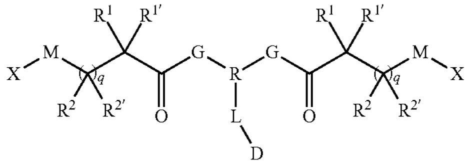

wherein

G is independently selected from oxygen and $NR^{16}$ where $R^{16}$ is hydrogen or $C_1$ to $C_4$ alkyl;

M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1;

X is a terminal functional group comprising an alkyne or an azide;

R is selected from the group consisting of linear or branched hydrocarbon, optionally substituted aryl and optionally substituted heteroaryl;

L is a linker group; and

D is a releasable bicyclic prostaglandin drug; and a co-monomer of Formula (IIIa)

$$J\text{-}((OR^a)_m\text{—}B\text{-}A)_n \quad \text{(IIIa)}$$

J is selected from an optionally substituted hydrocarbon or hydrocarbon ether or polyether of from 2 to 4 hydrocarbon units;

$R^a$ at each occurrence may be ethylene, propylene or butylene;

m is from 1 to 300;

n is from 3 to 8 (preferably 3 or 4);

B is a bond, oxygen, the group of formula -MOC(O)N(H)M'- or the group formula (VIa)

(VIa)

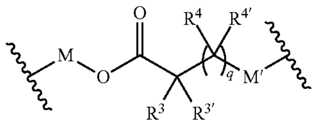

wherein

M and M' are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and wherein in the monomers of formula (I) and (IIIa) the groups $R^1$, $R^{1'}$, $R^2$, $R^{2'}$, $R^3$, $R^{3'}$, $R^4$ and $R^{4'}$ are independently selected from the group consisting of hydrogen, alkyl, alkoxy, alkoxy-alkyl and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and one of the pairs of $R^3$, $R^{3'}$ and $R^4$, $R^{4'}$, may between the members of the pair form a carbocycle or heterocycle of 3 to 6 constituent ring members wherein the heterocycle may comprise from 1 to 3 constituent oxygen heteroatom ring members 1.

In preferred embodiments the group B is of formula (IVa) or (IVb):

(VIa)

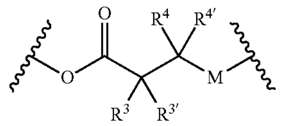

or (VIb)

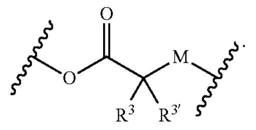

In this embodiment the co-monomer is branched and results in a network copolymer which we have found to provide a significant advantage in control of biodegradation.

Accordingly the invention further provides a drug-polymer conjugate, which is a hyperbranched polymer network comprising network segments of formula (XXX):

XXX

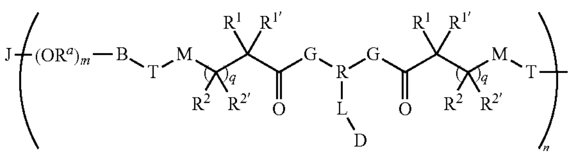

wherein groups J, R, B, $R^a$, T, M, R, G, L and D and m and q are as hereinbefore defined for formulae (II) and (IIIa) and n is an integer of from 3 to 8 and preferably 3 or 4.

In one set of embodiments of formula (IIIa) and (XXX) the integer n is 3 to 8 and the branched linker J is a hydrocarbon of formula:

$$C_z H_{2z+2-n}$$

wherein z is from 1 to 8, preferably 3 to 8 and n is from 3 to 8 and preferably 3 or 4.

Specific examples of the linker J where n is 3 to 8 include:

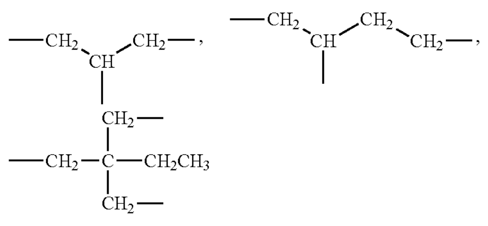

wherein n is 3; and

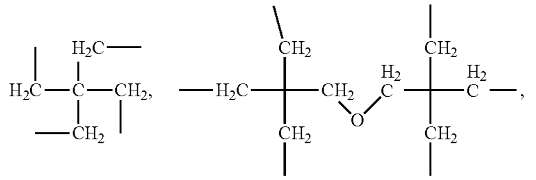

-continued

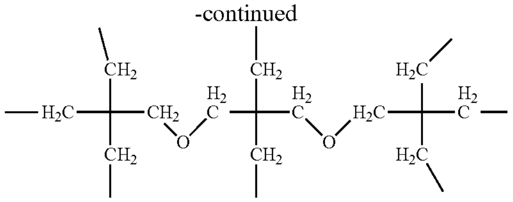

wherein n is from 4, 6 or 8.

In the formula IIIc the group $(OR^a)_m$ is a polymer of one or more of ethylene oxide, propylene oxide and butylene oxide.

In one set of embodiments the formula $(OR^a)_m$ in formula (III) or formula (XXX) is selected from poly(ethylene oxide), poly(propylene oxide), poly(butylene oxide), block copolymers of one or more of poly(ethylene oxide), poly (propylene oxide) and poly(butylene oxide), block copolymers of two or more of poly(ethylene oxide), poly(propylene oxide) and poly(butylene oxide), wherein $(OR^a)_m$ has a molecular weight in the range of from 200 to 10,000.

Specific examples of the comonomer of formula (IIIa) include:

(IIIa-1)

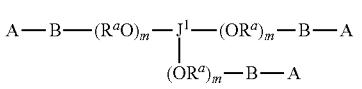

wherein $J^1$ is of formula $C_zH_{Zz-1}$ (straight or branched chain) and wherein z is an integer from 1 to 8, preferably 3 to 8; and (IIIa-2)

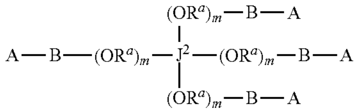

wherein $J^2$ is of formula $C_zH_{2z-2}$ (straight or branched chain) and wherein z is an integer from 1 to 8, preferably 3 to 8 such as 5.

In formulae (I), (II), (IIa), (IIb), (IIc), (IId) (IIIa), (IIIa-1), (IIIa-2), (IV), (IVa), (IVb), and (XXX) some or all of the substituents $R^1$, $R^{1'}$, $R^2$, $R^{2'}$, $R^3$, $R^{3'}$, $R^4$ and $R^{4'}$ are present.

The substituents $R^1$, $R^{1'}$, $R^2$, $R^{2'}$, $R^3$, $R^{3'}$, $R^4$ and $R^{4'}$ independently selected from the group consisting of hydrogen, alkyl, alkoxy and alkoxyalkyl and wherein one of the pairs of $R^1$, $R^1$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and wherein one of the pairs of $R^3$, $R^{3'}$, $R^4$, $R^{4'}$, may between the members of the pair form a carbocycle or heterocycle of 3 to 6 constituent ring members wherein the heterocycle may comprise from 1 to 3 constituent oxygen heteroatom ring members.

It is particularly preferred that at least one of the substituents on the carbon atom in a position alpha or beta to the carbonyl carbon, that is at least one of $R^1$, $R^{1'}$, $R^2$, $R^{2'}$, $R^3$, $R^{3'}$, $R^4$ and $R^{4'}$ (present in each of the compounds) is other than hydrogen.

The substituents other than hydrogen significantly improve the control of biodegradation of the backbone. The control allows the backbone of the drug-polymer conjugate to be degraded and any remaining drug active to be systemically diluted in the subject. The biodegradation allows the treatment term of the subject to be predetermined. This limitation on treatment term and biodegradation of the backbone are particularly advantageous in embodiments in which the drug polymer conjugate is used in localised treatment of tissue such as in the case of use of the drug-polymer conjugate in the form of an implant in treatment, for example of glaucoma.

In some embodiments at least one of $R^1$ and $R^{1'}$ is other than hydrogen and in further embodiments at least one of $R^2$ and $R^{2'}$ is other than hydrogen.

In embodiments of the invention where the monomer of formula (IIIa) and at least one of the segments of formula (VIa), (VIb), (VIc) (VId) is present, then substituents $R^3$, $R^{3'}$, $R^4$, $R^{4'}$ may be hydrogen where at least one of $R^1$, $R^{1'}$, $R^2$ and $R^{2'}$ are other than hydrogen or where $R^1$, $R^{1'}$, $R^2$ and $R^{2'}$ are hydrogen the control of biodegradation is significantly improved where at least one of $R^3$, $R^{3'}$, $R^4$ and $R^{4'}$ is other than hydrogen. In one set of embodiments at least one of $R^1$, $R^{1'}$, $R^2$ and $R^{2'}$ is other than hydrogen and at least one of $R^3$, $R^{3'}$, $R^4$, $R^{4'}$ is other than hydrogen.

It is generally preferred in order to enhance control of degradation that at least one of the groups on the carbon alpha to the carbonyl, that is $R^1$, $R^{1'}$, $R^3$ and $R^{3'}$, are other than hydrogen.

When one or more of $R^1$, $R^{1'}$, $R^2$, $R^{2'}$, $R^3$, $R^{3'}$, $R^4$ and $R^{4'}$ are other than hydrogen specific examples of the substituents other than hydrogen may be selected from the group selected from $C_1$ to $C_4$ alkyl such as methyl, ethyl, propyl, isopropyl, butyl, isobutyl, sec-butyl, and tert-butyl, $C_1$ to $C_4$ alkoxy such as methoxy, ethoxy, propyl, isopropoxy, butoxy, isobutoxy, sec-butoxy, and tert-butoxy; and $C_1$ to $C_4$ alkoxy substituted $C_1$ to $C_4$ alkyl such as one of the above $C_1$ to $C_4$ alkoxy examples substituted with one of the above $C_1$ to $C_4$ alkyl examples. Biodegradation may be enhanced by gemal-substitution with groups other than hydrogen. In cases where the carbon atom alpha or beta to the carbonyl carbon are di-substituted specific examples of the di-substitution pair may be selected from $C_1$ to $C_4$ alkyl such as methyl, ethyl, propyl, isopropyl, butyl, isobutyl, sec-butyl, and tert-butyl, $C_1$ to $C_4$ alkoxy such as methoxy, ethoxy, propyl, isopropoxy, butoxy, isobutoxy, sec-butoxy, and tert-butoxy; and $C_1$ to $C_4$ alkoxy substituted $C_1$ to $C_4$ alkyl such as one of the above $C_1$ to $C_4$ alkoxy examples substituted with one of the above $C_1$ to $C_4$ alkyl examples. Biodegradation is particularly enhanced where the carbon alpha to the carbonyl carbon is di-substituted, that is at least one or both of the pairs $R_1$, $R_{1'}$ and $R^3$, $R^{3'}$ are other than hydrogen.

The pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and wherein one of the pairs of $R^3$, $R^{3'}$, $R^4$, $R^{4'}$, may between the members of the pair form a carbocycle or heterocycle of 3 to 6 constituent ring members wherein the heterocycle may comprise from 1 to 3 constituent oxygen heteroatom ring members.

Specific examples of carbocycles of this type include groups where one or more of the pairs $R^1$, $R^{1'}$; $R^2$, $R^2$; $R^3$, $R^{3'}$ and; $R^4$, $R^{4'}$ between the pair form a spiro carbocycle via a linker selected from the group consisting of optionally substituted alkylene of from 2 to 5 methylene groups alkylene wherein the optional substituent is $C_1$ to $C_4$ alkyl or $C_1$ to $C_4$ alkoxy, and optionally substituted group of from 2 to 5 methylenes and from 1 to 3 oxygen heteroatoms wherein the optional substituents are $C_1$ to $C_4$ alkyl or $C_1$ to $C_4$ alkoxy.

Specific examples include the groups $—CH_2—CH_2—$, $—CH_2—CH_2—CH_2—CH_2—$, $—CH_2—CH_2—CH_2—CH_2—CH_2—$ and $—CH_2—CH_2—O—CH_2—CH_2—$.

In formulas (I), (II), (IV), (IVa), (IVb) and (V) linking groups M or M and M' are present in the backbone portion of the monomer or polymer. The groups M and M' are independently selected and occurrences of M in portions of the drug-monomer conjugate and co-monomer are also independently selected. The drug-monomer conjugate contains two M linking groups which may be independently selected but in many embodiments it is convenient that they are the same. The groups M and M' are each selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl. Preferred examples of embodiments where M and M' are $C_1$ to $C_{10}$ aliphatic include $—(CH_2)_y—$ where y is from 1 to 6, preferably 1 to 4 such as methylene or ethylene and wherein one or two hydrogens in the chain $—(CH_2)_y—$ may be substituted by methylene to form an alkene branch or $C_1$ to $C_4$ alkyl. In embodiments where one or both of M and M' are selected from —O ($C_1$ to $C_{10}$ straight or branched chain aliphatic) examples include $—O—(CH_2)_y—$ where y is from 1 to 6, preferably 1 to 4 such as methylene or ethylene. In embodiments where one or both of M and M' are selected from ether linking group comprising $C_1$ to $C_{10}$ straight or branched chain aliphatic interrupted by a oxygen (—O—) examples include the group (CH2)-O—(CH2)y where y is from 1 to 6, preferably 1 to 4 such as methylene or ethylene. In embodiments where M and/or M' are the group —N($R^w$)—($C_1$ to $C_{10}$ straight or branched chain aliphatic) and an ether linking group comprising $C_1$ to $C_{10}$ straight or branched chain aliphatic interrupted by the group N($R^w$) wherein $R^w$ is selected from hydrogen and $C_1$ to $C_4$ alkyl examples include —N($R^w$)—$(CH2)_y$— where y is from 1 to 6, preferably 1 to 4 such as methylene or ethylene. In embodiments where one or both of M and M' are selected from amine linking group comprising $C_1$ to $C_{10}$ straight or branched chain aliphatic interrupted by a oxygen (—O—) examples include the group (CH2)-N($R^w$)—(CH2)y where y is from 1 to 6, preferably 1 to 4 such as methylene or ethylene.

Specific examples of monomers of formula (I) comprising one or more groups $R^1$, $R^{1'}$; $R^2$, $R^{2'}$ other than hydrogen include the following:

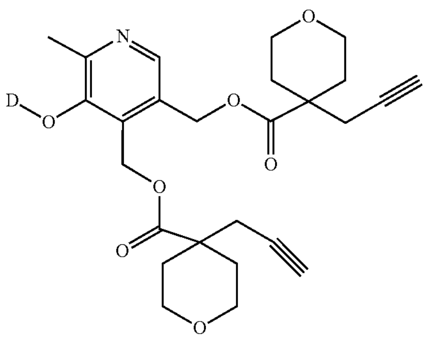

-continued

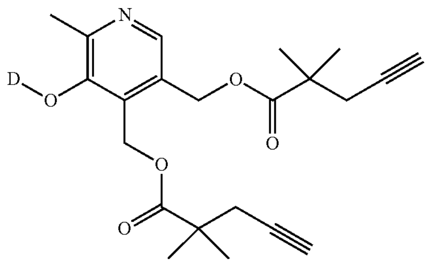

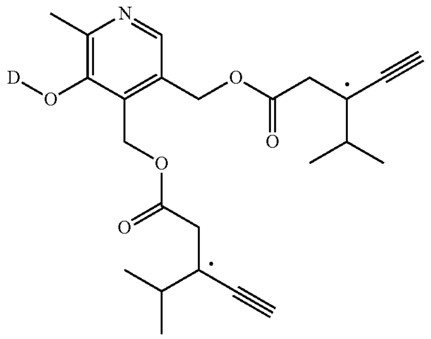

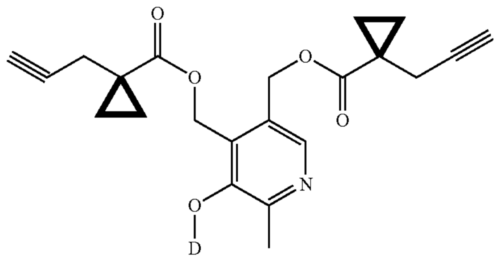

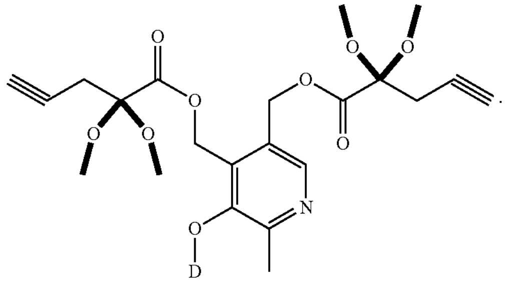

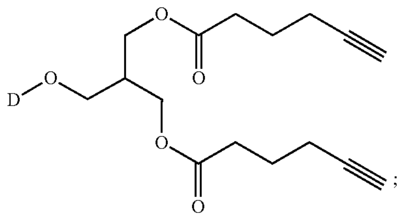

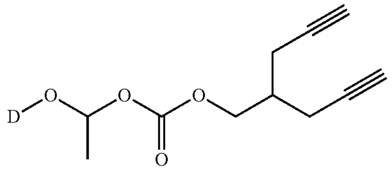

-continued

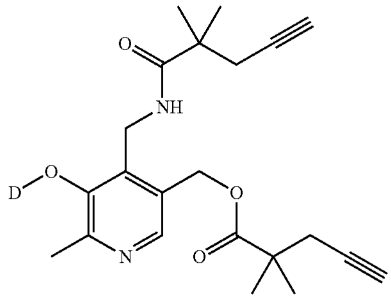

; and

-continued

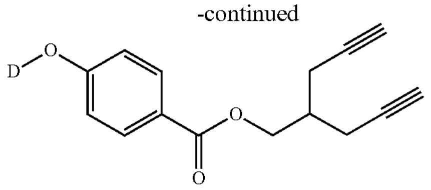

where D is the acid residue of a drug such as selected from the group consisting of the acid residue of a bicyclic prostaglandin such as those of formula X, Xa or the specific bicyclic prostaglandins of Table 1.

Examples of hyperbranched polymer networks include compounds of the following formula where the terminal crosses represent branching moieties provided by co-monomers of formula (IIIa-2):

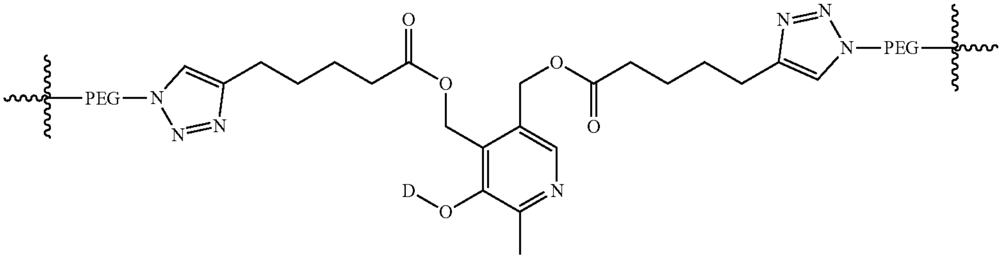

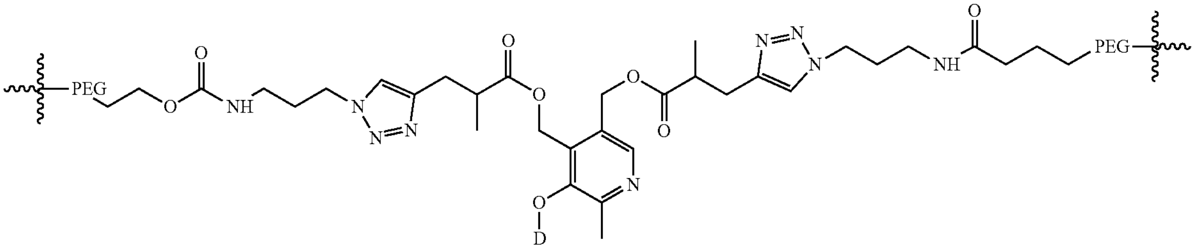

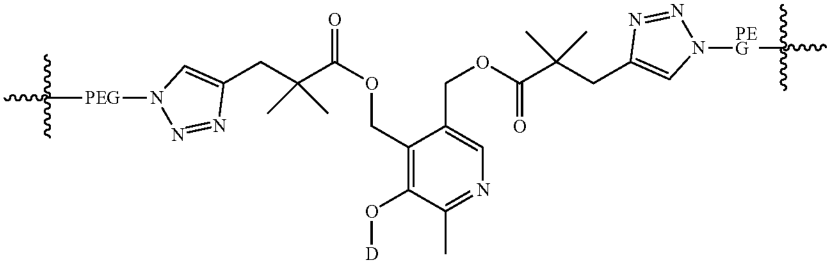

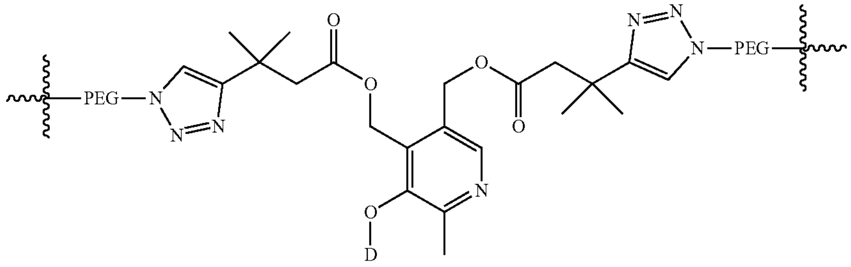

-continued

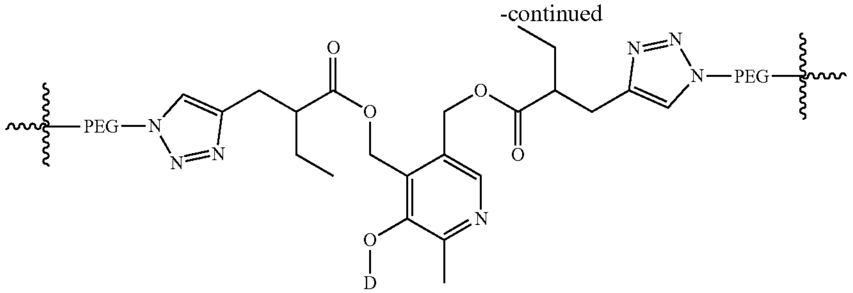

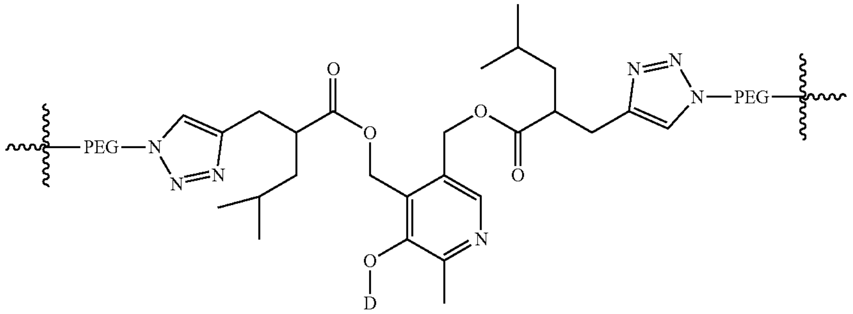

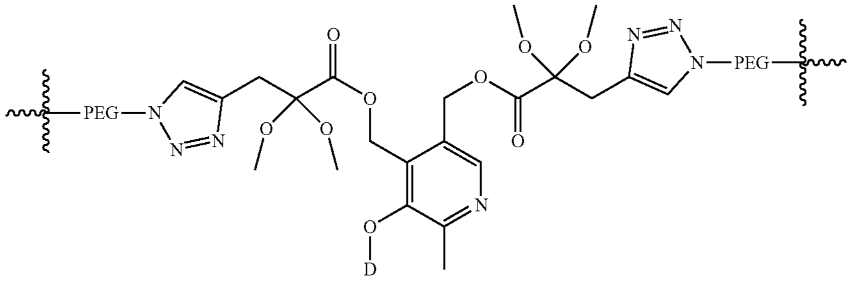

and wherein D is the acid residue of a drug such as selected from bicyclic prostaglandins.

In a number of embodiments of formulae (IIa), (IIb), (IIc) and (IId) s is from 0 to 6 (preferably 0 to 2). The number s in some examples may be 0, 1 or 2.

According to one embodiment there is provided a method of delivering a drug to a subject, the method comprising administering to the subject a drug-polymer conjugate in accordance with the invention.

By the polymer conjugate being "suitable" for administration to a subject is meant that administration of the conjugate to a subject will not result in unacceptable toxicity, including allergenic responses and disease states. By the term "subject" is meant either an animal or human subject.

By "administration" of the conjugate to a subject is meant that the composition is transferred to the subject such that the drug will be released. The drug-polymer conjugate comprising prostaglandins and optionally also β-blockers in monomeric units derived from mixtures of monomer conjugates thereof, may be used in the treatment of eye disorders associated with increased intraocular pressure, such as glaucoma, it is preferred that the polymer conjugate is administered to an affected eye of a subject. Administration to the eye may be by way of intracameral to either the anterior or posterior chamber, intravitreal, subchoroidal or subconjunctival administration.

The polymer conjugates may be provided in particulate form and blended with a pharmacologically acceptable carrier to facilitate administration. By "pharmacologically acceptable" is meant that the carrier is suitable for administration to a subject in its own right. In other words, administration of the carrier to a subject will not result in unacceptable toxicity, including allergenic responses and disease states. The term "carrier" refers to the vehicle with which the conjugate is contained prior to being administered.

As a guide only, a person skilled in the art may consider "pharmacologically acceptable" as an entity approved by a regulatory agency of a federal or state government or listed in the US Pharmacopeia or other generally recognised pharmacopeia for use in animals, and more particularly humans. Suitable pharmacologically acceptable carriers are described in Martin, Remington's Pharmaceutical Sciences, 18th Ed., Mack Publishing Co., Easton, PA, (1990).

The polymer drug conjugates may also form part of or be formed into an article or device, or be applied as a coating on an article or device, and implanted in a subject. By being "implanted" is meant that the article or device is totally or partly introduced medically into a subject's body and which is intended to remain there after the procedure.

Suitable dosage amounts of the drug and dosing regimens of the polymer conjugates can be determined by a physician and may depend on the particular condition being treated, the rate of release of the form the polymer backbone, the severity of the condition as well the general age, health and weight of the subject.

The form of the drug-polymer conjugate may be adjusted to be suited to the required application such as a coating, film, pellet, capsule, fibres, laminate, foam etc. The difference in the form of the conjugate provides a means to alter the release profile of the drug. For example the amount of polymer and drug may be the same in two different structures however the differences in the surface area to volume, rates of hydration and diffusion paths from the different physical forms or structures can result in different rates of drug release from essentially the same polymer.

The adjustment of the form of the polymer conjugate to suit the application and further to adjust the form to further control drug release provides an additional advantage over purely compositional and polymer structural means to control the release profile of the drug.

Some of the compositional/structural means to control the release of the drug include: controlling the loading of the drug; composition of the other co-monomers to adjust criteria such as hydrophobicity, flexibility, susceptibility to degradation, ability of the fragments to autocatalyse the polymer degradation, thermal stability of the polymer, mouldability, polymer solubility to assist casting etc.

In one set of embodiments, the drug may be released from the polymer conjugate such that it provides for a sustained drug delivery system. Such a delivery system may in its simplest form be the polymer conjugate provided in a desired shape, for example a pellet or more intricate shape. To promote surface area contact of the polymer conjugate under physiological conditions or with a biological environment, it may also be provided in the form of a foamed product or a coating on substrate.

By "sustained drug moiety delivery" is meant that the drug is released from the conjugate over a period of time, for example over a period of 10 or more minutes, 30 or more minutes, 60 or more minutes, 2 or more hours, 4 or more hours, 12 or more hours, 24 or more hours, 2 or more days, 5 or more days, 10 or more days, 30 or more days, 2 or more months, 4 or more months or over 6 or more months.

Drug-polymer conjugates of the present invention may be incorporated into drug delivery systems, therapeutic articles, devices or preparations, and pharmaceutical products for the treatment of ocular hypertension.

The drug-polymer conjugates of the present invention may be blended with one or more other polymers (for example, biodegradable polymers).

Drug-polymer conjugates in accordance with the invention can be formed into an article or device. The article or device may be fabricated in a range of forms. Suitably, the article or device is a medical device, preferably an ocular implant. The polymer conjugates in accordance with the invention can also be incorporated or made into coatings for target in vitro and in vivo applications.

The drug-polymer conjugates in accordance with the invention can be formed into an article or device that is suitable for administration to the eye.

In some embodiments, a drug-polymer conjugate may be in the form of a solid article (such as a particle, rod, sphere or pellet), a semi-solid, a deformable solid, a gel, or a liquid, for placement in the eye of the subject.

In another aspect, the present invention provides an ocular implant for the treatment of glaucoma comprising a drug-polymer conjugate of any one of the embodiments described herein.

In another aspect, the present invention provides an ocular implant for the treatment or prevention of endophthalmitis or ocular inflammation glaucoma comprising a drug-polymer conjugate of any one of the embodiments described herein.

In one form, the implant is a rod-shaped or sphere-shaped and is able to be housed within the lumen of a needle, such as a 20 to 23 gauge needle. The outer diameter of the implant would be less than 0.5 mm, preferably about 0.4 mm and more preferably 0.3 mm. The length of the rod-shaped implant can be selected to deliver the required dose of drug.

The implant can be of a number of different structural forms. The ocular implant could be a solid, a semi-solid or even a gel. A solid implant would comprise material with a glass transition temperature (as measured by differential scanning calorimetry) above 37° C., a semi-solid would have a glass transition temperature at or just below 25-37° C. A gel could be formed by appropriate formulation of the polymer conjugate with an appropriate plasticiser. In one set of embodiments, the implant could be a hydrogel.

In yet another aspect the present invention provides an injectable article for placement in an eye of the subject, wherein the injectable article comprises a drug-polymer conjugate of any one of the embodiments described herein. In one form, the injectable article is an injectable gel.

It is contemplated that an ocular implant may be a bi-component polymer structure where the drug-polymer conjugate can either be incorporated in the outer or inner layers of the bi-component structure. Incorporating the drug-polymer conjugate in the outer layer could be done to give a measured dose. Additionally the inner polymer layer could be to provide structural integrity to allow the delivery via the needle. Additionally the inner polymer could be designed to degrade either faster or slower than the polymer conjugate layer. This could be to alter the rate of bioerosion or the implant.

Possible means for producing rod-shaped implants include:

- Melt extrusion of the drug-polymer conjugate or a material containing the drug-polymer conjugate through a shaped die.
- Simultaneous bi-component extrusion of the drug-polymer conjugate and other materials forming the outer or inner layers through an appropriate die.
- Sequential overcoating extrusion of one polymer later with another. For example a core polymer fibre of PLGA could be melt overcoated with a polymer containing the drug-polymer conjugate.
- It is also possible to solution coat an appropriate inner polymer carrier material (e.g. PLGA) with a solution containing the drug-polymer conjugate.

Possible means for producing rod-shaped or sphere-shaped implants include:

- Injection moulding of the drug-polymer conjugate or a material containing the drug-polymer conjugate.
- Solution casting in a mould of the drug-polymer conjugate or a material containing the drug-polymer conjugate.

In yet another aspect the present invention provides an injectable article for placement in an eye of the subject, wherein the injectable article comprises a drug-polymer conjugate of any one of the embodiments described herein. In one form, the injectable article is in the form of a gel.

In this specification "optionally substituted" is taken to mean that a group may or may not be substituted or fused (so as to form a condensed polycyclic group) with one, two, three or more of organic and inorganic groups (i.e. the optional substituent) including those selected from: alkyl, alkenyl, alkynyl, carbocyclyl, aryl, heterocyclyl, heteroaryl, acyl, aralkyl, alkaryl, alkheterocyclyl, alkheteroaryl, alkcarbocyclyl, halo, haloalkyl, haloalkenyl, haloalkynyl, haloaryl, halocarbocyclyl, haloheterocyclyl, haloheteroaryl, haloacyl, haloaryalkyl, hydroxy, hydroxyalkyl, hydroxyalkenyl, hydroxyalkynyl, hydroxycarbocyclyl, hydroxyaryl, hydroxyheterocyclyl, hydroxyheteroaryl, hydroxyacyl, hydroxyaralkyl, alkoxyalkyl, alkoxyalkenyl, alkoxyalkynyl, alkoxycarbocyclyl, alkoxyaryl, alkoxyheterocyclyl, alkoxyheteroaryl, alkoxyacyl, alkoxyaralkyl, alkoxy, alkenyloxy, alkynyloxy, aryloxy, carbocyclyloxy, aralkyloxy, heteroaryloxy, heterocyclyloxy, acyloxy, haloalkoxy, haloalkenyloxy, haloalkynyloxy, haloaryloxy, halocarbocyclyloxy, haloaralkyloxy, haloheteroaryloxy, haloheterocyclyloxy, haloacyloxy, nitro, nitroalkyl, nitroalkenyl, nitroalkynyl, nitroaryl, nitroheterocyclyl, nitroheteroayl, nitrocarbocyclyl, nitroacyl, nitroaralkyl, amino ($NH_2$), alkylamino, dialkylamino, alkenylamino, alkynylamino, arylamino, diarylamino, aralkylamino, diaralkylamino, acylamino, diacylamino, heterocyclamino, heteroarylamino, carboxy, carboxyester, amido, alkylsulphonyloxy, arylsulphenyloxy, alkylsulphenyl, arylsulphenyl, thio, alkylthio, alkenylthio, alkynylthio, arylthio, aralkylthio, carbocyclylthio, heterocyclylthio, heteroarylthio, acylthio, sulfoxide, sulfonyl, sulfonamide, aminoalkyl, aminoalkenyl, aminoalkynyl, aminocarbocyclyl, aminoaryl, aminoheterocyclyl, aminoheteroaryl, aminoacyl, aminoaralkyl, thioalkyl, thioalkenyl, thioalkynyl, thiocarbocyclyl, thioaryl, thioheterocyclyl, thioheteroaryl, thioacyl, thioaralkyl, carboxyalkyl, carboxyalkenyl, carboxyalkynyl, carboxycarbocyclyl, carboxyaryl, carboxyheterocyclyl, carboxyheteroaryl, carboxyacyl, carboxyaralkyl, carboxyesteralkyl, carboxyesteralkenyl, carboxyesteralkynyl, carboxyestercarbocyclyl, carboxyesteraryl, carboxyesterheterocyclyl, carboxyesterheteroaryl, carboxyesteracyl, carboxyesteraralkyl, amidoalkyl, amidoalkenyl, amidoalkynyl, amidocarbocyclyl, amidoaryl, amidoheterocyclyl, amidoheteroaryl, amidoacyl, amidoaralkyl, formylalkyl, formylalkenyl, formylalkynyl, formylcarbocyclyl, formylaryl, formylheterocyclyl, formylheteroaryl, formylacyl, formylaralkyl, acylalkyl, acylalkenyl, acylalkynyl, acylcarbocyclyl, acylaryl, acylheterocyclyl, acylheteroaryl, acylacyl, acylaralkyl, sulfoxidealkyl, sulfoxidealkenyl, sulfoxidealkynyl, sulfoxidecarbocyclyl, sulfoxidearyl, sulfoxideheterocyclyl, sulfoxideheteroaryl, sulfoxideacyl, sulfoxidearalkyl, sulfonylalkyl, sulfonylalkenyl, sulfonylalkynyl, sulfonylcarbocyclyl, sulfonylaryl, sulfonylheterocyclyl, sulfonylheteroaryl, sulfonylacyl, sulfonylaralkyl, sulfonamidoalkyl, sulfonamidoalkenyl, sulfonamidoalkynyl, sulfonamidocarbocyclyl, sulfonamidoaryl, sulfonamidoheterocyclyl, sulfonamidoheteroaryl, sulfonamidoacyl, sulfonamidoaralkyl, nitroalkyl, nitroalkenyl, nitroalkynyl, nitrocarbocyclyl, nitroaryl, nitroheterocyclyl, nitroheteroaryl, nitroacyl, nitroaralkyl, cyano, sulfate and phosphate groups.

Preferred optional substituents include the aforementioned reactive functional groups or moieties, polymer chains and alkyl, (e.g. $C_{1-6}$ alkyl such as methyl, ethyl, propyl, butyl, cyclopropyl, cyclobutyl, cyclopentyl or cyclohexyl), hydroxyalkyl (e.g. hydroxymethyl, hydroxyethyl, hydroxypropyl), alkoxyalkyl (e.g. methoxymethyl, methoxyethyl, methoxypropyl, ethoxymethyl, ethoxyethyl, ethoxypropyl etc.) alkoxy (e.g. $C_{1-6}$ alkoxy such as methoxy, ethoxy, propoxy, butoxy, cyclopropoxy, cyclobutoxy), halo, trifluoromethyl, trichloromethyl, tribromomethyl, hydroxy, phenyl (which itself may be further substituted e.g., by $C_{1-6}$ alkyl, halo, hydroxy, hydroxy$C_{1-6}$ alkyl, $C_{1-6}$ alkoxy, halo$C_{1-6}$alkyl, cyano, nitro $OC(O)C_{1-6}$ alkyl, and amino), benzyl (wherein benzyl itself may be further substituted e.g., by $C_{1-6}$ alkyl, halo, hydroxy, hydroxy$C_{1-6}$alkyl, $C_{1-6}$ alkoxy, halo$C_{1-6}$ alkyl, cyano, nitro $OC(O)C_{1-6}$ alkyl, and amino), phenoxy (wherein phenyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro $OC(O)C_{1-6}$ alkyl, and amino), benzyloxy (wherein benzyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro $OC(O)C_{1-6}$ alkyl, and amino), amino, alkylamino (e.g. $C_{1-6}$ alkyl, such as methylamino, ethylamino, propylamino etc), dialkylamino (e.g. $C_{1-6}$ alkyl, such as dimethylamino, diethylamino, dipropylamino), acylamino (e.g. $NHC(O)CH_3$), phenylamino (wherein phenyl itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro $OC(O)C_{1-6}$ alkyl, and amino), nitro, formyl, —C(O)-alkyl (e.g. $C_{1-6}$ alkyl, such as acetyl), 0-C(O)-alkyl (e.g. $C_{1-6}$alkyl, such as acetyloxy), benzoyl (wherein the phenyl group itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro $OC(O)C_{1-6}$alkyl, and amino), replacement of $CH_2$ with C═O, $CO_2H$, $CO_2$alkyl (e.g. $C_{1-6}$ alkyl such as methyl ester, ethyl ester, propyl ester, butyl ester), $CO_2$phenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro $OC(O)C_{1-6}$ alkyl, and amino), $CONH_2$, CONHphenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro $OC(O)C_{1-6}$ alkyl, and amino), CONHbenzyl (wherein benzyl itself may be further substituted e.g., by $C_{1-6}$ alkyl, halo, hydroxy hydroxyl $C_{1-6}$ alkyl, $C_{1-6}$ alkoxy, halo $C_{1-6}$ alkyl, cyano, nitro $OC(O)C_{1-6}$ alkyl, and amino), CONHalkyl (e.g. $C_{1-6}$ alkyl such as methyl amide, ethyl amide, propyl amide, butyl amide) CONHdialkyl (e.g. $C_{1-6}$ alkyl) aminoalkyl (e.g., HN $C_{1-6}$ alkyl-, $C_{1-6}$alkylHN—$C_{1-6}$ alkyl- and ($C_{1-6}$ alkyl)$_2$N—$C_{1-6}$ alkyl-), thioalkyl (e.g., HS $C_{1-6}$ alkyl-), carboxyalkyl (e.g., $HO_2CC_{1-6}$ alkyl-), carboxyesteralkyl (e.g., $C_{1-6}$ alkyl$O_2CC_{1-6}$ alkyl-), amidoalkyl (e.g., $H_2N(O)CC_{1-6}$ alkyl-, H($C_{1-6}$ alkyl)N(O)$CC_{1-6}$ alkyl-), formylalkyl (e.g., $OHCC_{1-6}$alkyl-), acylalkyl (e.g., $C_{1-6}$ alkyl(O)$CC_{1-6}$ alkyl-), nitroalkyl (e.g., $O_2NC_{1-6}$ alkyl-), sulfoxidealkyl (e.g., $R^3$(O)$SC_{1-6}$ alkyl, such as $C_{1-6}$ alkyl(O)$SC_{1-6}$ alkyl-), sulfonylalkyl (e.g., $R^3(O)_2SC_{1-6}$ alkyl- such as $C_{1-6}$ alkyl$(O)_2SC_{1-6}$ alkyl-), sulfonamidoalkyl (e.g., 2HRN(O)$SC_{1-6}$ alkyl, H($C_{1-6}$ alkyl)N(O)$SC_{1-6}$ alkyl-).

The ring 1 and ring 2 groups may each represent independently a $C_3$-10 carbocycle or a 3- to 10-membered heterocycle, optionally substituted with 1 to 5 substituents. Examples of preferred substituents for the ring 1 and ring 2 groups may be selected from the group consisting of halo, $CF_3$, $OCF_3$, $C_{1-4}$ alkoxy, $C_{1-4}$ alkyl group, hydroxy and nitrile, m in the $(CH_2)_m$ portion of the bicyclic prostaglandin is preferably an integer of 1 to 10, preferably 1 to 6, more preferably 2 to 4, n in the group $-(CH2)_n-CH=CH-$ represents an integer of 1 to 6, preferably 1 to 4 and more preferably 1 or 2 and p in the group $-(CH_2)_p-A-CH_2-$ represents an integer of 1 to 4.

In the present invention, the groups halogen or halo means fluorine, chlorine, bromine, and iodine. Typically fluorine and chlorine are preferred.

In the present invention, ring 1 and/or ring 2 may be a carbocycle. The carbocycle may be a $C_{3-10}$ monocyclic or bicyclic carbocycle, a part or all of which may be saturated, and examples include cyclopropane, cyclobutane, cyclopentane, cyclohexane, cycloheptane, cyclooctane, cyclononane, cyclodecane, cyclopentene, cyclohexne, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, perhydroindane, naphthalene, dihydronaphthalene, tetrahydronaphthalene, perhydronaphthalene etc. Preferred examples of carbocycle are the $C_{3-7}$ carbocycle means a $C_{1-7}$ monocyclic carbocycle, a part or all of which may be saturated, and examples include cyclopropane, cyclobutane, cyclopentane, cyclohexane, cycloheptane, cyclopentene, cyclohexene, cycloheptene, cyclopentadiene, cyclohexadiene, cycloheptadiene, benzene, etc.

In the present invention, the 3- to 10-membered heterocycle means a 3- to 10-membered monocyclic or bicyclic heterocycle, a part or all of which may be saturated, comprising 1 to 5 hetero atoms selected from an oxygen atom, a nitrogen atom and a sulfur atom, and examples include pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isooxazole, thiazole, isothiazole, furazan, oxadiazole, oxazine, oxadiazine, oxazepine, oxadiazepine, thiadiazole, thiazine, thiadiazine, thiazepine, thiadiazepine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisooxazole, tetrahydroisooxazole (isooxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, pyrrolopyridine, benzoxazole, benzothiazole, benzimidazole, chromene, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, tetrahydropyrrolopyridine, dihydrocinnoline, tetrahydrocinnoline, perhydrocinnnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, and perhydrobenzimidazole.

The more preferred example of ring 1, when present are benzene or a thiazole rings.

The more preferred examples of ring 2, benzene or cyclohexane substituted by 1 to 3 substituents selected from the group consisting of $C_{1-4}$ alkyl, $C_{1-4}$ alkoxy, $CF_3$, $OCF_3$ and halo and more preferably selected from $C_{1-4}$ alkyl, $CF_3$, $OCF_3$ and halo. Preferred halo are chloro and fluoro and particularly fluoro.

It is understood that the compounds of the present invention (including monomers and polymers) may exist in one or more stereoisomeric forms (e.g. enantiomers, diastereomers). The present invention includes within its scope all of these stereoisomeric forms either isolated (in for example enantiomeric isolation), or in combination (including racemic mixtures).

The following Examples are intended to illustrate the scope of the invention and to enable reproduction and comparison. They are not intended to limit the scope of the disclosure in any way.

EXAMPLES

General Experimental Procedures

The following compounds necessary for the invention were prepared according to literature methods such as described in WO 2018/165710 or unless otherwise described using techniques well known to those skilled in the art:

2-(Prop-2-yn-1-yl)pent-4-yn-1-ol (CAS 432027-96-8); (2-Hydroxypropane-1,3-diyl bis(hex-5-ynoate) (CAS1627101-87-4); 1,3-Bis(prop-2-yn-1-yloxy)propan-2-ol (CAS 16169-22-5) 2-(Prop-2-yn-1-yl)pent-4-yn-1-yl 4-hydroxybenzoate (CAS1627101-89-6) [2-(Prop-2-yn-1-yl)pent-4-yn-1-yl 3-hydroxybenzoate was prepared in the same manner]; 4-Hydroxy-N-(2-(prop-2-yn-1-yl)pent-4-yn-1-yl)benzamide (CAS1627101-91-0); 2-(Prop-2-yn-1-yl)pent-4-ynoic acid (CAS 65994-70-9) and 3-(Hex-5-ynoyloxy)-2-((hex-5-ynoyloxy)methyl)-2-methyl propanoic acid (CAS 1627101-95-4);

1-Chloroethyl (2-(prop-2-yn-1-yl)pent-4-yn-1-yl) carbonate (CAS 2102320-07-8); 2-((((1-chloroethoxy)carbonyl)oxy) methyl)-2-methylpropane-1,3-diyl bis(2,2-dimethylpent-4-ynoate) (CAS 2244811-48-9); 2-((((1-chloroethoxy)carbonyl)oxy) methyl)-2-methylpropane-1,3-diyl bis(hex-5-ynoate) (CAS 2244811-49-0); Chloromethyl (2-(prop-2-yn-1-yl) pent-4-yn-1-yl) carbonate (CAS 2244811-50-3); 2-(((1-chloroethoxy)carbonyl)oxy) propane-1,3-diyl bis(hex-5-ynoate) (CAS 2244811-51-4);

2-(Hydroxymethyl)-2-methylpropane-1,3-diyl bis(2,2-dimethylpent-4-ynoate) and 2-(hydroxymethyl)-2-methylpropane-1,3-diyl bis(hex-5-ynoate) were prepared using standard literature methods from 1,1,1-Tris(hydroxymethyl) ethane and the corresponding carboxylic acid using DCC; and (5-Hydroxy-6-methylpyridine-3,4-diyl)bis(methylene) bis (ethers) and (5-Hydroxy-6-methylpyridine-3,4-diyl)bis(methylene) bis (alkanoates) were all prepared using (5-(benzyloxy)-6-methylpyridine-3,4-diyl)dimethanol (5-PMB pyridoxine) and the appropriate carboxylic acid.

Method 1: Formation of HBTU mediated esters

A solution of the carboxylic acid substrate (1.0 eq.) in anhydrous THF or DCM is added to a stirring solution of HBTU (~1.2 eq.), the alcohol derivative (~1.6 eq.) and triethylamine (~4.3 eq.) in anhydrous THF or DCM under a nitrogen atmosphere. The mixture is stirred at room temperature for 3 days, with the exclusion of light, or until the reaction is complete. The reaction is quenched with 0.5 M or 1 M aqueous citric acid and extracted with DCM or ethyl acetate. The organic phase is then washed (sat. aq. $NaHCO_3$, and brine), dried ($Na_2SO_4$), filtered, concentrated, and dried in vacuo. Purification is by flash chromatography.

Method 2: Formation of [alkoxycarbonyl)oxy]alkyl esters

To a 0° C. solution of carboxylic acid (1.0 eq) in DMF is added $K_2CO_3$ (2.0 eq). After ~5 mins, a solution of alkyl chloride (3.30 eq) in DMF is added via cannula and the resultant solution is allowed to warm to room temperature and stirred for 5 days, or until the reaction is complete. The reaction is quenched with saturated aqueous ammonium chloride and extracted with ethyl acetate. The organic phase is then washed ($H_2O$, and brine), dried ($Na_2SO_4$), filtered, concentrated, and dried in vacuo. Purification is by flash chromatography.

Method 3: Formation of carbodiimide mediated ester

To a solution of the carboxylic acid substrate (1.0 eq), the alcohol derivative (1.1 eq) and DMAP (0.1 mol) in anhydrous DCM, is added dropwise a solution of N,N'-dicyclohexylcarbodiimide (DCC) or N,N'-diisopropylcarbodiimide (DIC) (1.1 eq) in anhydrous DCM at 0° C. The mixture is stirred at 0° C. for 1 h before allowing to warm to room temperature and stirring for 3 days, or until the reaction is complete. The mixture is concentrated, and dried in vacuo. Purification is by flash chromatography.

Building Blocks 2-(((4-Hydroxybenzoyl)oxy)methyl)-2-methylpropane-1,3-diyl bis(hex-5-ynoate)

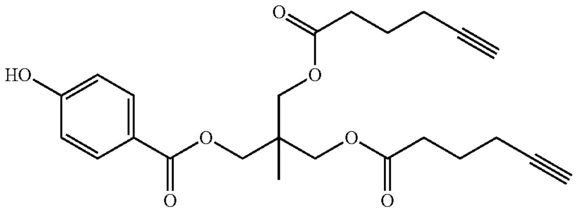 [SMILES: C#CCCCC(=O)OCC(C)(COC(=O)CCCC#C)COC(=O)c1ccc(O)cc1]

To a solution of p-hydroxybenzoic acid (1.38 g, 10.1 mmol) in DMF (60 mL) was added $K_2CO_3$ (3.48 g, 25.2 mmol) PMBCl (3.70 mL, 27.3 mmol). The mixture was stirred at rt for 44 h before EtOAc and 1 M citric acid were added. The product was extracted (EtOAc), washed (1M citric acid, then $H_2O$, then brine), dried ($Na_2SO_4$) filtered and concentrated under reduced pressure. The residue was suspended in EtOH (40 mL) before 4M KOH (aq) (10 mL, 40 mmol) was added. The mixture was stirred vigorously at rt for 48 h. The EtOH was removed under reduced pressure before petroleum spirit (boiling range 60-80° C.) and $H_2O$ were added to the residue. The product was extracted (dilute aq KOH) and washed (petroleum spirit petroleum spirit (boiling range 60-80° C.)) before the combined aqueous portions were acidified to ~pH2 with 6M HCl (aq). The product was extracted (EtOAc), the combined EtOAc phases washed (1 M HCl, then brine), dried ($Na_2SO_4$), filtered, concentrated and dried in vacuo. The crude residue was purified on the automated flash chromatography using 20%-100% EtOAc in petroleum spirit gradient elution to give 4-((4-methoxybenzyl)oxy)benzoic acid as a white solid (1.115 g, 4.32 mmol, 43% yield). R, =0.66 (50% EtOAc/petrol). $^1H$ NMR (400 MHz, $CDCl_3$) δ 8.04 (m, 2H), 7.36 (m, 2H), 7.01 (m, 2H), 6.93 (m, 2H), 5.06 (s, 2H), 3.83 (s, 3H). $^{13}C$ NMR (100 MHz, $CDCl_3$) b 171.6, 159.9, 156.1, 132.5, 129.4, 128.3, 121.7, 114.8, 114.3, 70.2, 55.5. LCMS: m/z 257.0 [M-H].

To a solution of 4-((4-methoxybenzyl)oxy)benzoic acid (503.4 mg, 1.95 mmol), 2-(hydroxymethyl)-2-methylpropane-1,3-diyl bis(hex-5-ynoate) (610.3 mg, 1.98 mmol) and DMAP (35.5 mg, 0.291 mmol) in $CH_2Cl_2$ (30 mL) was added DCC (423.4 mg, 2.05 mmol). The reaction was stirred at rt for 26 h before the $CH_2Cl_2$ was removed under reduced pressure. The resultant residue was slurried in EtOAc before filtering. The filtrate was concentrated and dried in vacuo. The crude residue was purified on the automated flash chromatography using 20%-100% EtOAc in petroleum spirit gradient elution to give impure material (827 mg). The material was dissolved in $CH_2Cl_2$ (40 mL). $Et_3SiH$ (310 μL, 1.94 mmol) was added and the mixture was stirred at rt for 30 min before TFA (404 μL, 5.28 mmol) was added. The reaction was stirred at rt for 42 h before concentrating under reduced pressure. $CH_2Cl_2$ and sat. aq. $NaHCO_3$ were added, the product was extracted ($CH_2Cl_2$), washed (sat. aq. $NaHCO_3$, then brine), dried ($Na_2SO_4$), filtered, concentrated and dried in vacuo. The crude residue was purified on the automated flash chromatography using 10%-100% EtOAc in petroleum spirit gradient elution to give 2-(((4-hydroxybenzoyl)oxy)methyl)-2-methylpropane-1,3-diyl bis(hex-5-ynoate) as a colourless oil (449.2 mg, 1.05 mmol, 54% yield over two steps). $^1H$ NMR (400 MHz, $CDCl_3$) δ 7.92 (m, 2H), 6.85 (m, 2H), 4.23 (s, 2H), 4.12 (s, 4H), 2.48 (t, J=7.5 Hz, 4H), 2.25 (td, J=6.9, 2.6 Hz, 4H), 1.97 (t, J=2.6 Hz, 2H), 1.84 (p, J=7.1 Hz, 4H), 1.11 (s, 3H).

(4-((2,2-Dimethylpent-4-ynamido)methyl)-5-hydroxy-6-methylpyridin-3-yl)methyl 2,2-dimethylpent-4-ynoate

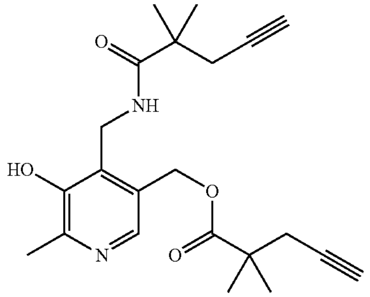 [SMILES: C#CCC(C)(C)C(=O)NCc1c(COC(=O)C(C)(C)CC#C)cnc(C)c1O]

To a solution of 2,2-dimethylpent-4-ynoic acid (941 mg, 7.46 mmol), DCC (1.45 g, 7.04 mmol) and DMAP (556 mg, 4.55 mmol) in DCM (30 ml) was added pyridoxamine dihydrochloride (500 mg, 2.07 mmol) according to the procedure outlined in Method 3 to give 4-((2,2-dimethylpent-4-ynamido)methyl)-5-(((2,2-dimethylpent-4-ynoyl)oxy)methyl)-2-methylpyridin-3-yl 2,2-dimethylpent-4-ynoate with impurities (1.35 g, 135% yield) that was used in the next step without further purification. $^1H$ NMR (400 MHz, $CDCl_3$) δ 8.44 (s, 1H), 6.24 (s, 1H), 5.26 (s, 2H), 2.65 (s, 2H), 2.51 (d, J=2.6 Hz, 1H), 2.47 (d, J=2.6 Hz, 1H), 2.44-2.41 (m, 5H), 2.40 (d, J=2.4 Hz, 2H), 2.14 (t, J=2.6 Hz, 1H), 1.97 (t, J=2.6 Hz, 1H), 1.95 (t, J=2.6 Hz, 1H), 1.37 (s, 3H), 1.32 (s, 2H), 1.28 (s, 7H), 1.23 (s, 6H).

To a solution of 4-((2,2-dimethylpent-4-ynamido)methyl)-5-(((2,2-dimethylpent-4-ynoyl)oxy)methyl)-2- methylpyridin-3-yl 2,2-dimethylpent-4-ynoate (1.35 g, 2.74 mmol) in MeOH (40 ml) was added $K_2CO_3$ (314 mg, 2.27 mmol) at 0° C. and the reaction left to stir for 1 h. A second portion of $K_2CO_3$ (314 mg, 2.27 mmol) was added and the reaction stirred for 1 h at 0° C. The reaction was then allowed to warm temperature and stirred for a further 1 h before being adjusted to pH 4 with TFA and the solvent removed in vacuo. The residue was dissolved (EtOAc), washed (sat. $NaHCO_3$ and brine), dried ($Na_2SO_4$), filtered and concentrated in vacuo. The crude residue was purified on the automated flash chromatography using 0%-5% MeOH in DCM gradient elution to give the title compound as a light yellow oil (472 mg, 59% yield over 2 steps). $^1H$ NMR (400 MHz, $CDCl_3$) δ 9.99 (s, 1H), 8.06 (s, 1H), 7.42 (t, J=5.6 Hz, 1H), 5.22 (s, 2H), 4.52 (s, 2H), 2.50 (s, 3H), 2.41 (dd, J=7.1, 2.6 Hz, 4H), 1.92 (t, J=2.6 Hz, 1H), 1.90 (t, J=2.7 Hz, 1H), 1.28 (s, 6H), 1.26 (s, 6H).

4-((3S,5aR,6R,7R,8aS)-6-((R,E)-4-(2,5-Difluorophenoxy)-3-hydroxybut-1-en-1-yl)-7-hydroxyoctahydro-2H-cyclopenta[b]oxepin-3-yl)butanoic acid (Sepetaprost Free Acid)

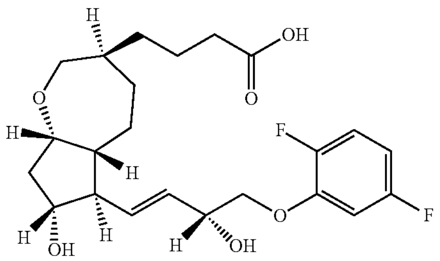 [SMILES: O=C(O)CCC[C@H]1CC[C@@H]2[C@@H](/C=C/[C@@H](O)COc3cc(F)ccc3F)[C@H](O)C[C@@H]2OC1]

To a solution of sepetaprost (1 eq.) in a 10:1 mixture of methanol and water is added lithium hydroxide (10 eq.). The mixture is stirred at room temperature for 16 h or until the reaction is complete. A 5:3 mixture of saturated aqueous ammonium chloride and 2M aqueous sodium hydrogen sulphate is then added and extracted with ethyl acetate. Further 2M aqueous sodium hydrogen sulphate is then added to the aqueous phase, the mixture is extracted with ethyl acetate. The combined organic layer is then washed with a 2:1 mixture of saturated aqueous ammonium chloride and 2M aqueous sodium hydrogen sulphate. The organic phase is then dried ($Na_2SO_4$), filtered, concentrated and dried in vacuo to gives the title compound.

Examples of Drug Monomers

Example 1: 2-(Prop-2-yn-1-yl)pent-4-yn-1-yl 4-((3S,5aR,6R,7R,8aS)-6-((R,E)-4-(2,5-difluorophenoxy)-3-hydroxybut-1-en-1-yl)-7-hydroxyoctahydro-2H-cyclopenta[b]oxepin-3-yl)butanoate

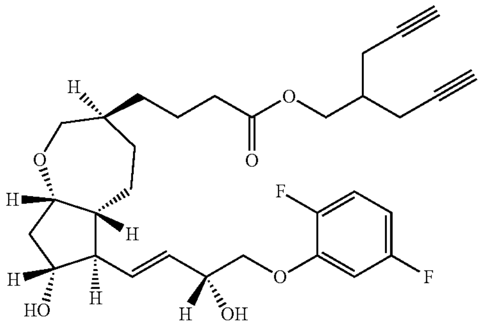 [SMILES: C#CCC(CC#C)COC(=O)CCC[C@H]1CC[C@@H]2[C@@H](/C=C/[C@@H](O)COc3cc(F)ccc3F)[C@H](O)C[C@@H]2OC1]

A solution of sepetaprost free acid (1.0 eq.) in anhydrous DCM is added to a stirring solution of HBTU (~1.2 eq.), 2-(prop-2-yn-1-yl)pent-4-yn-1-ol (~1.6 eq.) and triethylamine (~4.3 eq.) in anhydrous DCM are added according to the procedure outlined in Method 1 above. Purification of the crude residue by flash column chromatography on silica gel gives the title compound.

Example 2: 3-((4-((3S,5aR,6R,7R,8aS)-6-((R,E)-4-(2,5-Difluorophenoxy)-3-hydroxybut-1-en-1-yl)-7-hydroxyoctahydro-2H-cyclopenta[b]oxepin-3-yl)butanoyl)oxy)-2-((hex-5-yn-1-yloxy)methyl)-2-methylpropyl hex-5-ynoate

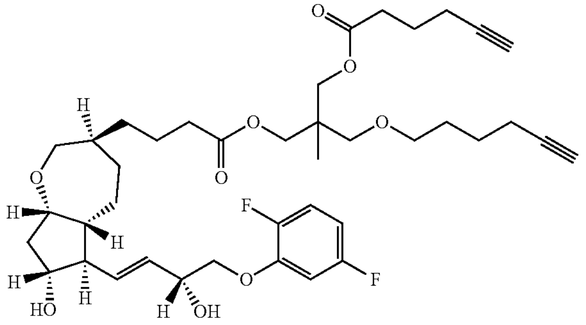 [SMILES: C#CCCCCOCC(C)(COC(=O)CCCC#C)COC(=O)CCC[C@H]1CC[C@@H]2[C@@H](/C=C/[C@@H](O)COc3cc(F)ccc3F)[C@H](O)C[C@@H]2OC1]

A solution of sepetaprost free acid (1.0 eq.) in anhydrous DCM is added to a stirring solution of HBTU (~1.2 eq.), 3-(hex-5-yn-1-yloxy)-2-(hydroxymethyl)-2-methylpropyl hex-5-ynoate (~1.6 eq.) and triethylamine (~4.3 eq.) in anhydrous DCM are added according to the procedure outlined in Method 1 above. Purification of the crude residue by flash column chromatography on silica gel gives the title compound.

Example 3: 2-(Prop-2-yn-1-yl)pent-4-yn-1-yl 4-((4-((3S,5aR,6R,7R,8aS)-6-((R,E)-4-(2,5-difluorophenoxy)-3-hydroxybut-1-en-1-yl)-7-hydroxyoctahydro-2H-cyclopenta[b]oxepin-3-yl)butanoyl)oxy)benzoate

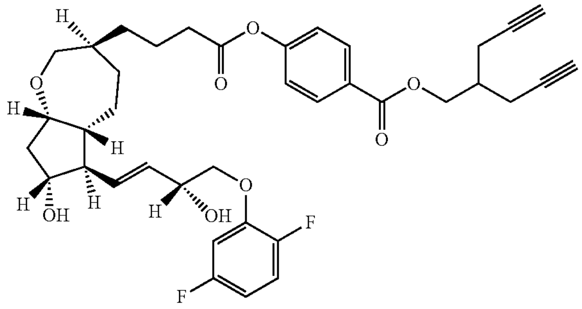 [SMILES: C#CCC(CC#C)COC(=O)c1ccc(OC(=O)CCC[C@H]2CC[C@@H]3[C@@H](/C=C/[C@@H](O)COc4cc(F)ccc4F)[C@H](O)C[C@@H]3OC2)cc1]

A solution of sepetaprost free acid (1.0 eq) in anhydrous DCM is added dropwise into a solution mixture of HBTU (1.1 eq), 2-(prop-2-yn-1-yl)pent-4-yn-1-yl 4-hydroxybenzoate (1.9 eq) and triethylamine (4.0 eq) in anhydrous DCM are added according to the procedure outlined in Method 1 above. Purification of the crude residue by flash column chromatography on silica gel gives the title compound.

Example 4: 2-(((4-((4-((3S,5aR,6R,7R,8aS)-6-((R,E)-4-(2,5-Difluorophenoxy)-3-hydroxybut-1-en-1-yl)-7-hydroxyoctahydro-2H-cyclopenta[b]oxepin-3-yl)butanoyl)oxy)benzoyl)oxy)methyl)-2-methylpropane-1,3-diyl bis(hex-5-ynoate)

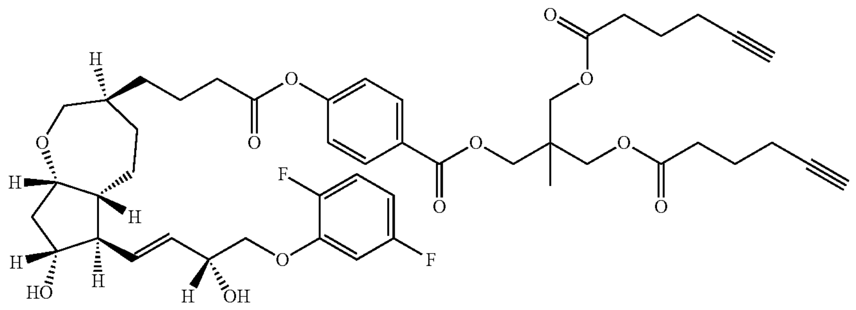 [SMILES: C#CCCCC(=O)OCC(C)(COC(=O)CCCC#C)COC(=O)c1ccc(OC(=O)CCC[C@H]2CC[C@@H]3[C@@H](/C=C/[C@@H](O)COc4cc(F)ccc4F)[C@H](O)C[C@@H]3OC2)cc1]

A solution of sepetaprost free acid (1.0 eq.) in anhydrous DCM is added to a stirring solution of HBTU (~1.2 eq.), 2-(((4-hydroxybenzoyl)oxy)methyl)-2-methylpropane-1,3-diyl bis(hex-5-ynoate) (~1.6 eq.) and triethylamine (~4.3 eq.) in anhydrous DCM are added according to the procedure outlined in Method 1 above. Purification of the crude residue by flash column chromatography on silica gel gives the title compound.

Example 5: 1-((((2-(Prop-2-yn-1-yl)pent-4-yn-1-yl)oxy)carbonyl)oxy)ethyl 4-((3S,5aR,6R,7R,8aS)-6-((R,E)-4-(2,5-difluorophenoxy)-3-hydroxybut-1-en-1-yl)-7-hydroxyoctahydro-2H-cyclopenta[b]oxepin-3-yl)butanoate

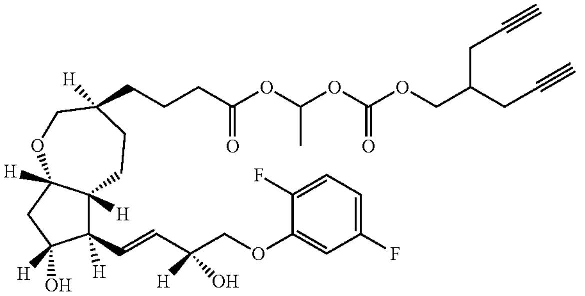 [SMILES: C#CCC(CC#C)COC(=O)OC(C)OC(=O)CCC[C@H]1CC[C@@H]2[C@@H](/C=C/[C@@H](O)COc3cc(F)ccc3F)[C@H](O)C[C@@H]2OC1]

To a 0° C. solution of sepetaprost free acid (1.0 eq) in DMF is added $K_2CO_3$ (2.0 eq). After 5 mins, a solution of 1-chloroethyl (2-(prop-2-yn-1-yl)pent-4-yn-1-yl) carbonate (3.30 eq) in DMF is added according to the procedure outlined in Method 2 above. Purification of the crude residue by flash column chromatography on silica gel gives the title compound.

Example 6: 2-((((1-((4-((3S,5aR,6R,7R,8aS)-6-((R,E)-4-(2,5-Difluorophenoxy)-3-hydroxybut-1-en-1-yl)-7-hydroxyoctahydro-2H-cyclopenta[b]oxepin-3-yl)butanoyl)oxy)ethoxy)carbonyl)oxy)methyl)propane-1,3-diyl bis(hex-5-ynoate)

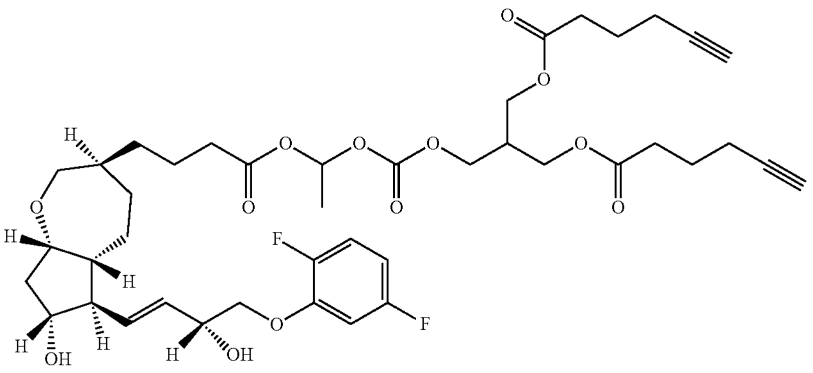 [SMILES: C#CCCCC(=O)OCC(COC(=O)CCCC#C)COC(=O)OC(C)OC(=O)CCC[C@H]1CC[C@@H]2[C@@H](/C=C/[C@@H](O)COc3cc(F)ccc3F)[C@H](O)C[C@@H]2OC1]

To a 0° C. solution of sepetaprost free acid (1.0 eq) in DMF is added $K_2CO_3$ (2.0 eq). After 1 h, a solution of 2-((((1-chloroethoxy)carbonyl)oxy)methyl)propane-1,3-diyl bis(hex-5-ynoate) (2.40 eq) in DMF is added according to the procedure outlined in Method 2 above. Purification of the crude residue by flash column chromatography on silica gel gives the title compound.

Example 7: (5-((4-((3S,5aR,6R,7R,8aS)-6-((R,E)-4-(2,5-Difluorophenoxy)-3-hydroxybut-1-en-1-yl)-7-hydroxyoctahydro-2H-cyclopenta[b]oxepin-3-yl)butanoyl)oxy)-6-methylpyridine-3,4-diyl)bis(methylene) bis(2,2-dimethylpent-4-ynoate)

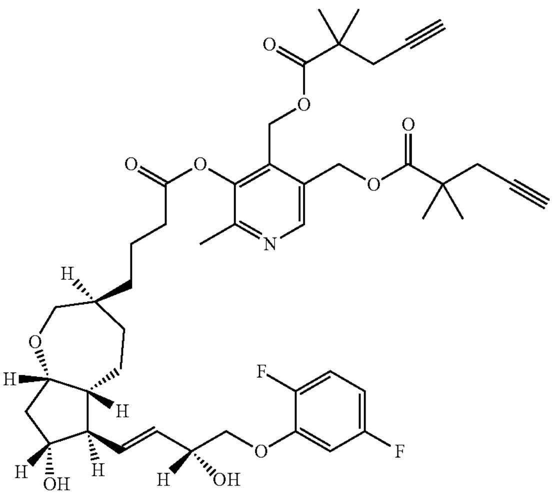 [SMILES: C#CCC(C)(C)C(=O)OCc1cnc(C)c(OC(=O)CCC[C@H]2CC[C@@H]3[C@@H](/C=C/[C@@H](O)COc4cc(F)ccc4F)[C@H](O)C[C@@H]3OC2)c1COC(=O)C(C)(C)CC#C]

A solution of sepetaprost free acid (1.0 eq.) in anhydrous DCM is added to a stirring solution of HBTU (~1.2 eq.), (5-hydroxy-6-methylpyridine-3,4-diyl)bis(methylene) bis(2,2-dimethylpent-4-ynoate) (~1.6 eq.) and triethylamine (~4.3 eq.) in anhydrous DCM are added according to the procedure outlined in Method 1 above. Purification of the crude residue by flash column chromatography on silica gel gives the title compound.

Example 8: 2-Methyl-4,5-bis((prop-2-yn-1-yloxy)methyl)pyridin-3-yl 4-((3S,5aR,6R,7R,8aS)-6-((R,E)-4-(2,5-difluorophenoxy)-3-hydroxybut-1-en-1-yl)-7-hydroxyoctahydro-2H-cyclopenta[b]oxepin-3-yl)butanoate

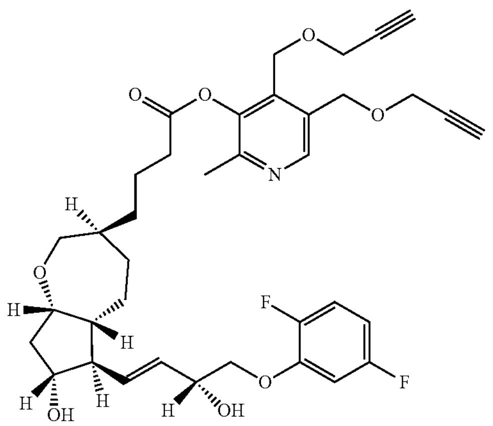 [SMILES: C#CCOCc1cnc(C)c(OC(=O)CCC[C@H]2CC[C@@H]3[C@@H](/C=C/[C@@H](O)COc4cc(F)ccc4F)[C@H](O)C[C@@H]3OC2)c1COCC#C]

A solution of sepetaprost free acid (1.0 eq.) in anhydrous DCM is added to a stirring solution of HBTU (~1.2 eq.), 2-methyl-4,5-bis((prop-2-yn-1-yloxy)methyl)pyridin-3-ol (~1.6 eq.) and triethylamine (~4.3 eq.) in anhydrous DCM are added according to the procedure outlined in Method 1 above. Purification of the crude residue by flash column chromatography on silica gel gives the title compound.

Example 9: (5-((4-((3S,5aR,6R,7R,8aS)-6-((R,E)-4-(2,5-Difluorophenoxy)-3-hydroxybut-1-en-1-yl)-7-hydroxyoctahydro-2H-cyclopenta[b]oxepin-3-yl)butanoyl)oxy)-4-((2,2-dimethylpent-4-ynamido)methyl)-6-methylpyridin-3-yl)methyl 2,2-dimethylpent-4-ynoate

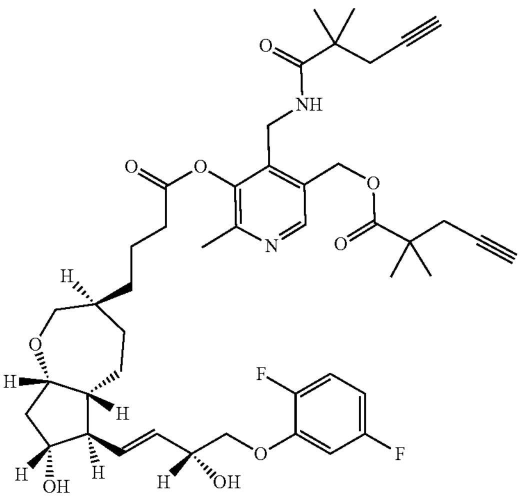 [SMILES: C#CCC(C)(C)C(=O)NCc1c(COC(=O)C(C)(C)CC#C)cnc(C)c1OC(=O)CCC[C@H]1CC[C@@H]2[C@@H](/C=C/[C@@H](O)COc3cc(F)ccc3F)[C@H](O)C[C@@H]2OC1]

A solution of sepetaprost free acid (1.0 eq.) in anhydrous DCM is added to a stirring solution of HBTU (~1.2 eq.), (4-((2,2-dimethylpent-4-ynamido)methyl)-5-hydroxy-6-methylpyridin-3-yl)methyl 2,2-dimethylpent-4-ynoate (~1.6 eq.) and triethylamine (~4.3 eq.) in anhydrous THF or DCM are added according to the procedure outlined in Method 1 above. Purification of the crude residue by flash column chromatography on silica gel gives the title compound.

Example 10: 2-Methyl-4-((prop-2-yn-1-ylamino)methyl)-5-((prop-2-yn-1-yloxy)methyl)pyridin-3-yl 4-((3S,5aR,6R,7R,8aS)-6-((R,E)-4-(2,5-difluorophenoxy)-3-hydroxybut-1-en-1-yl)-7-hydroxyoctahydro-2H-cyclopenta[b]oxepin-3-yl)butanoate

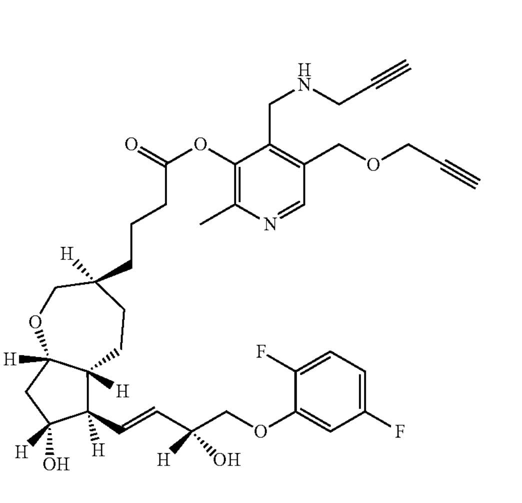 [SMILES: C#CCNCc1c(COCC#C)cnc(C)c1OC(=O)CCC[C@H]1CC[C@@H]2[C@@H](/C=C/[C@@H](O)COc3cc(F)ccc3F)[C@H](O)C[C@@H]2OC1]

A solution of sepetaprost free acid (1.0 eq.) in anhydrous DCM is added to a stirring solution of HBTU (~1.2 eq.), 2-methyl-4-((prop-2-yn-1-ylamino)methyl)-5-((prop-2-yn-1-yloxy)methyl)pyridin-3-ol (~1.6 eq.) and triethylamine (~4.3 eq.) in anhydrous DCM are added according to the procedure outlined in Method 1 above. Purification of the crude residue by flash column chromatography on silica gel gives the title compound.

Example 11: isopropyl 4-((3S,5aR,6R,7R,8aS)-6-((R,E)-4-(2,5-difluorophenoxy)-3-((((2-(prop-2-yn-1-yl)pent-4-yn-1-yl)oxy)carbonyl)oxy)but-1-en-1-yl)-7-hydroxyoctahydro-2H-cyclopenta[b]oxepin-3-yl)butanoate

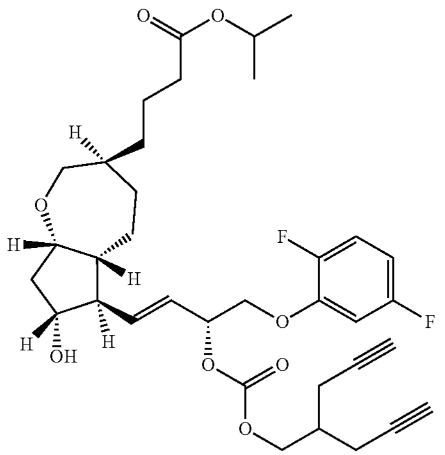

isopropyl 4-((3S,5aR,6R,7R,8aS)-6-((R,E)-4-(2,5-difluorophenoxy)-3-((((2-(prop-2-yn-1-yl)pent-4-yn-1-yl)oxy)carbonyl)oxy)but-1-en-1-yl)-7-hydroxyoctahydro-2H-cyclopenta[b]oxepin-3-yl)butanoate To a solution of 2-(prop-2-yn-1-yl)pent-4-yn-1-ol (716.9 mg, 5.87 mmol) and triphosgene ((877.3 mg, 2.96 mmol)) in anhydrous DCM (10 mL), pyridine (0.62 mL, 608.8 mg, 7.70 mmol)) was added dropwise at −40° C. The reaction mixture was stirred at −40° C. for 2 h, then slowly warmed to room temperature and stirred for 4 h or until the reaction is complete. The reaction mixture was filtered through a thin layer of silica gel, concentrated and dried in vacuo to give 2-(prop-2-yn-1-yl)pent-4-yn-1-yl carbonochloridate as a clear colourless oil (897.7 mg, 83% yield).

To a solution of sepatoprost (1.0 eq) in anhydrous pyridine, chloroformate derivative 2-(prop-2-yn-1-yl)pent-4-yn-1-yl carbonochloridate (2-3 eq) is added at 0° C. The reaction mixture is stirred at room temperature for 16 h or until the reaction is complete. The residue is extracted into ethyl acetate and washed with water and brine. The organic phase is dried over $Na_2SO_4$, filtered, concentrated and dried in vacuo. The residue is purified on an automated flash chromatography using 0%-100% EtOAc in pet. spirit gradient elution to give the title compound.

Example 12

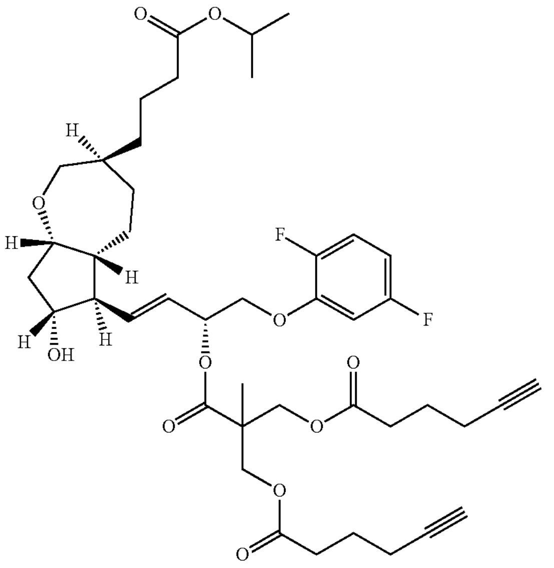 [SMILES: C#CCCCC(=O)OCC(C)(COC(=O)CCCC#C)C(=O)O[C@H](/C=C/[C@@H]1[C@H]2CC[C@H](CCCC(=O)OC(C)C)CO[C@H]2C[C@H]1O)COc1cc(F)ccc1F]

A solution of sepatoprost (1.0 eq) in anhydrous DCM is added dropwise to a solution of 3-(hex-5-ynoyloxy)-2-((hex-5-ynoyloxy)methyl)-2-methylpropanoic acid (1.0 eq), DCC (1.0 eq) and DMAP (0.25 eq) in anhydrous DCM according to Method 3 outlined above and stirred at room temperature for 24 hrs. The crude residue is purified on an automated flash chromatography system using a gradient to give the title compound.

Example 13

The following compounds can be used with either sepatoprost or sepatoprost free acid along with the methods described above, in WO 2018/165710 or using techniques well known to those skilled in the art, to prepare drug-monomer conjugates for use in the invention.

TABLE 2

| Structure/Name |
| --- |
| 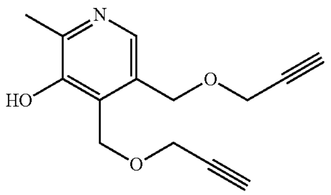 [SMILES: C#CCOCc1cnc(C)c(O)c1COCC#C] 2-Methyl-4,5-bis((prop-2-yn-1-yloxy)methyl)pyridin-3-ol |

TABLE 2-continued

| Structure/Name |
| --- |
| 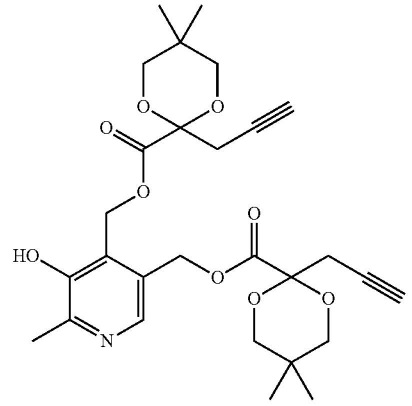 [SMILES: C#CCC1(C(=O)OCc2cnc(C)c(O)c2COC(=O)C2(CC#C)OCC(C)(C)CO2)OCC(C)(C)CO1] (5-Hydroxy-6-methylpyridine-3,4-diyl)bis(methylene)bis(5,5-dimethyl-2-(prop-2-yn-1-yl)-1,3-dioxane-2-carboxylate) |
| 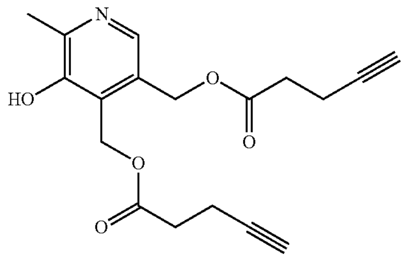 [SMILES: C#CCCC(=O)OCc1cnc(C)c(O)c1COC(=O)CCC#C] (5-Hydroxy-6-methylpyridine-3,4-diyl)bis(methylene)bis(pent-4-ynoate) |
| 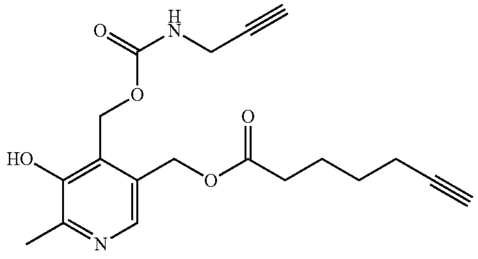 [SMILES: C#CCCCCC(=O)OCc1cnc(C)c(O)c1COC(=O)NCC#C] (5-Hydroxy-6-methyl-4-(((prop-2-yn-1-ylcarbamoyl)oxy)methyl)pyridin-3-yl)methyl hept-6-ynoate |
| 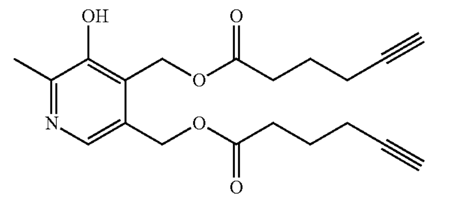 [SMILES: C#CCCCC(=O)OCc1cnc(C)c(O)c1COC(=O)CCCC#C] (5-Hydroxy-6-methylpyridine-3,4-diyl)bis(methylene)bis(hex-5-ynoate) |

TABLE 2-continued

| Structure/Name |
| --- |
| 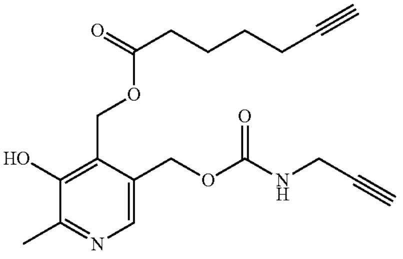 [SMILES: C#CCCCCC(=O)OCc1c(COC(=O)NCC#C)cnc(C)c1O] |
| (3-Hydroxy-2-methyl-5-(((prop-2-yn-1-ylcarbamoyl)oxy)methyl)pyridin-4-yl)methyl hept-6-ynoate |
| 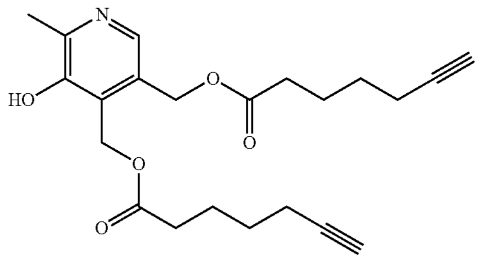 [SMILES: C#CCCCCC(=O)OCc1cnc(C)c(O)c1COC(=O)CCCCC#C] |
| (5-Hydroxy-6-methylpyridine-3,4-diyl)bis(methylene)bis(hept-6-ynoate |
| 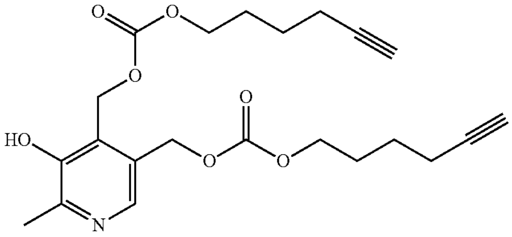 [SMILES: C#CCCCCOC(=O)OCc1cnc(C)c(O)c1COC(=O)OCCCCC#C] |
| di(Hex-5-yn-1-yl)((5-hydroxy-6-methylpyridine-3,4-diyl)bis(methylene))bis(carbonate) |
| 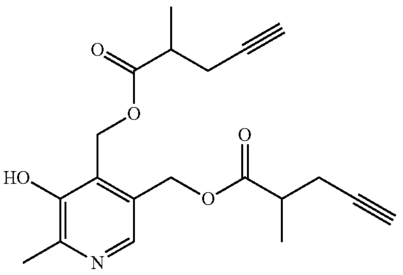 [SMILES: C#CCC(C)C(=O)OCc1cnc(C)c(O)c1COC(=O)C(C)CC#C] |
| (5-Hydroxy-6-methylpyridine-3,4-diyl)bis(methylene)bis(2-methylpent-4-ynoate) |
| 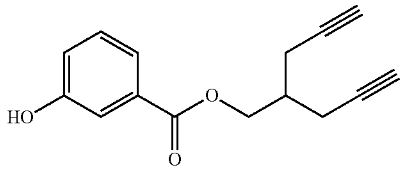 [SMILES: C#CCC(CC#C)COC(=O)c1cccc(O)c1] |
| 2-(Prop-2-yn-1-yl)pent-4-yn-1-yl 3-hydroxybenzoate |

TABLE 2-continued

| Structure/Name |
| --- |
| 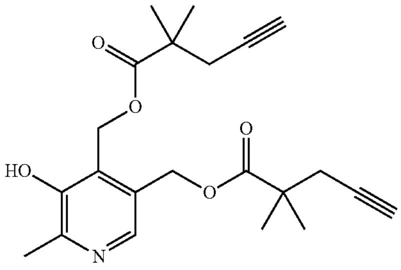 [SMILES: C#CCC(C)(C)C(=O)OCc1cnc(C)c(O)c1COC(=O)C(C)(C)CC#C] |
| (5-Hydroxy-6-methylpyridine-3,4-diyl)bis(methylene)bis(2,2-dimethylpent-4-ynoate) |
| 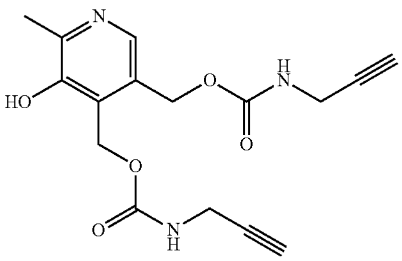 [SMILES: C#CCNC(=O)OCc1cnc(C)c(O)c1COC(=O)NCC#C] |
| (5-Hydroxy-6-methylpyridine-3,4-diyl)bis(methylene)bis(prop-2-yn-1-ylcarbamate) |
| 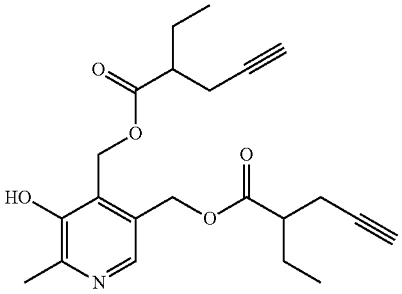 [SMILES: C#CCC(CC)C(=O)OCc1cnc(C)c(O)c1COC(=O)C(CC)CC#C] |
| (5-Hydroxy-6-methylpyridine-3,4-diyl)bis(methylene)bis(2-ethylpent-4-ynoate) |
| 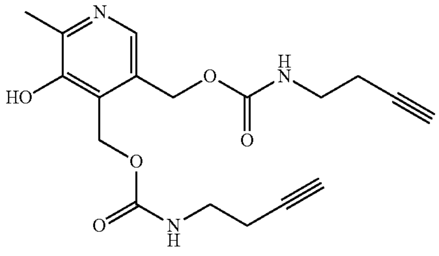 [SMILES: C#CCCNC(=O)OCc1cnc(C)c(O)c1COC(=O)NCCC#C] |
| (5-Hydroxy-6-methylpyridine-3,4-diyl)bis(methylene)bis(but-3-yn-1-ylcarbamate) |

TABLE 2-continued

| Structure/Name |
| --- |
| 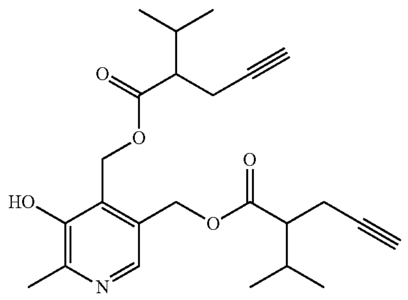 [SMILES: C#CCC(C(=O)OCc1cnc(C)c(O)c1COC(=O)C(CC#C)C(C)C)C(C)C] |
| (5-Hydroxy-6-methylpyridine-3,4-diyl)bis(methylene)bis(2-isopropylpent-4-ynoate) |
| 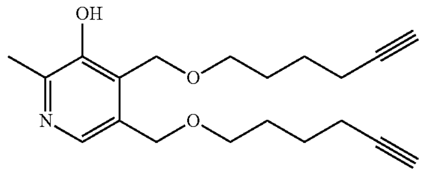 [SMILES: C#CCCCCOCc1cnc(C)c(O)c1COCCCCC#C] |
| 4,5-bis((Hex-5-yn-1-yloxy)methyl)-2-methylpyridin-3-ol |
| 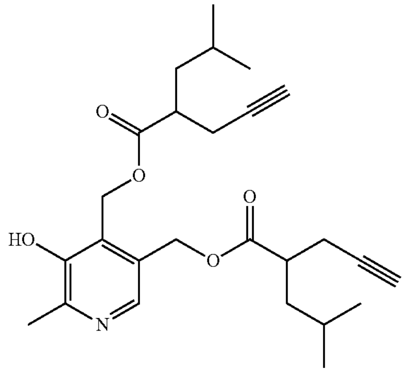 [SMILES: C#CCC(CC(C)C)C(=O)OCc1cnc(C)c(O)c1COC(=O)C(CC#C)CC(C)C] |
| (5-Hydroxy-6-methylpyridine-3,4-diyl)bis(methylene)bis(2-isobutylpent-4-ynoate) |
| 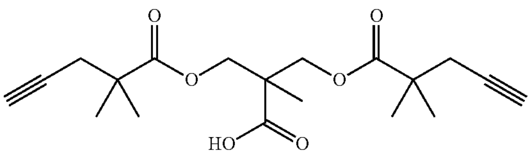 [SMILES: C#CCC(C)(C)C(=O)OCC(C)(COC(=O)C(C)(C)CC#C)C(=O)O] |
| 3-((2,2-Dimethylpent-4-ynoyl)oxy)-2-(((2,2-dimethylpent-4-ynoyl)oxy)methyl)-2-methylpropanoic acid |

TABLE 2-continued

| Structure/Name |
| --- |
| 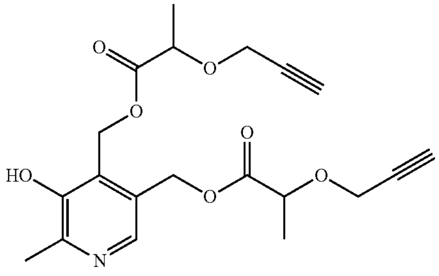 [SMILES: C#CCOC(C)C(=O)OCc1cnc(C)c(O)c1COC(=O)C(C)OCC#C] |
| (5-Hydroxy-6-methylpyridine-3,4-diyl)bis(methylene)bis(2-(prop-2-yn-1-yloxy)propanoate) |
| 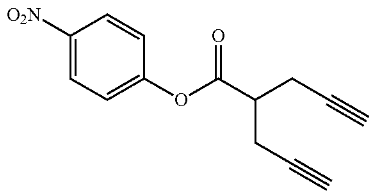 [SMILES: C#CCC(CC#C)C(=O)Oc1ccc([N+](=O)[O-])cc1] |
| 4-Nitrophenyl 2-(prop-2-yn-1-yl)pent-4-ynoate |
| 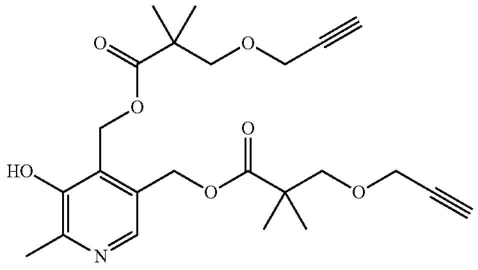 [SMILES: C#CCOCC(C)(C)C(=O)OCc1cnc(C)c(O)c1COC(=O)C(C)(C)COCC#C] |
| (5-Hydroxy-6-methylpyridine-3,4-diyl)bis(methylene)bis(2,2-dimethyl-3-(prop-2-yn-1-yloxy)propanoate) |
| 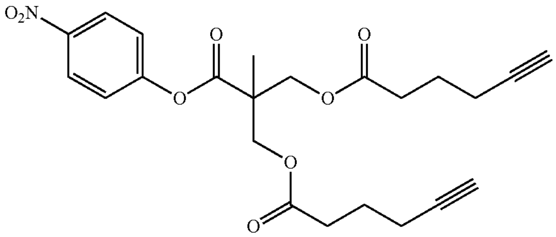 [SMILES: C#CCCCC(=O)OCC(C)(COC(=O)CCCC#C)C(=O)Oc1ccc([N+](=O)[O-])cc1] |
| 2-Methyl-2-((4-nitrophenoxy)carbonyl)propane-1,3-diyl bis(hex-5-ynoate) |

TABLE 2-continued

| Structure/Name |
|---|
| 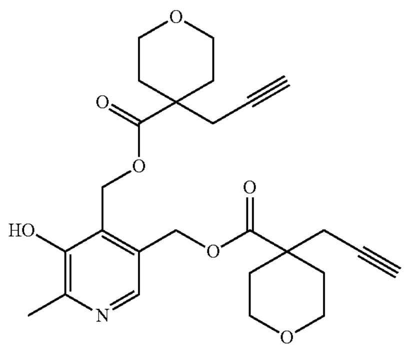 [SMILES: C#CCC1(C(=O)OCc2cnc(C)c(O)c2COC(=O)C2(CC#C)CCOCC2)CCOCC1] |
| (5-Hydroxy-6-methylpyridine-3,4-diyl)bis(methylene)bis(4-(prop-2-yn-1-yl)tetrahydro-2H-pyran-4-carboxylate) |
| 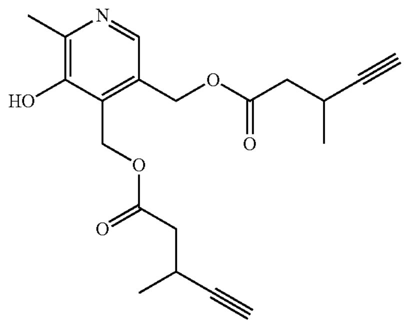 [SMILES: C#CC(C)CC(=O)OCc1cnc(C)c(O)c1COC(=O)CC(C)C#C] |
| (5-Hydroxy-6-methylpyridine-3,4-diyl)bis(methylene)bis(3-methylpent-4-ynoate) |
| 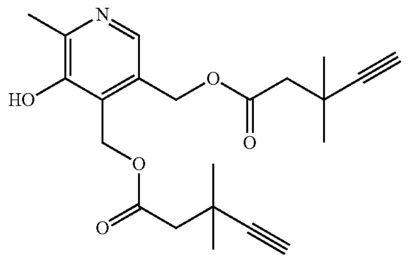 [SMILES: C#CC(C)(C)CC(=O)OCc1cnc(C)c(O)c1COC(=O)CC(C)(C)C#C] |
| (5-Hydroxy-6-methylpyridine-3,4-diyl)bis(methylene)bis(3,3-dimethylpent-4-ynoate) |
| 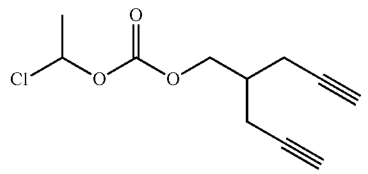 |
| 1-Chloroethyl (2-(prop-2-yn-1-yl)pent-4-yn-1-yl) carbonate |

TABLE 2-continued

| Structure/Name |
|---|
| 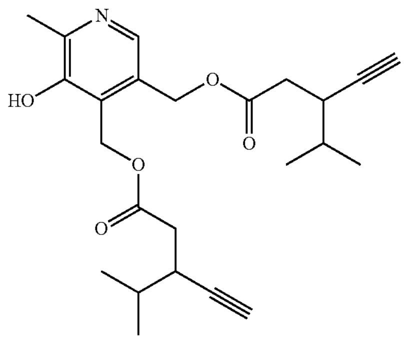 [SMILES: C#CC(CC(=O)OCc1cnc(C)c(O)c1COC(=O)CC(C#C)C(C)C)C(C)C] |
| (5-Hydroxy-6-methylpyridine-3,4-diyl)bis(methylene)bis(3-isopropylpent-4-ynoate) |
| 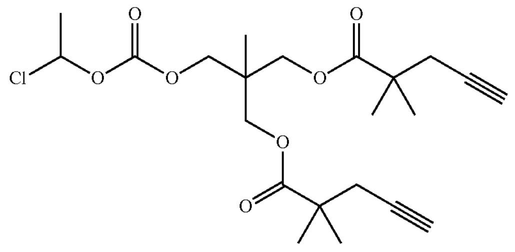 [SMILES: C#CCC(C)(C)C(=O)OCC(C)(COC(=O)OC(C)Cl)COC(=O)C(C)(C)CC#C] |
| 2-((((1-Chloroethoxy)carbonyl)oxy)methyl)-2-methylpropane-1,3-diyl bis(2,2-dimethylpent-4-ynoate) |
| 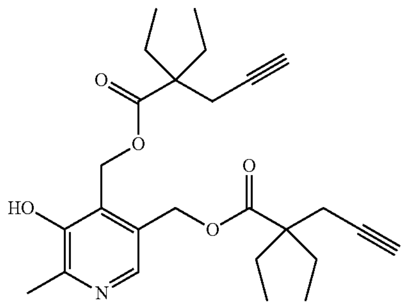 [SMILES: C#CCC(CC)(CC)C(=O)OCc1cnc(C)c(O)c1COC(=O)C(CC)(CC)CC#C] |
| (5-Hydroxy-6-methylpyridine-3,4-diyl)bis(methylene)bis(2,2-diethylpent-4-ynoate) |
| 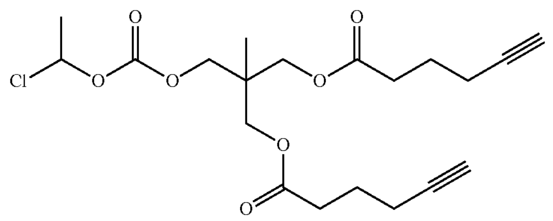 [SMILES: C#CCCCC(=O)OCC(C)(COC(=O)CCCC#C)COC(=O)OC(C)Cl] |
| 2-((((1-Chloroethoxy)carbonyl)oxy)methyl)-2-methylpropane-1,3-diyl bis(hex-5-ynoate) |

TABLE 2-continued

| Structure/Name |
| --- |
| 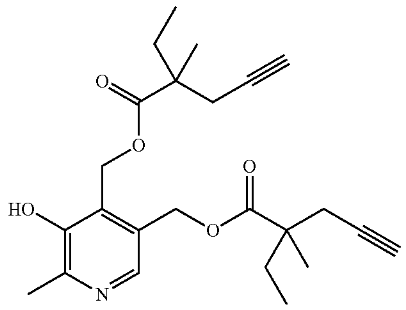 [SMILES: C#CCC(C)(CC)C(=O)OCc1cnc(C)c(O)c1COC(=O)C(C)(CC)CC#C] (5-Hydroxy-6-methylpyridine-3,4-diyl)bis(methylene)bis(2-ethyl-2-methylpent-4-ynoate) |
| 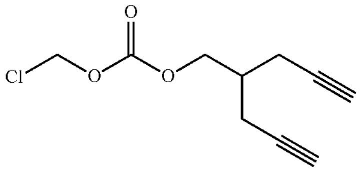 Chloromethyl (2-(prop-2-yn-1-yl)pent-4-yn-1-yl) carbonate |
| 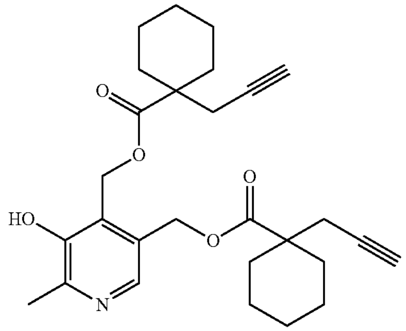 [SMILES: C#CCC1(C(=O)OCc2cnc(C)c(O)c2COC(=O)C2(CC#C)CCCCC2)CCCCC1] (5-Hydroxy-6-methylpyridine-3,4-diyl)bis(methylene)bis(1-(prop-2-yn-1-yl)cyclohexane-1-carboxylate) |
| 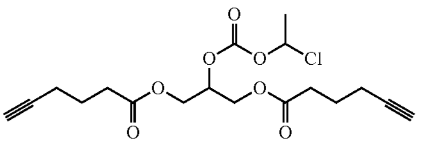 [SMILES: C#CCCCC(=O)OCC(COC(=O)CCCC#C)OC(=O)OC(C)Cl] 2-(((1-Chloroethoxy)carbonyl)oxy)propane-1,3-diyl bis(hex-5-ynoate) |

TABLE 2-continued

| Structure/Name |
| --- |
| 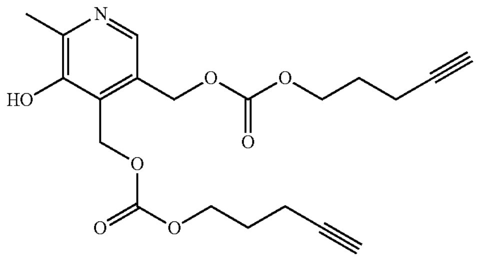 (5-Hydroxy-6-methylpyridine-3,4-diyl)bis(methylene)di(pent-4-yn-1-yl) bis(carbonate) |
| 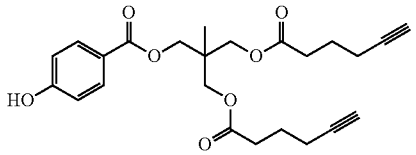 [SMILES: C#CCCCC(=O)OCC(C)(COC(=O)CCCC#C)COC(=O)c1ccc(O)cc1] 2-(((4-Hydroxybenzoyl)oxy)methyl)-2-methylpropane-1,3-diyl bis(hex-5-ynoate) |
| 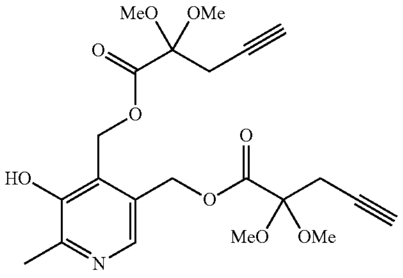 [SMILES: C#CCC(OC)(OC)C(=O)OCc1cnc(C)c(O)c1COC(=O)C(CC#C)(OC)OC] (5-Hydroxy-6-methylpyridine-3,4-diyl)bis(methylene)bis(2,2-dimethoxypent-4-ynoate) |
| 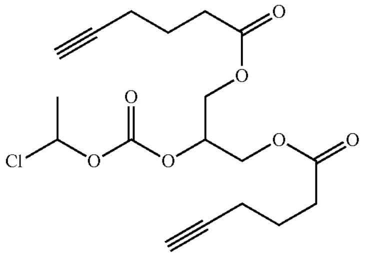 [SMILES: C#CCCCC(=O)OCC(COC(=O)CCCC#C)OC(=O)OC(C)Cl] 2-(((1-Chloroethoxy)carbonyl)oxy)propane-1,3-diyl bis(hex-5-ynoate) |
| 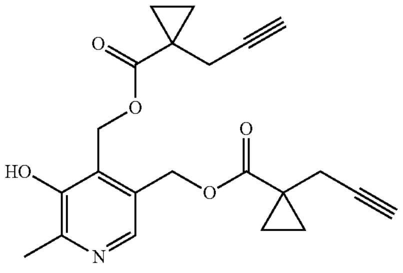 [SMILES: C#CCC1(C(=O)OCc2cnc(C)c(O)c2COC(=O)C2(CC#C)CC2)CC1] (5-Hydroxy-6-methylpyridine-3,4-diyl)bis(methylene)bis(1-(prop-2-yn-1-yl)cyclopropane-1-carboxylate) |

TABLE 2-continued

Structure/Name

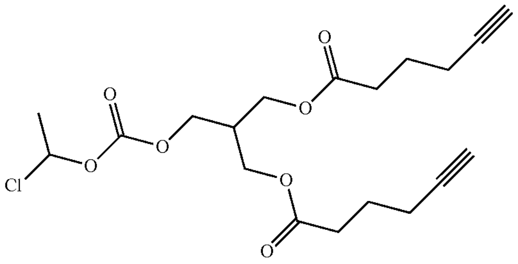 [SMILES: C#CCCCC(=O)OCC(COC(=O)CCCC#C)COC(=O)OC(C)Cl]

2-((((1-Chloroethoxy)carbonyl)oxy)methyl)propane-1,3-diyl bis(hex-5-ynoate)

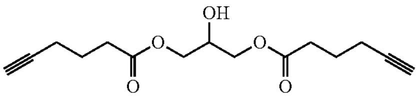 [SMILES: C#CCCCC(=O)OCC(O)COC(=O)CCCC#C]

2-hydroxypropane-1,3-diyl bis(hex-5-ynoate)

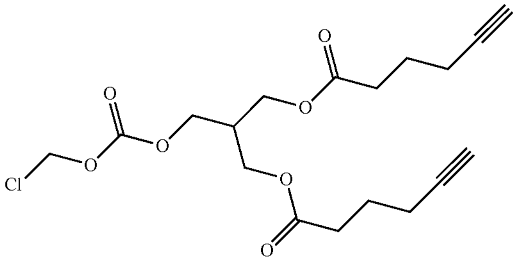 [SMILES: C#CCCCC(=O)OCC(COC(=O)CCCC#C)COC(=O)OCCl]

2-((((Chloromethoxy)carbonyl)oxy)methyl)propane-1,3-diyl bis(hex-5-ynoate)

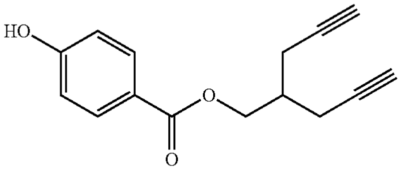 [SMILES: C#CCC(CC#C)COC(=O)c1ccc(O)cc1]

2-(Prop-2-yn-1-yl)pent-4-yn-1-yl 4-hydroxybenzoate

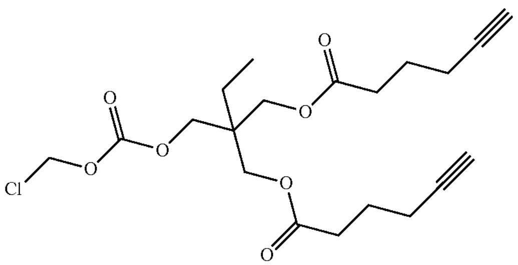 [SMILES: C#CCCCC(=O)OCC(CC)(COC(=O)CCCC#C)COC(=O)OCCl]

2-((((Chloromethoxy)carbonyl)oxy)methyl)-2-ethylpropane-1,3-diyl bis(hex-5-ynoate)

TABLE 2-continued

Structure/Name

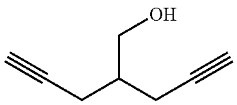

2-(Prop-2-yn-1-yl)pent-4-yn-1-ol

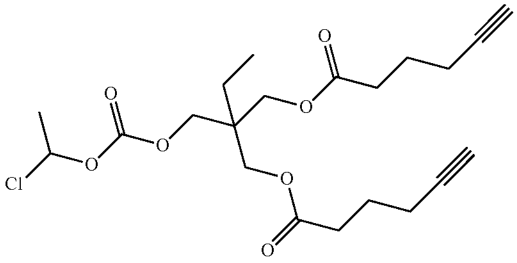 [SMILES: C#CCCCC(=O)OCC(CC)(COC(=O)CCCC#C)COC(=O)OC(C)Cl]

2-((((1-Chloroethoxy)carbonyl)oxy)methyl)-2-ethylpropane-1,3-diyl bis(hex-5-ynoate)

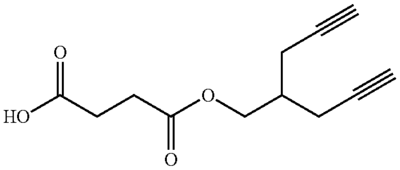 [SMILES: C#CCC(CC#C)COC(=O)CCC(=O)O]

4-Oxo-4-((2-(prop-2-yn-1-yl)pent-4-yn-1-yl)oxy)butanoic acid

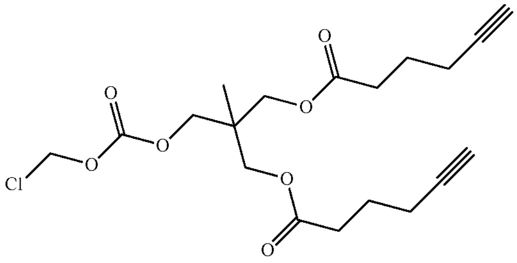 [SMILES: C#CCCCC(=O)OCC(C)(COC(=O)CCCC#C)COC(=O)OCCl]

2-((((Chloromethoxy)carbonyl)oxy)methyl)-2-methylpropane-1,3-diyl bis(hex-5-ynoate)

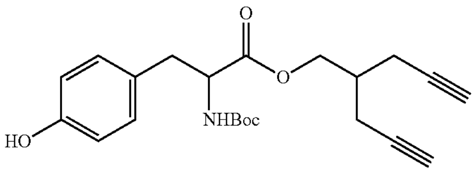 [SMILES: C#CCC(CC#C)COC(=O)C(Cc1ccc(O)cc1)NC(=O)OC(C)(C)C]

2-(prop-2-yn-1-yl)pent-4-yn-1-yl(tert-butoxycarbonyl)tyrosinate

TABLE 2-continued

| Structure/Name |
|---|
| 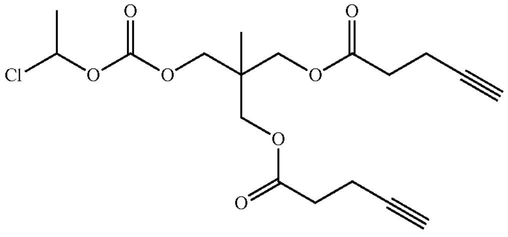 [SMILES: C#CCCC(=O)OCC(C)(COC(=O)CCC#C)COC(=O)OC(C)Cl]<br>2-((((1-Chloroethoxy)carbonyl)oxy)methyl)-2-methylpropane-1,3-diyl bis(pent-4-ynoate) |

TABLE 2-continued

| Structure/Name |
|---|
| 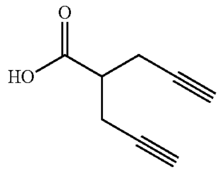<br>2-(prop-2-yn-1-yl)pent-4-ynoic acid |

Examples of Co-Monomers

Using methods described in WO 2018/165711 A1 the following polymers in

TABLE 3

| Ex. | Structure | MW of PEG used |
|---|---|---|
| 14 | 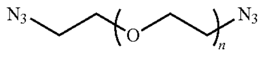 | PEG3000<br>PEG2000<br>PEG1000<br>PEG800<br>PEG400 |
| 15 | 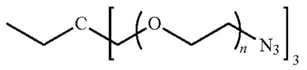 | PEG1000<br>PEG450 |
| 16 | 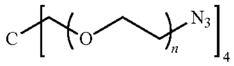 | PEG5000<br>PEG2000<br>PEG1000<br>PEG800 |
| 17 | 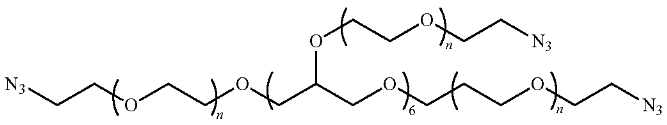 | PEG10000<br>PEG5000 |
| 18 | 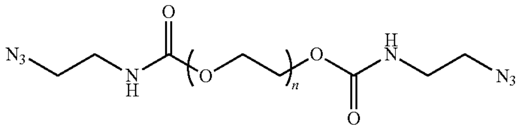 | PEG3000<br>PEG2000<br>PEG1000<br>PEG800<br>PEG400 |
| 19 | 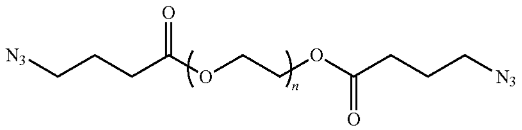 | PEG3000<br>PEG2000<br>PEG1000<br>PEG800<br>PEG400 |
| 20 | 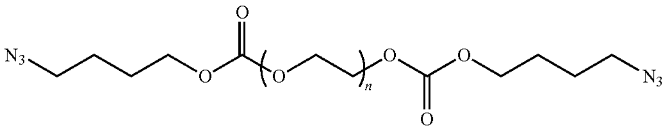 | PEG3000<br>PEG2000<br>PEG1000<br>PEG800<br>PEG400 |
| 21 | 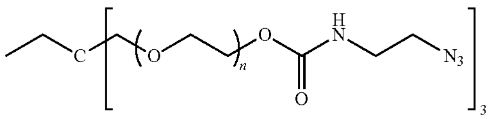 | PEG1000<br>PEG450 |
| 22 | 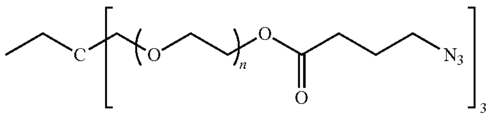 | PEG1000<br>PEG450 |

TABLE 3-continued
| Ex. | Structure | MW of PEG used |
|---|---|---|
| 23 | 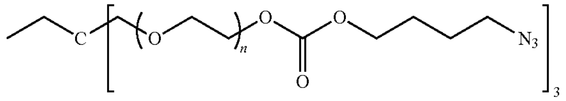 | PEG1000<br>PEG450 |
| 24 | 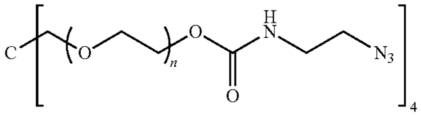 | PEG5000<br>PEG2000<br>PEG1000<br>PEG800 |
| 25 | 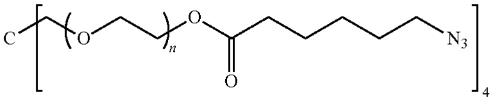 | PEG5000<br>PEG2000<br>PEG1000<br>PEG800 |
| 26 | 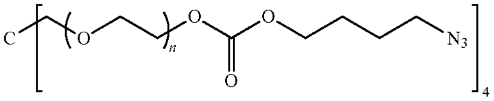 | PEG5000<br>PEG2000<br>PEG1000<br>PEG800 |
| 27 | 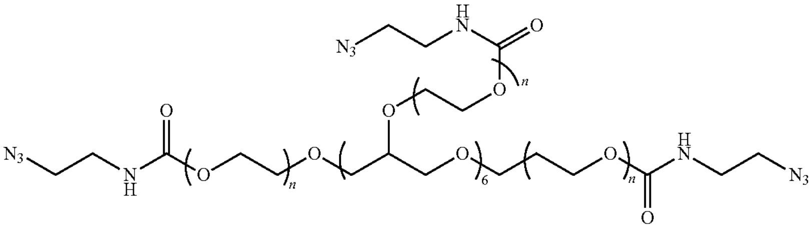 | PEG10000<br>PEG5000 |
| 28 | 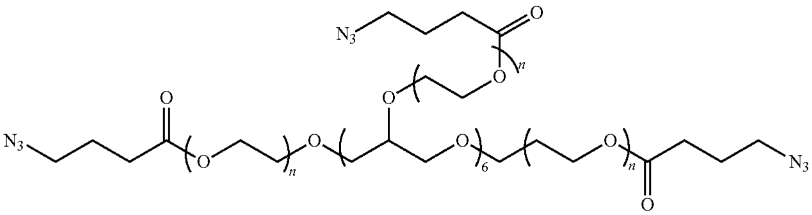 | PEG10000<br>PEG5000 |
| 29 | 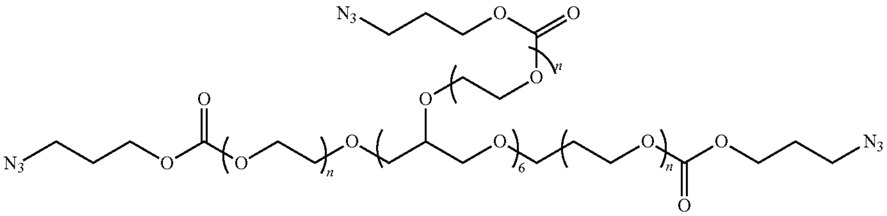 | PEG10000<br>PEG5000 |
| 30 | 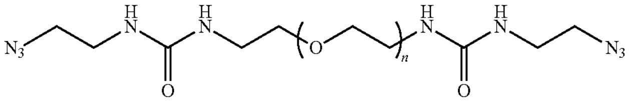 | PEG3000<br>PEG2000<br>PEG1000<br>PEG800<br>PEG400 |
| 31 | 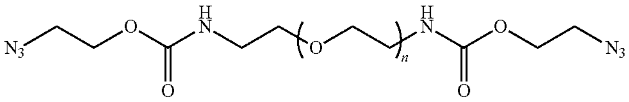 | PEG3000<br>PEG2000<br>PEG1000<br>PEG800<br>PEG400 |
| 32 | 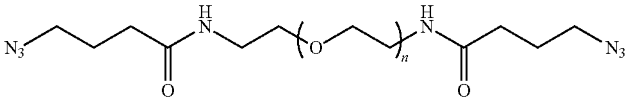 | PEG3000<br>PEG2000<br>PEG1000<br>PEG800<br>PEG400 |

TABLE 3-continued
| Ex. | Structure | MW of PEG used |
|---|---|---|
| 33 | 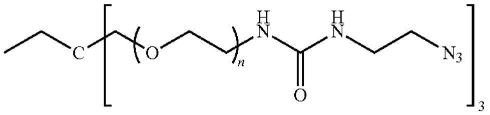 | PEG1000<br>PEG450 |
| 34 | 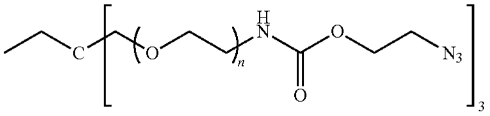 | PEG1000<br>PEG450 |
| 35 | 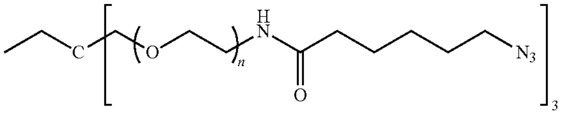 | PEG1000<br>PEG450 |
| 36 | 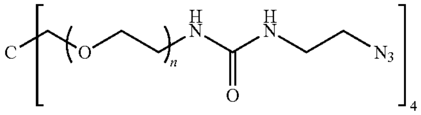 | PEG5000<br>PEG2000<br>PEG1000<br>PEG800 |
| 37 | 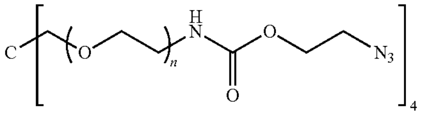 | PEG5000<br>PEG2000<br>PEG1000<br>PEG800 |
| 38 | 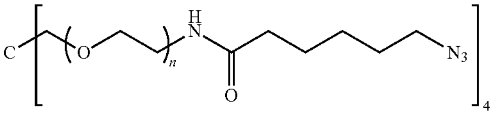 | PEG5000<br>PEG2000<br>PEG1000<br>PEG800 |
| 39 | 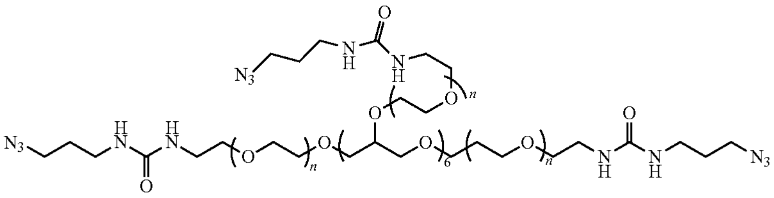 | PEG10000<br>PEG5000 |
| 40 | 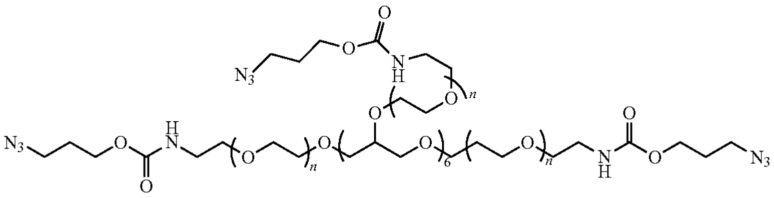 | PEG10000<br>PEG5000 |
| 41 | 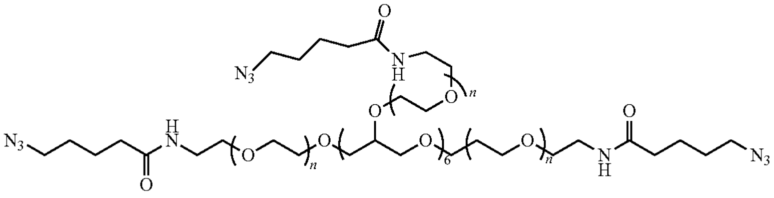 | PEG10000<br>PEG5000 |
| 42 | 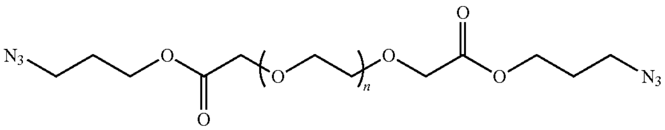 | PEG3000<br>PEG2000<br>PEG1000<br>PEG800<br>PEG400 |

TABLE 3-continued
| Ex. | Structure | MW of PEG used |
|---|---|---|
| 43 | 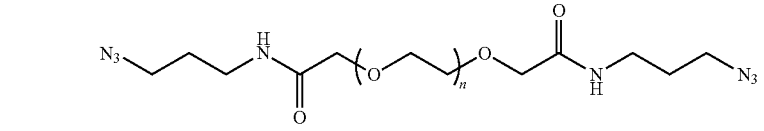 | PEG3000<br>PEG2000<br>PEG1000<br>PEG800<br>PEG400 |
| 44 | 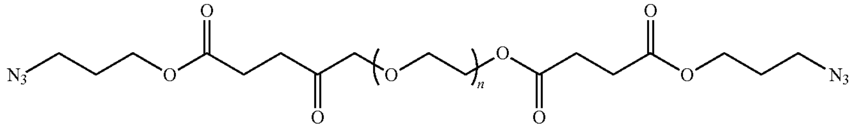 | PEG3000<br>PEG2000<br>PEG1000<br>PEG800<br>PEG400 |
| 45 | 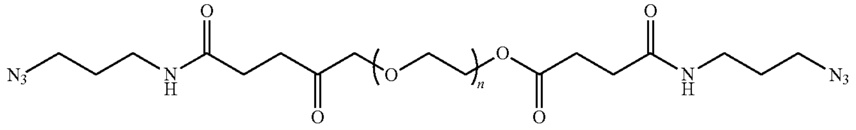 | PEG3000<br>PEG2000<br>PEG1000<br>PEG800<br>PEG400 |
| 46 | 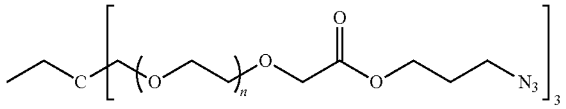 | PEG1000<br>PEG450 |
| 47 | 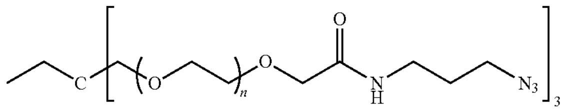 | PEG1000<br>PEG450 |
| 48 | 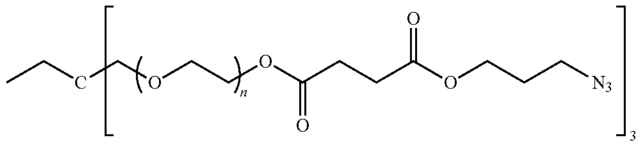 | PEG1000<br>PEG450 |
| 49 | 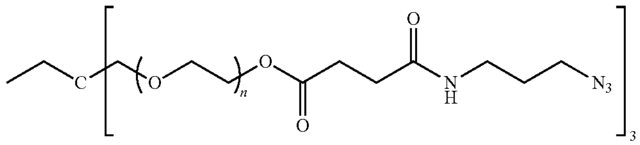 | PEG1000<br>PEG450 |
| 50 | 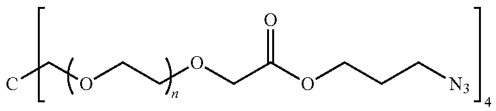 | PEG5000<br>PEG2000<br>PEG1000<br>PEG800 |
| 51 | 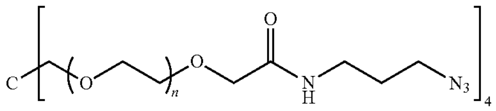 | PEG5000<br>PEG2000<br>PEG1000<br>PEG800 |
| 52 | 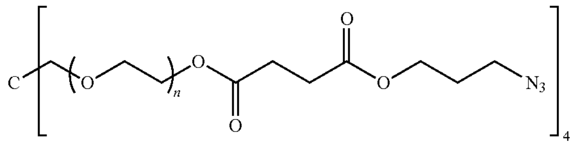 | PEG5000<br>PEG2000<br>PEG1000<br>PEG800 |
| 53 | 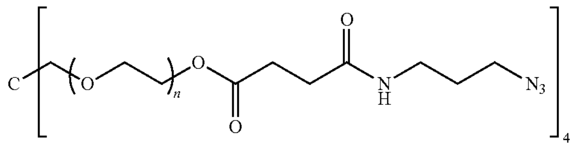 | PEG5000<br>PEG2000<br>PEG1000<br>PEG800 |

TABLE 3-continued
| Ex. | Structure | MW of PEG used |
|---|---|---|
| 54 | 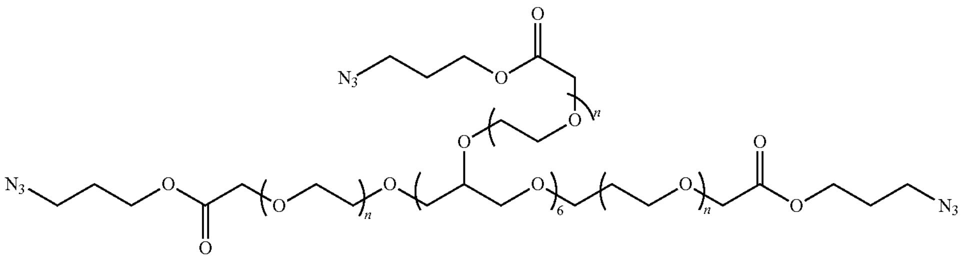 | PEG10000<br>PEG5000 |
| 55 | 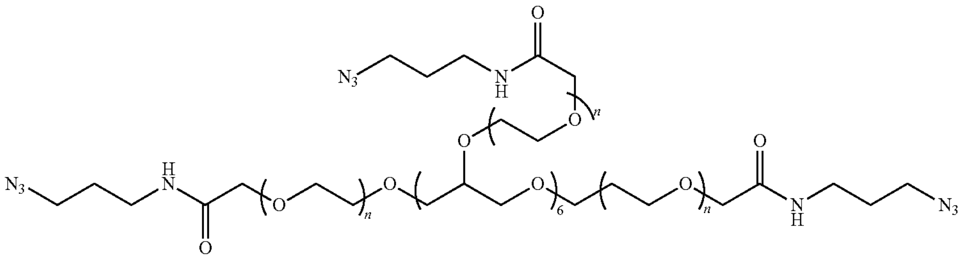 | PEG10000<br>PEG5000 |
| 56 | 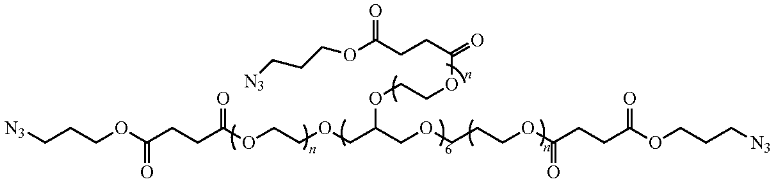 | PEG10000<br>PEG5000 |
| 57 | 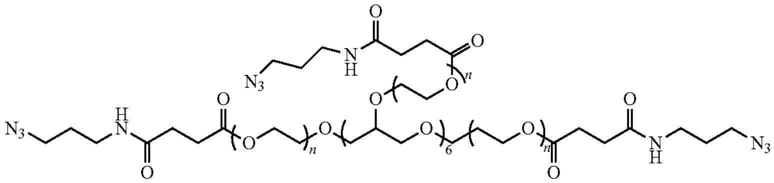 | PEG10000<br>PEG5000PEG450 |
| 58 | 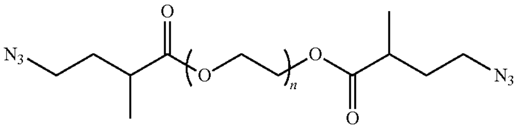 | PEG3000<br>PEG2000<br>PEG1000<br>PEG800<br>PEG400 |
| 59 | 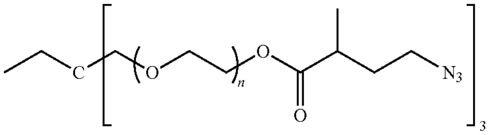 | PEG1000<br>PEG450 |
| 60 | 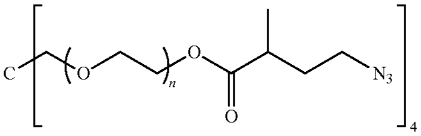 | PEG5000<br>PEG2000<br>PEG1000<br>PEG800 |

TABLE 3-continued
| Ex. | Structure | MW of PEG used |
|---|---|---|
| 61 | 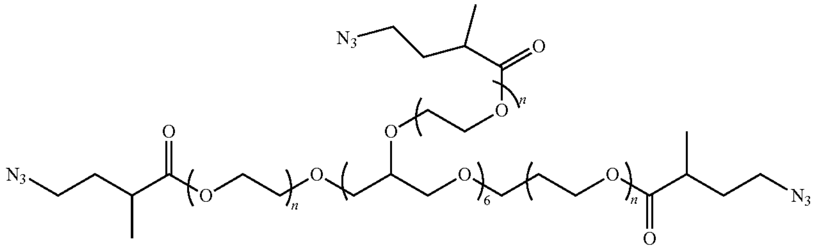 | PEG10000<br>PEG5000 |
| 62 | 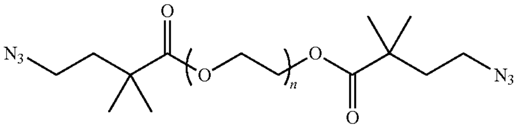 | PEG3000<br>PEG2000<br>PEG1000<br>PEG800<br>PEG400 |
| 63 | 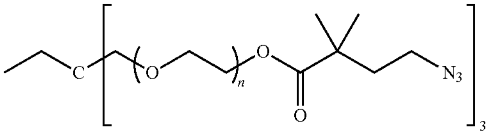 | PEG1000<br>PEG450 |
| 64 | 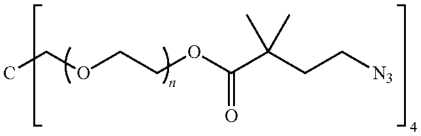 | PEG5000<br>PEG2000<br>PEG1000<br>PEG800 |
| 65 | 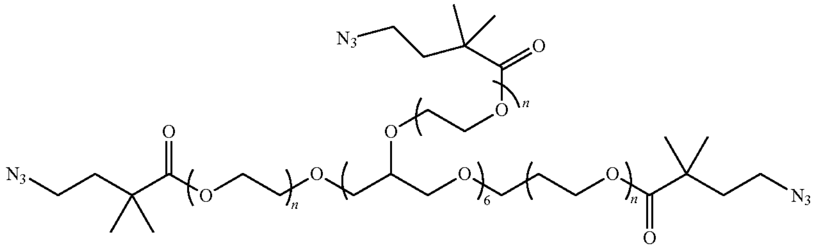 | PEG10000<br>PEG5000 |
| 66 | 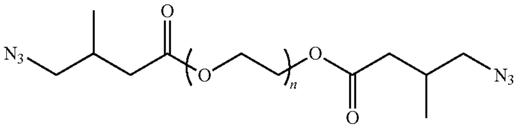 | PEG3000<br>PEG2000<br>PEG1000<br>PEG800<br>PEG400 |
| 67 | 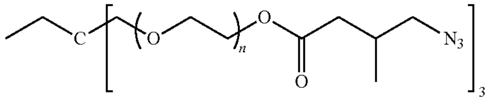 | PEG1000<br>PEG450 |
| 68 | 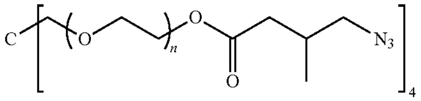 | PEG5000<br>PEG2000<br>PEG1000<br>PEG800 |
| 69 | 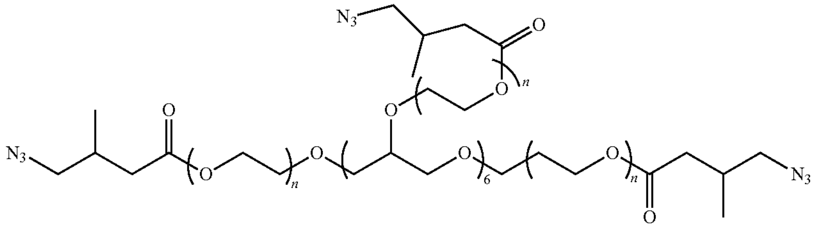 | PEG10000<br>PEG5000 |

TABLE 3-continued
| Ex. | Structure | MW of PEG used |
|---|---|---|
| 70 | 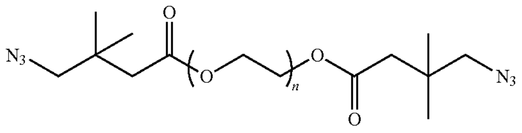 | PEG3000<br>PEG2000<br>PEG1000<br>PEG800<br>PEG400 |
| 71 | 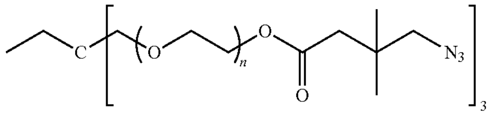 | PEG1000<br>PEG450 |
| 72 | 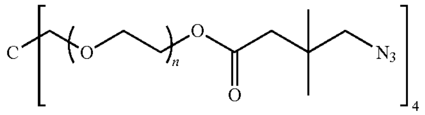 | PEG5000<br>PEG2000<br>PEG1000<br>PEG800 |
| 73 | 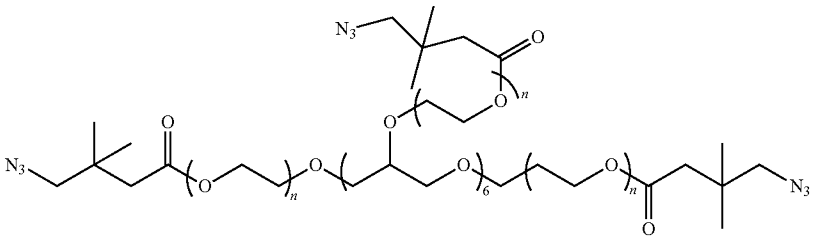 | PEG10000<br>PEG5000 |
| 74 | 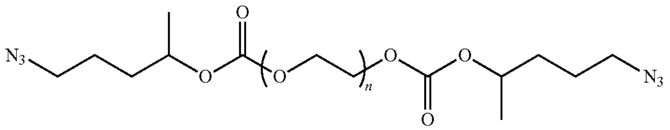 | PEG3000<br>PEG2000<br>PEG1000<br>PEG800<br>PEG400 |
| 75 | 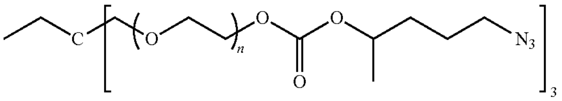 | PEG1000<br>PEG450 |
| 76 | 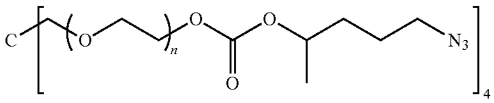 | PEG5000<br>PEG2000<br>PEG1000<br>PEG800 |
| 77 | 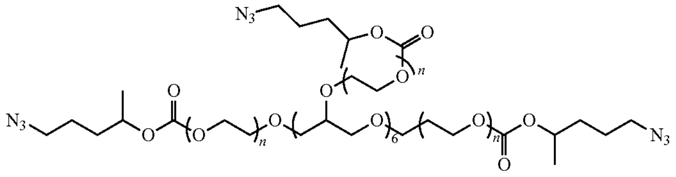 | PEG10000<br>PEG5000 |
| 78 | 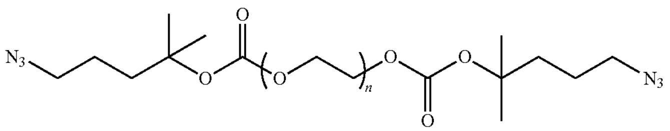 | PEG3000<br>PEG2000<br>PEG1000<br>PEG800<br>PEG400 |
| 79 | 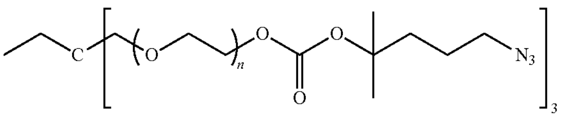 | PEG1000<br>PEG450 |
| 80 | 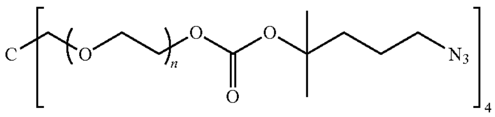 | PEG5000<br>PEG2000<br>PEG1000<br>PEG800 |

TABLE 3-continued

| Ex. | Structure | MW of PEG used |
|---|---|---|
| 81 | 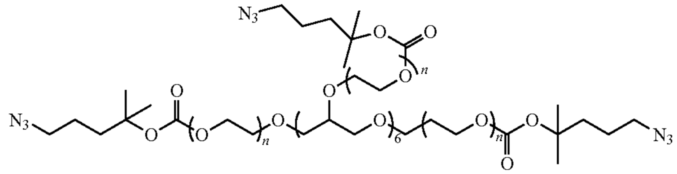 | PEG10000<br>PEG5000 |

Preparation of Drug-Polymer Conjugates

Polymer Synthesis

Linear Polytriazole Synthesis

Method 6: Copper (II)

The dialkyne-drug-monomer (1.0 eq), a diazide co-monomer (1.0 eq) and sodium ascorbate (0.45 eq) were placed into a vial fitted with a stirrer bar and then sealed with a Suba-Seal®. Anhydrous DMF pre-purged with $N_2$ or argon was introduced into the vial and the mixture was stirred to form a clear solution under constant flow of inert atmosphere. An amount of catalyst stock solution (CuBr2 (14.2 mg) and PMDETA (11.0 mg) in 2 mL of DMF) was added into the mixture to give 0.15 eq of $CuBr_2$ and 0.15 eq. PMDETA in the final reaction mixture. The solution was stirred for 24 hours at room temperature under constant flow of $N_2$. At the end of the reaction, the solution was diluted with THF and passed through a column of neutral alumina. The column was washed further with THF followed by DCM to collect the remaining polymers. The solution was then concentrated to around 1 mL and then precipitated into diethyl ether to give the desired polymer upon drying in vacuo.

Method 7: Copper (I)

The dialkyne-drug-monomer (1 eq) and diazide co-monomer (1 eq) were placed into a 4 mL vial fitted with a stirrer bar and then sealed with a Suba-Seal®. 0.5 mL of toluene pre-purged with $N_2$ was introduced into the vial and the mixture was stirred to form a clear solution under constant flow of $N_2$. 0.2 mL of CuBr (0.15 eq) and PMDETA (0.15 eq) stock solution (20 mg/mL in toluene, stirred for 30 minutes under $N_2$ prior to use) was subsequently added into the reaction mixture and the solution was stirred for 24 hours, at room T under constant flow of $N_2$. At the end of the reaction, the solution was diluted with 3 mL of THF and passed through a column of neutral alumina. The column was washed further with 20 mL of THF to ensure all polymer were collected. The solution was then concentrated to around 1 mL and then precipitated into 40 mL of diethyl ether and dried in vacuo.

Method 8: Ruthenium catalysed click reaction

The dialkyne-drug-monomer (1 eq), diazide comonomer (1 eq), and DMF were introduced into vial with a stirrer bar and then sealed with a Suba-Seal®. The solution was purged for 10 minutes with Argon before 14.7 mg of Cp*RuCl$(PPh_3)_2$ was added and the reaction heated at 35° C. under Argon for 24 hours. The reaction mixture was added dropwise to ethyl ether to precipitate the product before being dried in vacuo overnight.

Cross Linked Polytriazole Synthesis

Method 9: Cross-linked or hyper-branched hydrogel

The dialkyne-drug-monomer (1 eq), a tetra-azide co-monomer (0.5 eq) or a tri-azide co-monomer (0.66 eq), Na ascorbate (0.45 eq) and DMF were introduced into a vial equipped with a magnetic stirrer bar. Catalyst stock solution (CuBr2 (14.2 mg) and PMDETA (11.0 mg) in 2 mL of DMF) was added into the mixture to give 0.15 eq of CuBr2 and 0.15 eq. PMDETA (in the final reaction mixture. The vial was sealed with a rubber septum, stirred at room temperature under nitrogen for 24 h. The resulting gel was dialysed in acetonitrile (3×1 L) and dried under high vacuum.

Method 10: Cross-linked rods and bulk gels synthesis

The dialkyne-drug-monomer (1 eq), a tetra-azide co-monomer (0.5 eq) or a triazide co-monomer (0.66 eq), Na ascorbate (0.45 eq) and DMF were introduced into a vial equipped with a magnetic stirrer bar and PTFE tubes (Ø=0.35 mm, I=10 mm, 100 tubes). Catalyst stock solution ($CuBr_2$ (14.2 mg) and PMDETA (11.0 mg) in 2 mL of DMF) was added into the mixture to give 0.15 eq. of $CuBr_2$ and 0.15 eq. PMDETA in the final reaction mixture. The vial was sealed with a rubber septum, and degassing cycle (5 times nitrogen/vacuum cycles) were done to remove the bubbles trapped inside the tubes. The solution was subsequently stirred at room temperature under nitrogen for 24 h during which time gels formed. The tubes were separated from the bulk gels and soaked in isopropanol for minimum 16 hours and the rods were pushed out from the tubes using 0.305 mm stylet/wire. The resulting rods were washed in acetonitrile (3×250 mL) and the bulk gels with 3×1 L acetonitrile for 24 hours and dried under high vacuum.

Method 11: Cross-linked or hyper-branched hydrogel-Ruthenium catalysed Dialkyne-drug-monomer ((1 eq.), tetra-azide comonomer (0.5 eq), and DMF were introduced into a vial with a stirrer bar and then sealed with a Suba-Seal®. The mixture was then purged with Argon for 5 minutes before Cp*RuCl$(PPh_3)_2$ catalyst was added. The mixture was heated at 35° C. under Argon for 24 hours-before the temperature was raised to 50° C. for a second 24 hours. The resulting gel was dialysed in acetonitrile (3×1 L) and dried in vacuo overnight.

Method 12: Cross-linked rods and bulk gels synthesis containing 2 different cross-linkers The dialkyne-drug-monomer (1 eq), a tetra-azide co-monomer 1 (0.25 eq) and another tetra-azide co-monomer 2 (0.25 eq), Na ascorbate (0.45 eq) and DMF were introduced into a vial equipped with a magnetic stirrer bar and PTFE tubes (Ø=0.35 mm, I=10 mm, 100 tubes). Catalyst stock solution (CuBr2 (14.2 mg) and PMDETA (11.0 mg) in 2 mL of DMF) was added into the mixture to give 0.15 eq. of CuBr2 and 0.15 eq. PMDETA in the final reaction mixture. The vial was sealed with a rubber septum, and degassing cycle (5 times nitrogen/vacuum cycles) were done to remove the bubbles trapped inside the tubes. The solution was subsequently stirred at room temperature under nitrogen for 24 h to form gels. The tubes were separated from the bulk gels and soaked in isopropanol for minimum 16 hours and the rods were pushed out from the tubes using 0.305 mm stylet/wire. The resulting rods were washed in acetonitrile (3×250 mL) and the bulk gels with 3×1 L acetonitrile for 24 hours and dried under high vacuum.

Method 13: Cross-linked or hyper-branched hydrogel containing two different drug-monomers Dialkyne-drug-monomer (1) (0.5 eq), and dialkyne-drug-monomer (2) (0.5 eq), a tetra-azide co-monomer (0.5 eq) or a tri-azide co-monomer (0.66 eq), Na ascorbate (0.45 eq) and DMF (were introduced in a vial equipped with a magnetic stirring bar. Catalyst stock solution (CuBr2 (14.2 mg) and PMDETA (11.0 mg) in 2 mL of DMF) was added into the mixture to give 0.15 eq of CuBr2 and 0.15 eq. PMDETA in the final reaction mixture. The vial was sealed with a rubber septum, stirred at room temperature under nitrogen for 24 h. The gel was dialysed in acetonitrile (3×1 L) and dried under high vacuum.

Method 14: Polymer conjugate prepared with diazide-drug-monomer.

The diazide-drug-monomer (1 eq.) and a dialkyne co-monomer (1 eq.) are dissolved in the solvent of choice. The solution is purged with argon for 30 minutes before copper (II) bromide ($CuBr_2$) (0.05 mol eq.), PMDETA (0.05 mol eq.) and sodium ascorbate (0.15 mol eq.) are added into the solution. The heterogeneous mixture is stirred vigorously overnight at room temperature until complete consumption of starting materials, as indicated by TLC. The mixture is diluted with water and any precipitate that forms is collected. Purification of the product by precipitation from DMF and further purification on Sephadex LH-20 gives the title drug-polymer conjugate. The drug-polymer conjugates are analysed by IR, $^1H$ NMR and $^{13}C$ NMR and GPC Method 15: Linear click polymer conjugate prepared with dialkyne-drug-monomer with additives.

The dialkyne-drug-monomer and diazide co-monomer 1 and co-monomer 2 are dissolved in the solvent of choice while keeping an equimolar ratio between the number of alkyne units and azide units. The solution is purged with argon for 30 minutes before copper (II) bromide ($CuBr_2$) (0.05 mol eq.), PMDETA (0.05 mol eq.) and sodium ascorbate (0.15 mol eq.) are added into the solution. The heterogeneous mixture is stirred overnight under argon atmosphere and at room temperature for 24 hours. The reaction mixture is then passed through a column of basic alumina to remove the $CuBr_2$ catalyst, and then concentrated in vacuo before being precipitated several times in excess of diethyl ether to afford the desired polymer a solid. The drug-polymer conjugates are analysed by $^1H$ NMR and GPC.

Method 16: Polymer conjugate prepared with alkyne-azide-drug-agent conjugate monomer (drug monomer only)

The alkyne-azide drug-monomer (1 eq.) is dissolved in the solvent of choice. The solution is purged with argon for 30 minutes before copper (II) bromide ($CuBr_2$) (0.05 mol eq.), PMDETA (0.05 mol eq.) and sodium ascorbate (0.15 mol eq.) are added into the solution. The heterogeneous mixture is stirred vigorously overnight until complete consumption of starting materials, as indicated by TLC. The mixture is diluted with water and any precipitate that forms is collected. Purification of the product by precipitation from DMF and further purification on Sephadex LH-20 gives the title drug-polymer conjugate. The drug-polymer conjugates are analysed by IR, $^1H$ NMR and $^{13}C$ NMR and GPC.

Method 17: Polymer conjugate prepared with alkyne-azide-drug-monomer (and co-monomer)

The alkyne-azide-drug-monomer (1 eq.) and an alkyne-azide co-monomer (1 eq.) are dissolved in the solvent of choice. The solution is purged with argon for 30 minutes before copper (II) bromide ($CuBr_2$) (0.05 mol eq.), PMDETA (0.05 mol eq.) and sodium ascorbate (0.15 mol eq.) are added into the solution. The heterogeneous mixture is stirred vigorously overnight until complete consumption of starting materials, as indicated by TLC. The mixture is diluted with water and any precipitate that forms is collected. Purification of the product by precipitation from DMF and further purification on Sephadex LH-20 gives the title drug-polymer conjugate. The drug-polymer conjugates are analysed by IR, $^1H$ NMR and $^{13}C$ NMR and GPC.

Using the methods described above the following polymers of Table 4 can be prepared.

TABLE 4

| Example | Drug-monomer 1 (eq) | Co-Monomer 1 (eq) | Co-Monomer 2 (eq) | Production Method |
|---|---|---|---|---|
| 82 | Example 3 (1 eq.) | Example 19 (1 eq.) | — | 6 |
| 83 | Example 3 (1 eq.) | Example 20 (1 eq.) | — | 6 |
| 84 | Example 3 (3 eq.) | Example 22 (2 eq.) | — | 9 |
| 85 | Example 3 (3 eq.) | Example 23 (2 eq.) | — | 9 |
| 86 | Example 3 (1 eq.) | Example 25 (0.5 eq.) | — | 10 |
| 87 | Example 3 (1 eq.) | Example 26 (0.5 eq.) | — | 10 |
| 88 | Example 3 (1 eq.) | Example 28 (0.125 eq.) | — | 9 |
| 89 | Example 3 (1 eq.) | Example 25 (0.25 eq.) | Example 16 (0.25 eq.) | 12 |
| 90 | Example 3 (1 eq.) | Example 25 (0.25 eq.) | Example 24 (0.25 eq.) | 12 |
| 91 | Example 4 (1 eq.) | Example 14 (1 eq.) | | 6 |
| 92 | Example 4 (1 eq.) | Example 18 (1 eq.) | | 6 |
| 93 | Example 4 (3 eq.) | Example 15 (2 eq.) | | 9 |
| 94 | Example 4 (3 eq.) | Example 21 (2 eq.) | | 9 |
| 95 | Example 4 (1 eq.) | Example 16 (0.25 eq.) | | 10 |
| 96 | Example 4 (1 eq.) | Example 24 (0.25 eq.) | | 10 |
| 97 | Example 4 (1 eq.) | Example 17 (0.125 eq.) | | 9 |
| 98 | Example 4 (1 eq.) | Example 16 (0.25 eq.) | Example 24 (0.25 eq.) | 12 |
| 99 | Example 4 (1 eq.) | Example 16 (0.25 eq.) | Example 25 (0.25 eq.) | 12 |
| 100 | Example 4 (1 eq.) | Example 24 (0.25 eq.) | Example 25 (0.25 eq.) | 12 |
| 101 | Example 5 (1 eq.) | Example 19 (1 eq.) | — | 6 |
| 102 | Example 5 (1 eq.) | Example 20 (1 eq.) | — | 6 |
| 103 | Example 5 (3 eq.) | Example 22 (2 eq.) | — | 9 |
| 104 | Example 5 (3 eq.) | Example 23 (2 eq.) | — | 9 |
| 105 | Example 5 (1 eq.) | Example 25 (0.5 eq.) | — | 10 |
| 106 | Example 5 (1 eq.) | Example 26 (0.5 eq.) | — | 10 |
| 107 | Example 5 (1 eq.) | Example 28 (0.125 eq.) | — | 9 |
| 108 | Example 5 (1 eq.) | Example 25 (0.25 eq.) | Example 16 (0.25 eq.) | 12 |
| 109 | Example 5 (1 eq.) | Example 25 (0.25 eq.) | Example 24 (0.25 eq.) | 12 |
| 110 | Example 5 (1 eq.) | Example 64 (0.25 eq.) | Example 16 (0.25 eq.) | 12 |

TABLE 4-continued

| Example | Drug-monomer 1 (eq) | Co-Monomer 1 (eq) | Co-Monomer 2 (eq) | Production Method |
|---|---|---|---|---|
| 111 | Example 5 (1 eq.) | Example 64 (0.25 eq.) | Example 24 (0.25 eq.) | 12 |
| 112 | Example 6 (1 eq.) | Example 14 (1 eq.) | — | 6 |
| 113 | Example 6 (1 eq.) | Example 18 (1 eq.) | — | 6 |
| 114 | Example 6 (3 eq.) | Example 15 (2 eq.) | — | 9 |
| 115 | Example 6 (3 eq.) | Example 21 (2 eq.) | — | 9 |
| 116 | Example 6 (1 eq.) | Example 16 (0.5 eq.) | — | 10 |
| 117 | Example 6 (1 eq.) | Example 24 (0.5 eq.) | — | 10 |
| 118 | Example 6 (1 eq.) | Example 17 (0.125 eq.) | — | 9 |
| 119 | Example 6 (1 eq.) | Example 16 (0.25 eq.) | Example 24 (0.25 eq.) | 12 |
| 120 | Example 6 (1 eq.) | Example 16 (0.25 eq.) | Example 25 (0.25 eq.) | 12 |
| 121 | Example 6 (1 eq.) | Example 24 (0.25 eq.) | Example 25 (0.25 eq.) | 12 |
| 122 | Example 7 (1 eq.) | Example 14 (1 eq.) | — | 6 |
| 123 | Example 7 (1 eq.) | Example 18 (1 eq.) | — | 6 |
| 124 | Example 7 (3 eq.) | Example 15 (2 eq.) | — | 9 |
| 125 | Example 7 (3 eq.) | Example 21 (2 eq.) | — | 9 |
| 126 | Example 7 (1 eq.) | Example 16 (0.5 eq.) | — | 10 |
| 127 | Example 7 (1 eq.) | Example 24 (0.5 eq.) | — | 10 |
| 128 | Example 7 (1 eq.) | Example 17 (0.125 eq.) | — | 9 |
| 129 | Example 7 (1 eq.) | Example 16 (0.25 eq.) | Example 24 (0.25 eq.) | 12 |
| 130 | Example 7 (1 eq.) | Example 16 (0.25 eq.) | Example 25 (0.25 eq.) | 12 |
| 131 | Example 7 (1 eq.) | Example 24 (0.25 eq.) | Example 25 (0.25 eq.) | 12 |
| 132 | Example 9 (1 eq.) | Example 14 (1 eq.) | — | 6 |
| 133 | Example 9 (1 eq.) | Example 18 (1 eq.) | — | 6 |
| 134 | Example 9 (1 eq.) | Example 19 (1 eq.) | — | 6 |
| 135 | Example 9 (3 eq.) | Example 15 (2 eq.) | — | 9 |
| 136 | Example 9 (3 eq.) | Example 21 (2 eq.) | — | 9 |
| 137 | Example 9 (3 eq.) | Example 22 (2 eq.) | — | 9 |
| 138 | Example 9 (1 eq.) | Example 16 (0.5 eq.) | — | 10 |
| 139 | Example 9 (1 eq.) | Example 24 (0.5 eq.) | — | 10 |
| 140 | Example 9 (1 eq.) | Example 25 (0.5 eq.) | — | 10 |
| 141 | Example 9 (1 eq.) | Example 26 (0.5 eq.) | — | 10 |
| 142 | Example 9 (1 eq.) | Example 17 (0.125 eq.) | — | 9 |
| 143 | Example 9 (1 eq.) | Example 16 (0.25 eq.) | Example 24 (0.25 eq.) | 12 |
| 144 | Example 9 (1 eq.) | Example 16 (0.25 eq.) | Example 25 (0.25 eq.) | 12 |
| 145 | Example 9 (1 eq.) | Example 24 (0.25 eq.) | Example 25 (0.25 eq.) | 12 |

In a similar manner to Table 4 and using the methods described above and in WO 2018/165711 A1 the drug monomer examples described herein and the co-monomers described in Table 3 can be combined to prepare drug-polymer conjuges.

Drug Release Method

Polymer samples may be tested for in vitro drug release following guidelines recommended by the International Organisation of Standardisation. The samples are placed onto a wire mesh folded into an M shape and suspended in isotonic phosphate buffer (IPB) pH 7.4 or pH 8.4 (Table 1), and stirred at 37° C. or 55° C. Aliquots of the receptor solution are collected at pre-determined time points until the drug is depleted from the polymer.

In-vitro Release Sample Preparation 15 mL of isotonic phosphate buffer (pH 7.4) is added to approximately 10 mg of bulk polymer material and allowed to stir in a 37° C. water bath in the absence of light. 100 μL aliquots of each sample are removed at defined time points. 100 μL of isotonic phosphate buffer is replaced back into each sample after each aliquot removal. The amount of drug in the aliquots is quantified by reverse phase high performance liquid chromatography (HPLC) coupled with UV detection. Analytes are separated on a C18 column with a solvent mixture as outlined for each drug class.

Degradation Sample Preparation

In Vitro Degradation of Cross-Linked Polymers

A degradation sample consists of three to four rods of cross-linked polymer (total polymer mass=0.5 to 1.1 mg) is wrapped in a stainless-steel mesh, placed in an amber glass vial filled with 15 mL of isotonic phosphate buffer (pH 7.4) and equipped with a stir bar and a PTFE/silicone septum screw cap. The initial mass of both mesh and rods is recorded.

Ten to twelve of these samples may be placed in a thermostatted water bath at either 37° C. or 55° C., equipped with a multi-stirring plate. The samples are stirred at 300 rpm at the required temperature and a sample is removed at pre-determined time points. The polymer is removed from the sample and the mesh with the rods was washed twice with milliQ water and dried under vacuum. The rods are weighed. When rods can not be removed from the mesh (rods stuck), the mesh with rods may be weighed. In addition, the drug concentration of the buffer is measured by HPLC.

The amount of drug release from samples undergoing biodegradation can also be determined. 100 μL aliquots of each sample are removed at defined time points. The amount of drug in the aliquots is quantified by reverse phase high performance liquid chromatography (HPLC) coupled with UV detection, as outlined below.

In Vitro Degradation of Linear Polymers

A degradation sample consists of carefully weighed polymer (~10 mgs) placed in an 8 mL vial filled with 5 mL of isotonic phosphate buffer (pH 7.4) and equipped with a stir bar and a PTFE/silicone septum screw cap. Four to five samples of each polymer are placed in a thermostatted water bath at either 37° C. or 55° C., equipped with a multi-stirring plate. The samples are stirred at 300 rpm at the required temperature and a sample is removed at pre-determined time points. 100 μL aliquots are removed from each sample and the amount of drug in the aliquots quantified by reverse phase high performance liquid chromatography (HPLC) coupled with UV detection, as outlined below. The remaining solution is dried in a freeze dryer for 72 hours. Gel permeation chromatography (GPC) analysis is done on each sample to analyse the molecular weight of the polymer.

GPC Analysis:

Gel permeation chromatography (GPC) analysis of the polymer samples may be performed on Shimadzu liquid chromatography system equipped with a Shimadzu RID-10A differential refractive index detector (λ=633 nm) and Shimadzu SPD-20A ultraviolet detector connected to a 5.0 μm bead-size guard column (50×7.8 mm) followed by three Shodex KF-805L columns (300×8 mm, bead size: 10 μm, pore size maximum: 5000 Å) in series operating at 40° C. The eluent N,N-dimethylacetamide (HPLC grade, with 0.03% w/v LiBr) may be used running at 1 mL/min. A molecular weight calibration curve may be produced using polystyrene standards with narrow molecular weights distribution ranging from 500 to $2\times10^6$ Da.

The amount of drug release from samples undergoing biodegradation is also determined. 100 μL aliquots of each sample are removed at defined time points. The amount of drug in the aliquots may be quantified by reverse phase high performance liquid chromatography (HPLC) coupled with UV detection.

Example 146

The latanoprost conjugate of Examples 229 and 230 of WO2018165711 are used to model for release of the bicyclic prostaglandins from the polymer conjugate of the invention.

Drug-polymer conjugates of Example 229 and Example 230 were produced and each are a product of the respective drug monomers, sepatoprost free acid and Example 58, and 4-arm PEG500 azide,

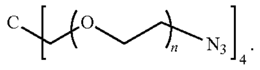

sepatoprost free acid and Example 58 both involve latanoprost free acid attached through an aryl ester to pyridoxine but with an ether Q-X functionality with increasing methylene chain length within Q-X.

TABLE 5

| Drug Monomer Example | Example 1 | Example 58 |
|---|---|---|
| Structure | 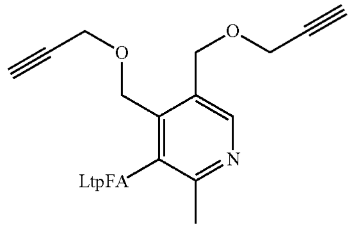 | 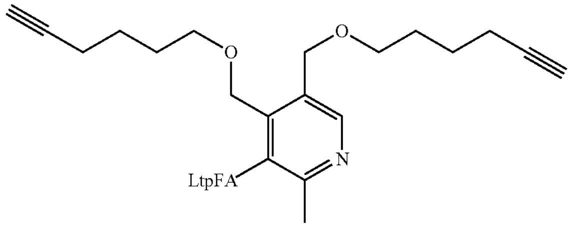 |

In both cases release there is no biodegradable moiety within the polymer of the construct, hence drug release is solely a function of hydrolysis of the linker (L) to release latanoprost free acid. A biodegradable polymer is not required to provide effective drug release. Example 229 has a shorter methylene chain within the Q-X moiety than Example 230. Release of latanoprost free acid is more rapid with Example 229 that Example 230, showing that changes to chemistry around an aryl ester linker (L) can be used to vary rate of drug release.

Example 147

Drug-polymer conjugates of Example 160, Example 173 and Example 170 of WO2018165711 demonstrate the effect on the backbone chemistry on the rate of degradation and clearance of the polymer from the site of injection of a polymer pellet. Each of polymers are a product of the respective drug monomers 4-arm PEG500 azide,

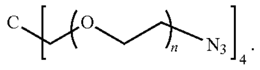

The drug monomer contains latanoprost free acid attached through an aryl ester to pyridoxine but with an ester Q-X functionality with increasing steric hindrance as shown in Table 6.

TABLE 6

| Drug Monomer Example | Example 160 | Example 173 | Example 170 |
|---|---|---|---|
| Structure | 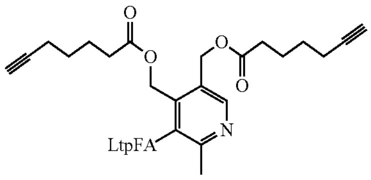 | 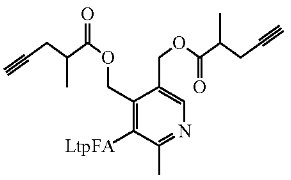 | 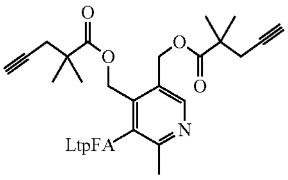 |

Figure 2:
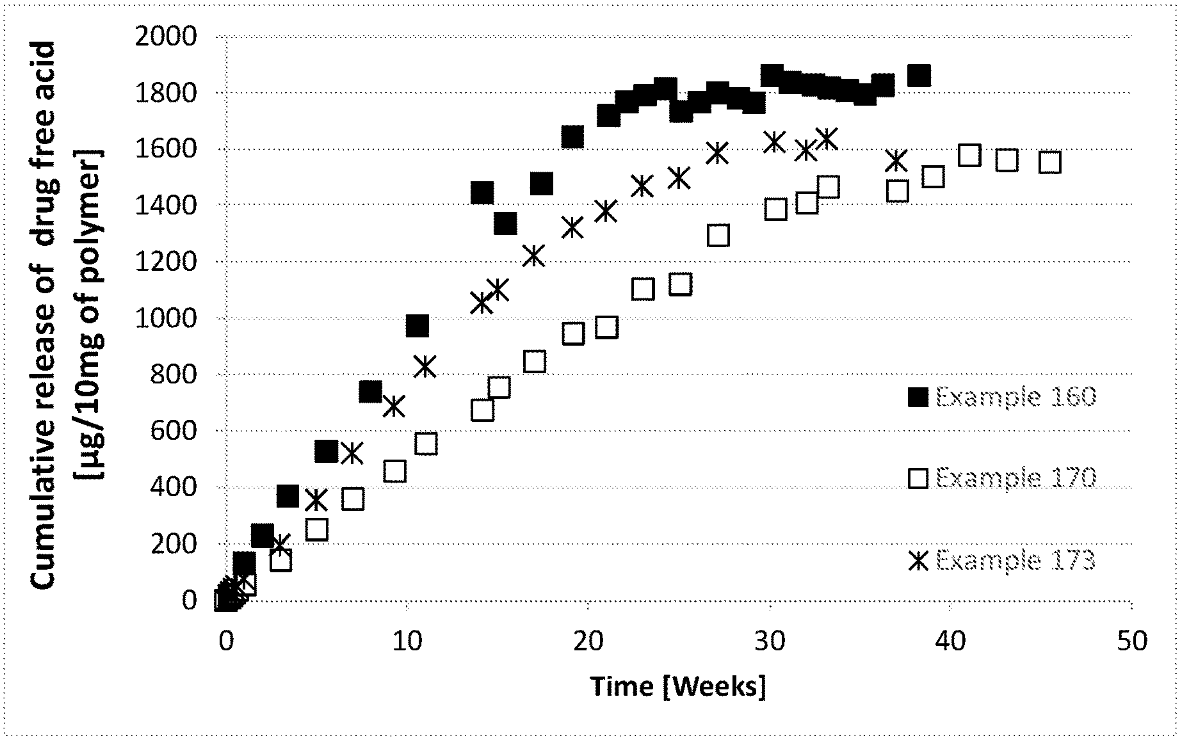
FIG. 2 includes two graphs relating to drug-polymer conjugates described in Example 147 which studies three polymer conjugated differing in the biodegradable backbone portion Q of the polymer conjugate and show the cumulative release (μg/10 mg) of the prostaglandin free acid.
Figure 3:
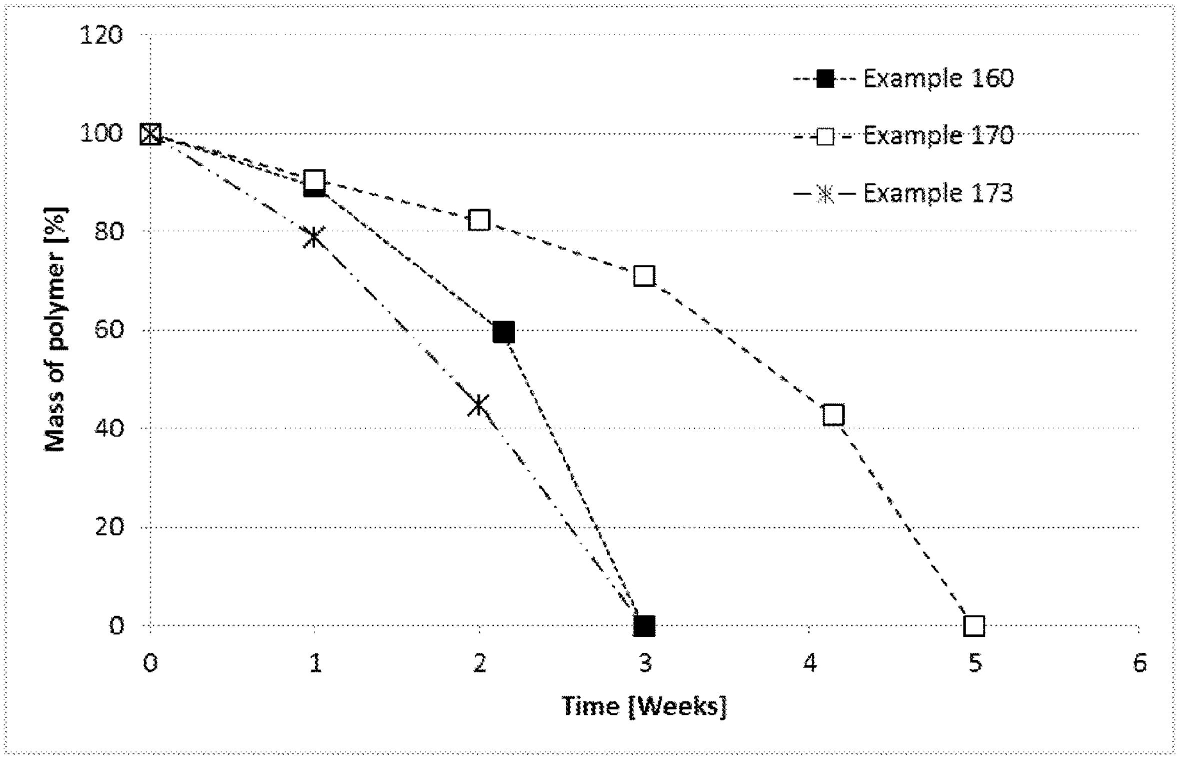
FIG. 3 includes two graphs relating to drug-polymer conjugates described in Example 147 which studies three polymer conjugated differing in the biodegradable backbone portion Q of the polymer conjugate and show the % mass loss with time exposed to isotonic phosphate buffer (pH 7.4) at 37.0° C. and 55.0° C., respectively, from drug-polymer conjugates.

The release rates do not vary significantly with changes to the Q-X moiety of the drug monomer (see FIG. 2, whereas, the period until complete mass loss does vary (see FIG. 3). Furthermore, the mass loss is non-linear with very little loss initially but accelerating after a lag period. Such a profile allows a product to be produced to ensure very little mass loss during its treatment period with rapid mass loss after the treatment period.

Figure 4:
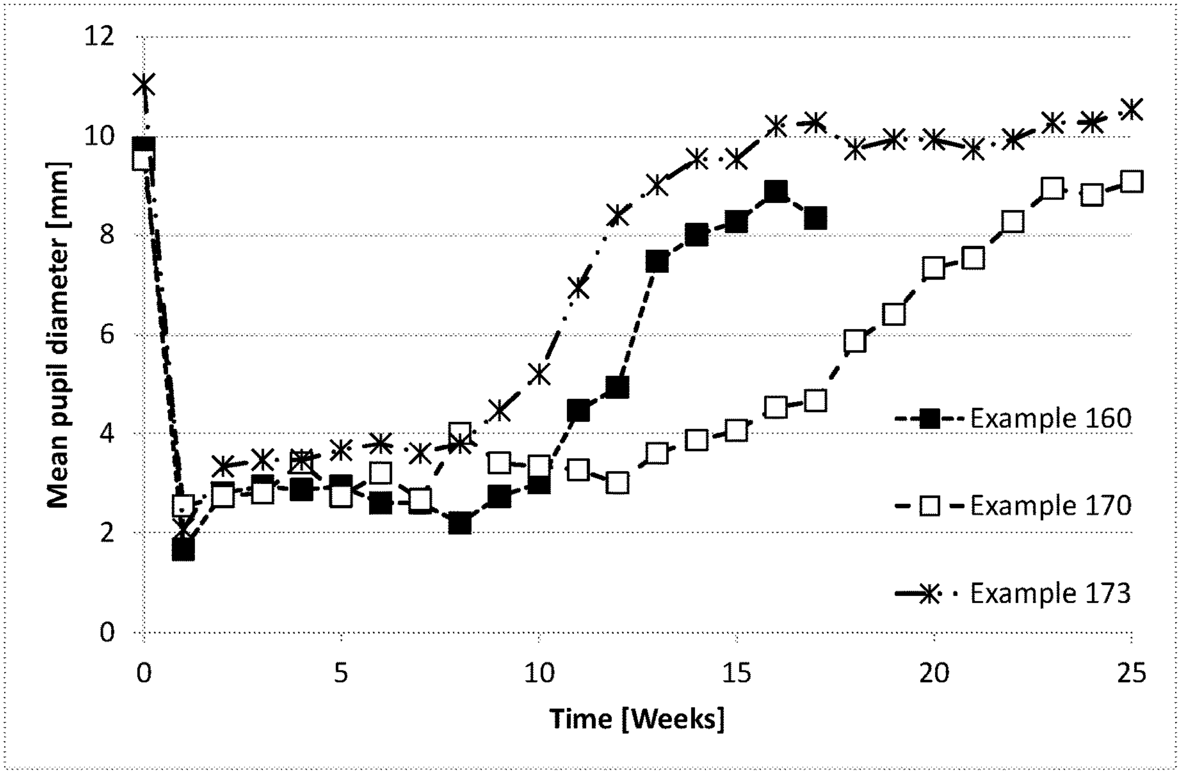
FIG. 4 is a graph having three plots showing the miotic pupil response (mm) with time in dog eyes treated with a rod-shaped ocular implant as described in Example 147.

In FIG. 4 the plots show the miotic pupil response (mm) in dog eyes treated with a rod-shaped ocular implant comprised of Example 160, Example 173 and Example 170. These results demonstrate therapeutic levels of drug (latanoprost free acid) are released. In this case the treatment period is determined by the biodegradation chemistry of Formula II, as complete implant mass loss (or implant biodegradation) occurs prior to any significant depletion of latanoprost free acid attached through the linker (L). The rate of drug release is shown to be the preferred near zero-order profile to provide a constant daily dose for the entire treatment period. Rod-shaped implants of Example 160, Example 173 and Example 170 were produced suitable for administration to dogs with a 27G needle. The implant was administered to the eye of the dog by means of an administration device fitted with a 27G needle that housed the implant. The needle was injected into the anterior chamber of the eye then the implant expelled from the needle by moving a stylet down the barrel of the needle towards the eye chamber. Pupil size (mm) was measured weekly by means of Vernier™ calipers. Dog pupils show a miotic response to a prostaglandin analogue. The pupil response was measured weekly following administration. In all three cases therapeutic concentrations of the prostaglandin analogue, latanoprost free acid, was shown to be released during the near-zero order release period as indicated by a pupil size less than 4 mm. The pupil response was shown to diminish at about 8 weeks, 11 weeks and 15 weeks, for Example 160, Example 173 and Example 170, respectively, which coincides with significant mass loss of each implant (refer FIG. 3). Such a result demonstrates that the chemistry of the Q-X moiety can be used to vary the treatment period of the product.

The invention claimed is:

1. A drug-polymer conjugate, which is a copolymer of:

(i) at least one monomer of formula (I):

(I)

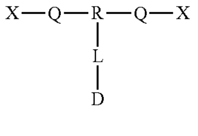

where:

X may be the same or different at each occurrence and represents a terminal functional group comprising an alkyne or an azide;

Q is independently selected at each occurrence and may be present or absent and when present, represents a linking group;

R is selected from the group consisting of linear or branched hydrocarbon, optionally substituted aryl, and optionally substituted heteroaryl;

D is a releasable bicyclic prostaglandin; and

L is a linker group;

and (ii) at least one co-monomer of formula (III):

$$J\text{-}(Y^1\text{-}A)_n \quad \text{(III)}$$

where:

J represents a linking functional group;

n is an integer from 2 to 8;

$Y^1$ comprises a polyether of formula $(OR^a)_m$ wherein each $R^a$ is independently selected from ethylene, propylene, and butylene, and m is an integer from 1 to 300, and the polyether is in chain with one or more groups selected from one or more of optionally substituted straight or branched $C_1$ to $C_{10}$ alkylene, amino, ether, ester, amide, carbonate, and carbamate; and A may be the same or different at each occurrence and represents a group comprising a terminal functional group comprising an alkyne or an azide functionality, wherein said terminal functional group is complementary to the terminal functional group X of formula (I) providing triazole moieties from reaction of X and A.

2. The drug-polymer conjugate of claim 1, wherein n is 3 or 4.

3. The drug-polymer conjugate of claim 1, wherein the bicyclic prostaglandin D is of formula (X):

(X)

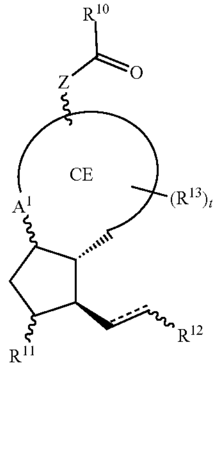

wherein:

CE is a 6 or 7 membered cyclic ether or cyclic thioether which may be saturated or include one double bond;

$A^1$ is oxygen or sulfur;

------ represents a double or single bond which is independently selected in each case;

$R^{12}$ is $C_{1-6}$ alkyl optionally substituted with 1 to 5 substituents selected from the group consisting of hydroxyl, oxo, halo, $C_{1-4}$ alkoxy, ring 2, —O-ring 2, and —S-ring 2, wherein ring 2 is selected from optionally substituted, aromatic or non-aromatic, carbocyclic and heterocyclic rings; and one of $R^{10}$, $R^{11}$, and $R^{12}$ is linked to the polymer backbone, wherein:

$R^{11}$ and $R^{12}$ when linked to the polymer backbone comprise the alcohol residue of an ester or carbonate linking group, and $R^{10}$ when linked to the polymer backbone forms the acid residue of an ester or anhydride linking group; and $R^{10}$ when not linked to the backbone is selected from the group consisting of —OH, —O($C_{1-6}$ alkyl), —O—($C_{1-6}$ alkyl)-O—$NO_2$, and —$NR^aR^b$, where $R^a$ and $R^b$ are each independently selected from the group consisting of H, $C_{1-6}$ alkyl, and $C_{1-4}$ alkylsulfonyl;

$R^{11}$ when not linked to the polymer backbone is hydroxyl or halo;

$R^{13}$ is selected from halo, $C_{1-4}$ alkyl, and $C_{1-4}$alkoxy;

t is 0, 1, or 2; and

Z is selected from the group consisting of:

—$(CH_2)_m$— wherein m is an integer from 1 to 10;

—$(CH_2)_n$—CH═CH— wherein n is an integer from 1 to 6;

—$(CH_2)_p$-$A^1$-$CH_2$— wherein $A^1$ is oxygen or sulfur and p is 1 to 4; and ring 1, wherein ring 1 is selected from optionally substituted, aromatic or non-aromatic, carbocyclic and heterocyclic rings.

4. The drug-polymer conjugate of claim 1, wherein the bicyclic prostaglandin D is of formula (Xa-1):

(Xa-1)

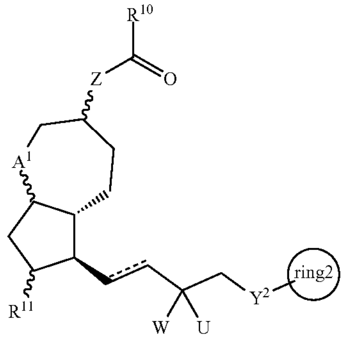

wherein:

$A^1$ is oxygen or sulfur;

------ represents a double or single bond;

W and U are selected from the group consisting of (i) where W and U together form oxo (═O), (ii) where W and U are each halo, and (iii) where W is $R^{15}$ and U is hydrogen;

one of $R^{10}$, $R^{11}$, and $R^{15}$ is linked to the polymer backbone, wherein:

$R^{11}$ and $R^{15}$ when linked to the polymer backbone are the alcohol residue of an ester or carbonate linking group and $R^1$ when linked to the polymer backbone forms the acid residue of an ester or anhydride linking group; and $R^{10}$ when not linked to the backbone is selected from the group consisting of —OH, —O($C_{1-6}$ alkyl), —O—($C_{1-6}$ alkyl)-O—$NO_2$, and —$NR^aR^b$, where $R^a$ and $R^b$ are each independently selected from the group consisting of H, $C_{1-6}$ alkyl, and $C_{1-4}$ alkylsulfonyl;

$R^{11}$ when not linked to the polymer backbone is hydroxy or halo;

when $R^{15}$ is not linked to the backbone then W is hydroxy and U is hydrogen, or W and U are each fluoro, or W and U together form oxo;

$Y^2$ is selected from —$CH_2$—, oxygen, and sulfur; and ring 2 is selected from optionally substituted, aromatic or non-aromatic carboxylic and heterocyclic rings;

Z is selected from the group consisting of:

—$(CH_2)_m$— wherein m is an integer from 1 to 10;

—$(CH_2)_n$—CH═CH— wherein n is an integer from 1 to 6;

—$(CH_2)_p$-$A^1$-$CH_2$— wherein $A^1$ is oxygen or sulfur and p is an integer from 1 to 4; and ring 1, wherein ring 1 is selected from optionally substituted, aromatic or non-aromatic, carbocyclic and heterocyclic rings.

5. The drug-polymer conjugate of claim 1, wherein the bicyclic prostaglandin D is of formula (Xa-2);

(Xa-2)

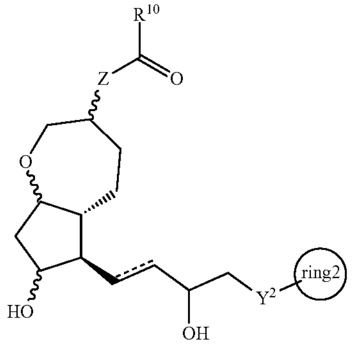

wherein:

$R^{10}$ is the bond to linker L and is-OH in the released bicyclic prostaglandin;

Z is selected from the group consisting of:

—$(CH_2)_m$— wherein m is an integer from 1 to 10;

—$(CH_2)_n$—CH═CH— wherein n is an integer from 1 to 6;

—$(CH_2)_p$-$A^1$-$CH_2$— wherein $A^1$ is oxygen or sulfur and p is 1 to 4; and ring 1, wherein ring 1 is selected from optionally substituted, aromatic or non-aromatic, carbocyclic and heterocyclic rings;

------ represents a double or single bond;

$Y^2$ is selected from —$CH_2$—, oxygen or sulfur; and ring 2 is selected from optionally substituted, aromatic or non-aromatic, carbocyclic and heterocyclic rings.

6. The drug-polymer conjugate of claim 1, wherein the polymer backbone comprises a plurality of biodegradable groups of formula (II):

(II)

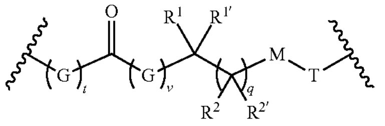

wherein:

G is independently selected at each occurrence from oxygen and $NR^{16}$ where $R^{16}$ is hydrogen or $C_1$ to $C_4$ alkyl;

each of t and v are independently 0 or 1 and at least one of t and v is 1;

$R^1$, $R^{1'}$, $R^2$, and $R^{2'}$ are independently selected from the group consisting of hydrogen, alkyl, alkoxy, and alkoxyalkyl, wherein one of the pairs of $R^1$, $R^{1'}$ and $R^2$, $R^{2'}$ may form a carbocycle or heterocycle of 3 to 6 constituent ring members wherein the heterocycle may comprise from 1 to 3 constituent oxygen heteroatom ring members; and M is selected from the group consisting of a bond, optionally substituted $C_1$ to $C_{10}$ straight or branched chain aliphatic, —O—($C_1$ to $C_{10}$ straight or branched chain aliphatic), an ether linking group comprising $C_1$ to $C_{10}$ straight or branched chain aliphatic interrupted by an oxygen (—O—), —N($R^w$)—($C_1$ to $C_{10}$ straight or branched chain aliphatic), and an amine linking group comprising $C_1$ to $C_{10}$ straight or branched chain aliphatic interrupted by N($R^w$), wherein $R^w$ is selected from hydrogen and $C_1$ to $C_4$ alkyl;

q is 0 or 1; and

T is a triazole moiety.

7. The drug-polymer conjugate of claim 1, wherein in formula (I) the Q is absent and the co-monomer of formula (III) comprises biodegradable groups.

8. The drug-polymer conjugate of claim 1, wherein Q is independently selected from the group consisting of:

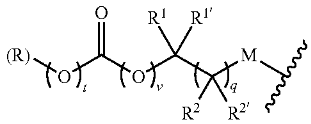

,

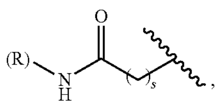

,

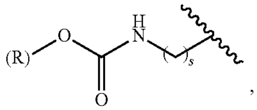

,

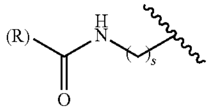

and

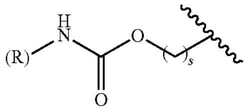

wherein:

(R) indicates the end attached to R and the opposite end is attached to X;

each of t and v are independently 0 or 1 and at least one of t and v is 1;

$R^1$, $R^{1'}$, $R^2$, and $R^{2'}$ are independently selected from the group consisting of hydrogen, alkyl, alkoxy, and alkoxyalkyl, wherein one of the pairs of $R^1$, $R^{1'}$ and $R^2$, $R^{2'}$ may form a carbocycle or heterocycle of 3 to 6 constituent ring members wherein the heterocycle may comprise from 1 to 3 constituent oxygen heteroatom ring members; and M is selected from the group consisting of a bond, optionally substituted $C_1$ to $C_{10}$ straight or branched chain aliphatic, —O—($C_1$ to $C_{10}$ straight or branched chain aliphatic), an ether linking group comprising $C_1$ to $C_{10}$ straight or branched chain aliphatic interrupted by an oxygen (—O—), —N($R^w$)—($C_1$ to $C_{10}$ straight or branched chain aliphatic), and an amine linking group comprising $C_1$ to $C_{10}$ straight or branched chain aliphatic interrupted by N($R^w$), wherein $R^w$ is selected from hydrogen and $C_1$ to $C_4$ alkyl;

q is 0 or 1; and s is an integer from 0 to 10.

9. The drug-polymer conjugate according to of claim 1, wherein the monomer of formula (I) is of formula (IV):

(IV)

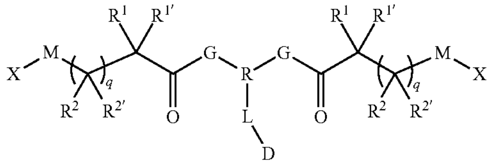

wherein

G is independently selected at each occurrence from oxygen and $NR^{16}$ where $R^{16}$ is hydrogen or $C_1$ to $C_4$ alkyl;

M is selected from the group consisting of a bond, optionally substituted $C_1$ to $C_{10}$ straight or branched chain aliphatic, —O—($C_1$ to $C_{10}$ straight or branched chain aliphatic), an ether linking group comprising $C_1$ to $C_{10}$ straight or branched chain aliphatic interrupted by an oxygen (—O—), —N($R^w$)—($C_1$ to $C_{10}$ straight or branched chain aliphatic), and an amine linking group comprising $C_1$ to $C_{10}$ straight or branched chain aliphatic interrupted by N($R^w$), wherein $R^w$ is selected from hydrogen and $C_1$ to $C_4$ alkyl;

X is a terminal functional group comprising an alkyne or an azide;

R is selected from the group consisting of linear or branched hydrocarbon, optionally substituted aryl, and optionally substituted heteroaryl;

L is a linker group; and

D is a releasable bicyclic prostaglandin;

$R^1$, $R^{1'}$, $R^2$, and $R^{2'}$ are independently selected from the group consisting of hydrogen, alkyl, alkoxy, alkoxyalkyl, amino, alkyl amino, dialkylamino, amino-alkyl, alkylamino-alkyl, and dialkylamino-alkyl, wherein one of the pairs of $R^1$,$R^{1'}$ and $R^2$,$R^{2'}$ may form a carbocycle or heterocycle of 3 to 6 constituent ring members wherein the heterocycle may comprise from 1 to 3 constituent heteroatom ring members selected from oxygen and nitrogen which nitrogen may optionally be substituted by $C_1$ to $C_6$ alkyl; and q is 0 or 1.

10. The drug-polymer conjugate of claim 1, wherein the co-monomer of formula (III) has the formula (IIIa):

$$J\text{-}((OR^a)_m\text{—}B\text{-}A)_n \qquad \text{(IIIa)}$$

wherein

A may be the same or different at each occurrence and represents a group comprising a terminal functional group comprising an alkyne or an azide functionality, wherein the alkyne or azide functionality in the terminal functional group is complementary to the alkyne or azide functionality in a terminal functional group X present on a monomer of formula (I);

J represents a bond, oxygen, or linking functional group, $R^a$ is selected from ethylene, propylene, butylene, and mixtures thereof;

m is an integer from 1 to 300;

n is an integer from 3 to 8;

B is selected from a bond, oxygen, -MOC(O)N(H)M'-, -MOC(O)OM'-, -MC(O)NHM'-, and a group selected from (VIa), (VIb), (VIc), and (VId):

(VIa)

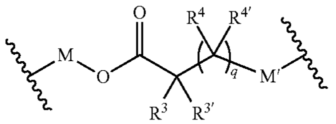

(VIb)

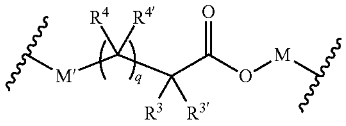

(VIc)

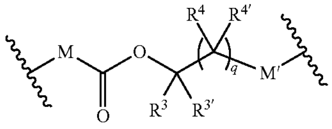

(VId)

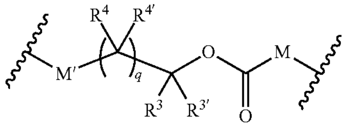

wherein M and M' are independently selected from the group consisting of a bond, optionally substituted $C_1$ to $C_{10}$ straight or branched chain aliphatic, —O—($C_1$ to $C_{10}$ straight or branched chain aliphatic), an ether linking group comprising $C_1$ to $C_{10}$ straight or branched chain aliphatic interrupted by an oxygen (—O—), —N($R^w$)—($C_1$ to $C_{10}$ straight or branched chain aliphatic), and an amine linking group comprising $C_1$ to $C_{10}$ straight or branched chain aliphatic interrupted by N($R^w$), wherein $R^w$ is selected from hydrogen and $C_1$ to $C_4$ alkyl;

q is 0 or 1;

wherein in the groups (VIa), (VIb), (VIc), and (VId), $R^3$, $R^{3'}$, $R^4$, and $R^{4'}$ are independently selected from the group consisting of hydrogen, alkyl, alkoxy, alkoxyalkyl, amino, alkyl amino, dialkylamino, amino-alkyl, alkylamino-alkyl, and dialkylamino-alkyl, wherein one of the pairs of $R^3$, $R^{3'}$ and $R^4$, $R^{4'}$ may form a carbocycle or heterocycle of 3 to 6 constituent ring members wherein the heterocycle may comprise from 1 to 3 constituent heteroatom ring members selected from oxygen and nitrogen which nitrogen may optionally be substituted by $C_1$ to $C_6$ alkyl.

11. The drug-polymer conjugate of claim 10, wherein J is a hydrocarbon of formula:

$$C_zH_{2z+2-n}$$

wherein z is an integer from 1 to 8 and n is an integer from 3 to 8.

12. The drug-polymer conjugate of claim 1, wherein n is an integer from 3 to 8 and J is selected from the group consisting of:

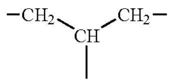

,

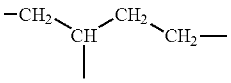

,

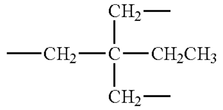

wherein n is 3; and

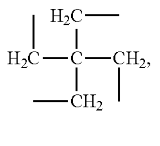

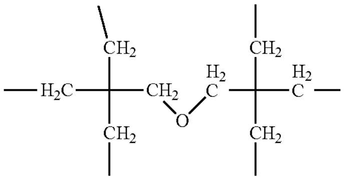

,

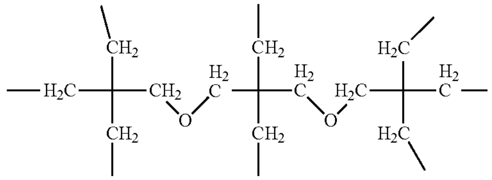

wherein n is an integer from 4, 6, or 8.

13. The drug-polymer conjugate of claim 1, wherein $(OR^a)_m$ is selected from poly(ethylene oxide), poly(propylene oxide), poly(butylene oxide), block copolymers of one or more of poly(ethylene oxide), poly(propylene oxide) and poly(butylene oxide), and block copolymers of two or more of poly(ethylene oxide), poly(propylene oxide) and poly (butylene oxide), wherein $(OR^a)_m$ has a molecular weight in the range of from 200 to 10,000.

14. The drug-polymer conjugate of claim 1, wherein the co-monomer of formula (III) is of formula (IIIa-1) or (IIIa-2);

(IIIa-1)

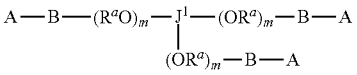

wherein $J^1$ is a straight or branched chain of formula $C_ZH_{2Z-1}$ and wherein z is an integer from 1 to 8; and (IIIa-2)

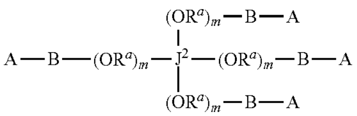

wherein $J^2$ is a straight or branched chain of formula $C_ZH_{2z-2}$ and wherein z is an integer from 1 to 8.

15. The drug-polymer drug conjugate of claim 6, wherein, $R^1$, $R^{1'}$, $R^2$, $R^{2'}$, $R^3$, $R^{3'}$, $R^4$, and $R^{4'}$ are selected from the group consisting of hydrogen, $C_1$ to $C_4$ alkyl, $C_1$ to $C_4$ alkoxy, and $C_1$ to $C_4$ alkoxy-substituted $C_1$ to $C_4$ alkyl.

16. The drug-polymer conjugate of claim 6, wherein at least one of $R^1$, $R^{1'}$, $R^2$, $R^{2'}$, $R^3$, $R^{3'}$, $R^4$, and $R^{4'}$ which is present is not hydrogen.

17. The drug-polymer drug conjugate of claim 1, wherein the monomer of formula (I) has the formula (IVa):

(IVa)

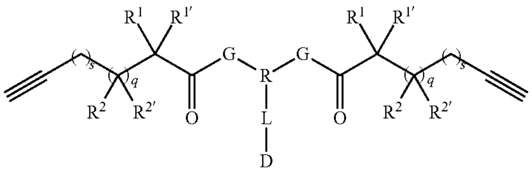

wherein:

G is independently selected at each occurrence from oxygen and $NR^{16}$ where $R^{16}$ is hydrogen or $C_1$ to $C_4$ alkyl;

L is a linker group;

D is a releasable bicyclic prostaglandin;

R is selected from the group consisting of linear or branched hydrocarbon, optionally substituted aryl, and optionally substituted heteroaryl;

$R^1$, $R^{1'}$, $R^2$, and $R^{2'}$ are independently selected from the group consisting of hydrogen, alkyl, alkoxy, alkoxy-alkyl, amino, alkyl amino, dialkylamino, amino-alkyl, alkylamino-alkyl, and dialkylamino-alkyl, wherein one of the pairs of $R^1$,$R^{1'}$ and $R^2$ $R^{2'}$ may form a carbocycle or heterocycle of 3 to 6 constituent ring members wherein the heterocycle may comprise from 1 to 3 constituent heteroatom ring members selected from oxygen and nitrogen which nitrogen may optionally be substituted by $C_1$ to $C_6$ alkyl;

q is 0 or 1;

s is an integer from 0 to 6; and in the co-monomer of formula (III), A is azide.

18. The drug-polymer conjugate of claim 1, wherein R is selected from the group consisting of straight and branched chain hydrocarbon of from 1 to 12 carbon atoms,

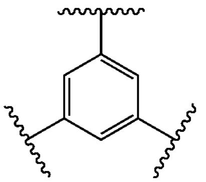
,
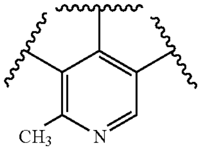
and

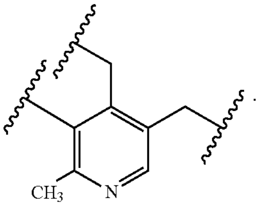
.

19. The drug-polymer conjugate of claim 1, wherein the linker group L is of a formula selected from the group consisting of:

(R) —O— (D);

(R) —OC(O)—Ar—O— (D);

(R) —NHC(O)—Ar—O— (D);

(R) —C(O)O—$C_{1-12}$alkylene-O— (D);

(R) —OC(O)O—$C_{1-12}$alkylene-O— (D);

(R) —OC(O)—$C_1$-$C_{12}$alkylene-O— (D);

(R) —OC(O)—O— (D);

(R) —OC(O)—Ar—OC(O) —O— (D);

(R) —NHC(O)—Ar—OC(O)—O (D);

(R) —C(O)O—$C_1$-$C_{12}$alkylene-OC(O)—O (D); and (R) —OC(O)—$C_1$-$C_{12}$alkylene-OC(O)— (D), wherein (R) indicates the end bonded to R and (D) indicates the end bonded to D.

20. A drug-polymer drug conjugate of claim 1, wherein the linker group L is of a formula selected from:

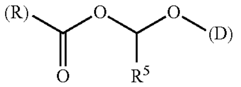
and
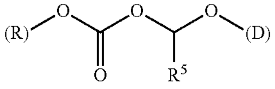

wherein $R^5$ is selected from the group consisting of hydrogen and $C_1$ to $C_6$ alkyl, and (R) indicates the end bonded to R and (D) indicates the end bonded to D.

21. The drug-polymer conjugate of claim 1, wherein the monomer of formula (I) is of formula (IVb):

(IVb)

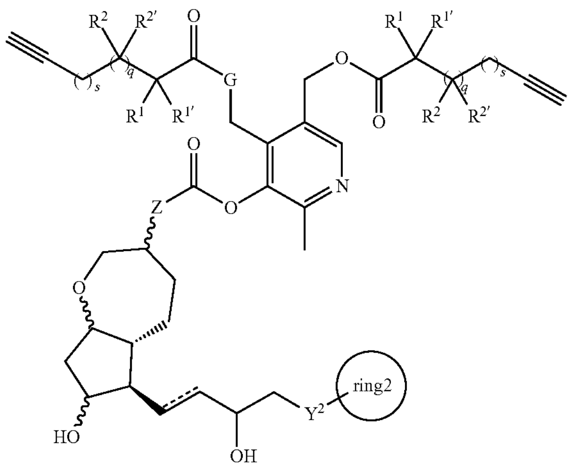

wherein:

G is oxygen or $NR^{16}$ where $R^{16}$ is hydrogen or $C_{1-4}$ alkyl;

$R^1$, $R^{1'}$, $R^2$, and $R^{2'}$ are independently selected from the group consisting of hydrogen, $C_1$ to $C_6$ alkyl, $C_1$ to $C_6$ alkoxy, and $C_1$ to $C_6$ alkoxy-($C_1$ to $C_6$ alkyl), wherein one of the pairs of $R^1$,$R^{1'}$ and $R^2$,$R^{2'}$ may form a carbocycle or heterocycle of 3 to 6 constituent ring members wherein the heterocycle may comprise from 1 to 3 constituent heteroatom ring members selected from oxygen and nitrogen which nitrogen may be substituted by $C_1$ to $C_6$ alkyl; and wherein at least one of $R^1$, $R^{1'}$, $R^2$, and $R^{2'}$ is other than hydrogen;

s is an integer from 0 to 6;

q is 0 or 1;

Z is selected from the group consisting of:

$-(CH_2)_m-$ wherein m is an integer from 1 to 10;

$-(CH_2)_n-CH{=}CH-$ wherein n is an integer from 1 to 6;

$-(CH_2)_p-A^1-CH_2-$ wherein $A^1$ is oxygen or sulfur and p is an integer from 1 to 4; and ring 1, wherein ring 1 is selected from optionally substituted, aromatic or non-aromatic, carbocyclic and heterocyclic rings;

------ represents a double or single bond;

$Y^2$ is selected from —$CH_2$—, oxygen, or sulfur; and ring 2 is selected from optionally substituted, aromatic or non-aromatic, carbocyclic and heterocyclic rings.

22. The drug-polymer conjugate of claim 1, wherein the monomer of formula (I) is of formula (IVc):

(IVc)

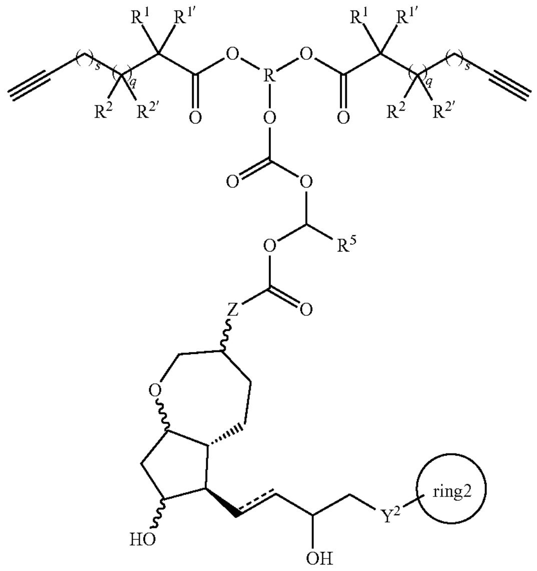

wherein $R^1$, $R^{1'}$, $R^2$, and $R^{2'}$ are independently selected from the group consisting of hydrogen, $C_1$ to $C_6$ alkyl, $C_1$ to $C_6$ alkoxy, and $C_1$ to $C_6$ alkoxy-($C_1$ to $C_6$ alkyl), wherein one of the pairs of $R^1$, $R^{1'}$ and $R^2$, $R^{2'}$ may form a carbocycle or heterocycle of 3 to 6 constituent ring members wherein the heterocycle may comprise from 1 to 3 constituent heteroatom ring members selected from oxygen and nitrogen which nitrogen may be substituted by $C_1$ to $C_6$ alkyl; and wherein at least one of $R^1$, $R^{1'}$, $R^2$, and $R^{2'}$ is other than hydrogen;

s is an integer from 0 to 6;

q is 0 or 1;

$R^5$ is hydrogen or methyl;

Z is selected from the group consisting of:

—$(CH_2)_m$— wherein m is from 1 to 10;

—$(CH_2)_n$—CH═CH— wherein n is from 1 to 6;

—$(CH_2)_p$-$A^1$-$CH_2$— wherein $A^1$ is oxygen or sulfur and p is 1 to 4; and ring 1, wherein ring 1 is selected from optionally substituted, aromatic or non-aromatic, carbocyclic and heterocyclic rings;

------ represents a double or single bond;

$Y^2$ is selected from —$CH_2$—, oxygen, or sulfur; and ring 2 is selected from optionally substituted, aromatic or non-aromatic, carbocyclic and heterocyclic rings.

23. The drug-polymer conjugate of claim 1, wherein the bicyclic prostaglandin D is selected from the following formulae and forms an ester with linker group L and is the carboxylic acid (C═O) residue of the ester:

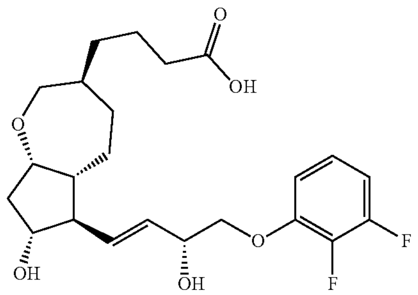

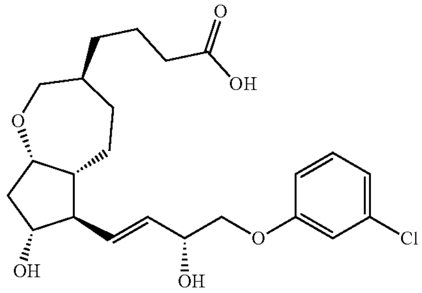

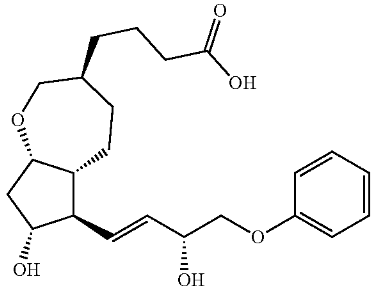

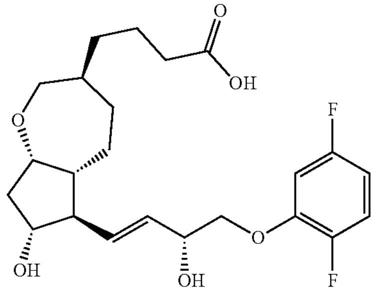

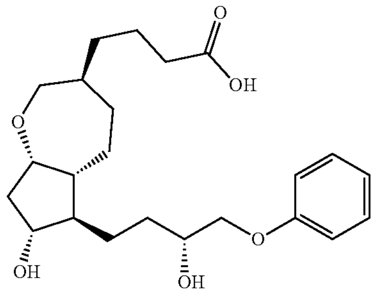

-continued
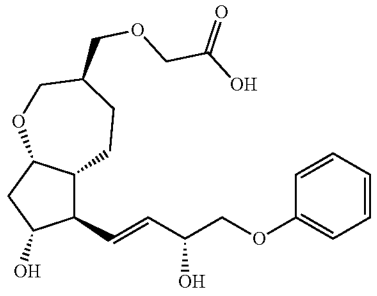
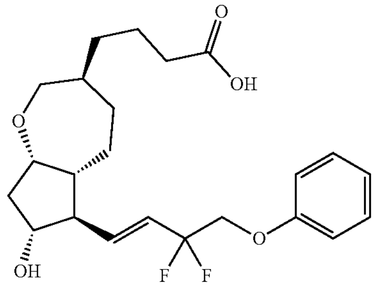
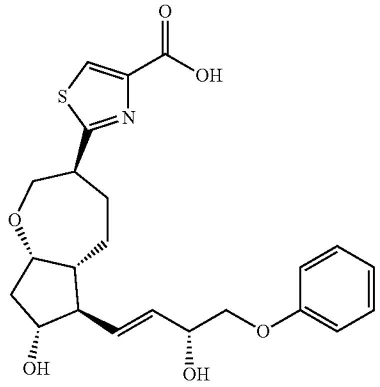
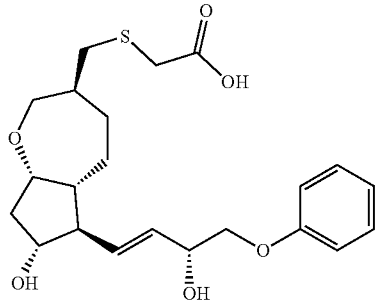
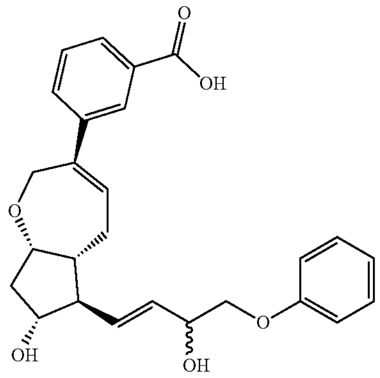
-continued
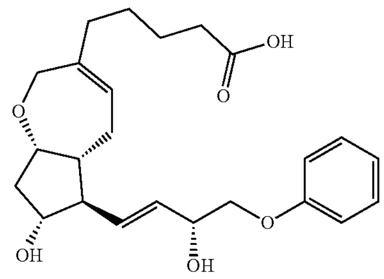
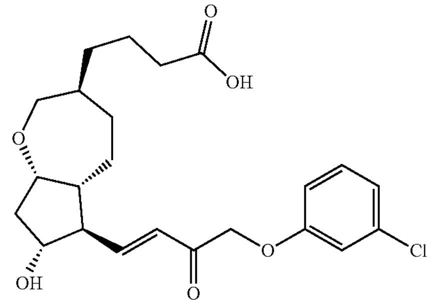
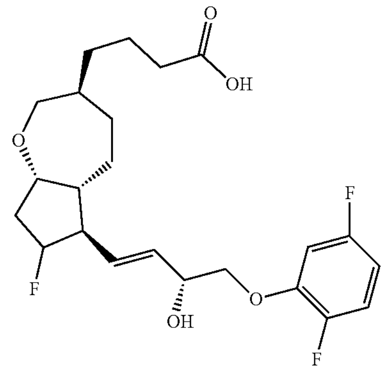
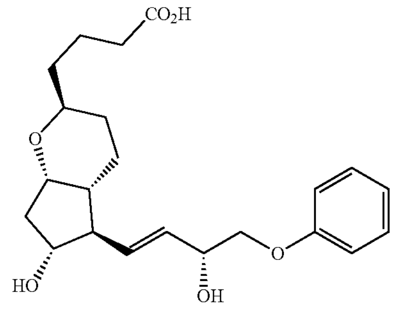
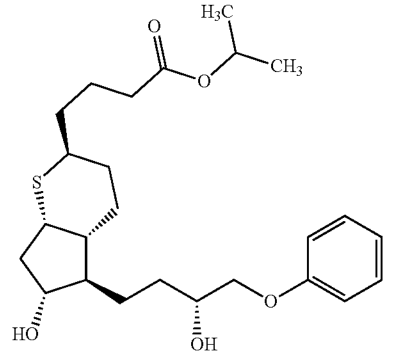

-continued

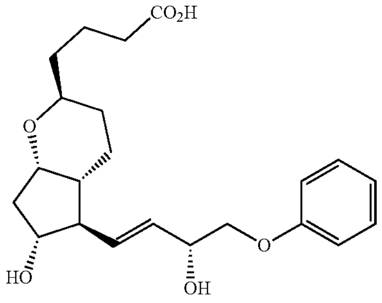

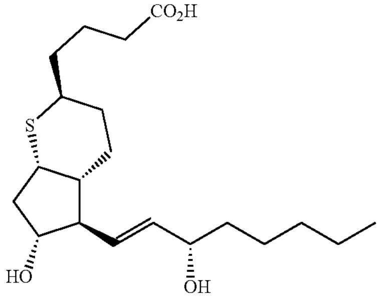

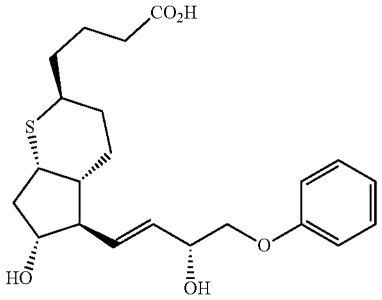

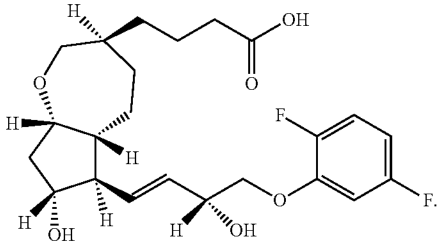

24. The drug polymer conjugate of claim 1, which is a copolymer of:

(i) at least one monomer of formula (I) selected from the group consisting of:

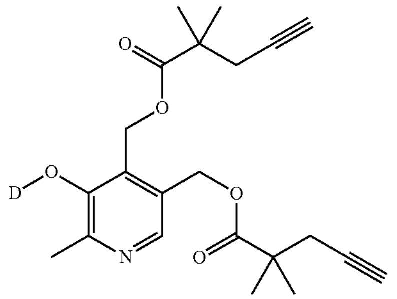
;

-continued

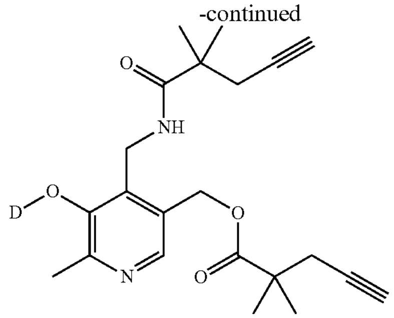
;

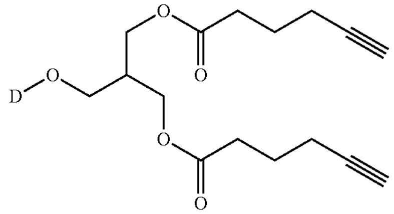
;

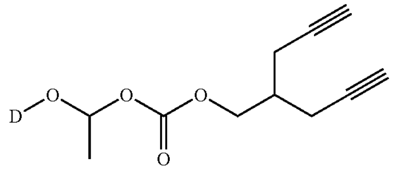
; and

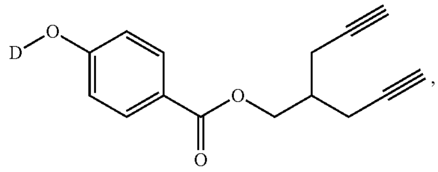
, wherein D is of formula:

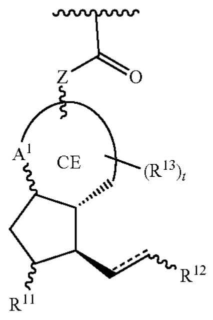

wherein

CE is a 6 or 7 membered cyclic ether or cyclic thioether which may be saturated or include one double bond;

$A^1$ is oxygen or sulfur;

$\overline{\overline{\quad}}$ represents a double or single bond which is independently selected in each case;

$R^{11}$ or $R^{12}$ is linked to the polymer backbone, wherein:

$R^{11}$ and $R^{12}$ when linked to the polymer backbone comprise the alcohol residue of an ester or carbonate linking group;

$R^{11}$ when not linked to the polymer backbone is hydroxyl or halo;

$R^{12}$ when not linked to the polymer backbone is $C_{1-6}$ alkyl optionally substituted with 1 to 5 substituents selected from the group consisting of hydroxyl, oxo, halo, $C_{1-4}$ alkoxy, ring 2, O-ring 2, and —S-ring 2, wherein ring 2 is selected from optionally substituted, aromatic or non-aromatic, carbocyclic and heterocyclic rings;

$R^{13}$ is selected from halo, $C_{1-4}$ alkyl, and $C_{1-4}$alkoxy;

tis 0, 1 or 2; and

Z is selected from the group consisting of:

- $—(CH_2)_m—$ wherein m is an integer from 1 to 10;
- $—(CH_2)_n—CH═CH—$ wherein n is an integer from 1 to 6;
- $—(CH_2)_p\text{-}A^1\text{-}CH_2—$ wherein $A^1$ is oxygen or sulfur and p is 1 to 4; and
- ring 1, wherein ring 1 is selected from optionally substituted, aromatic or non-aromatic, carbocyclic and heterocyclic rings;

(ii) at least one co-monomer of formula (III) selected from the group consisting of:

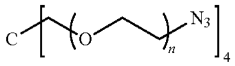
;

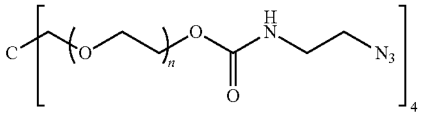
;

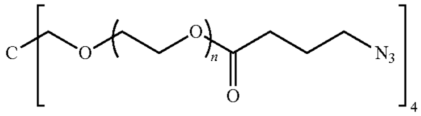
; and

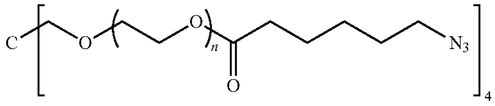
, wherein n is the number of ethyleneoxy groups and is an integer from 2 to 50.

25. The drug polymer conjugate of claim 1, which is a copolymer of:

(i) at least one monomer of formula (I) selected from the group consisting of:

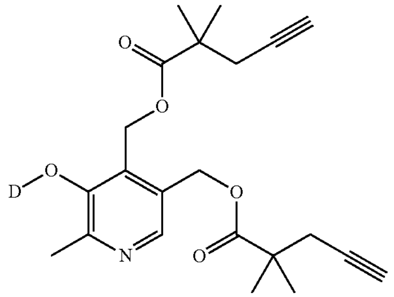
;

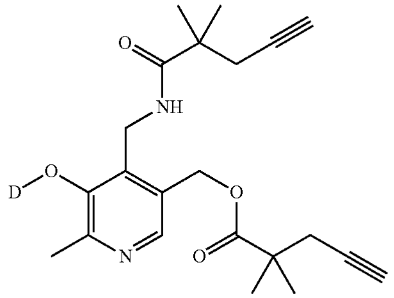
;

-continued

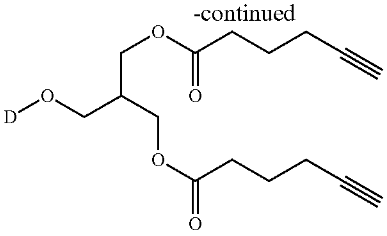
;

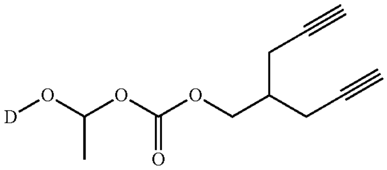
; and

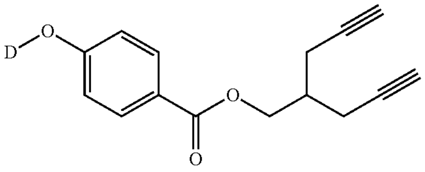
, wherein D is of formula:

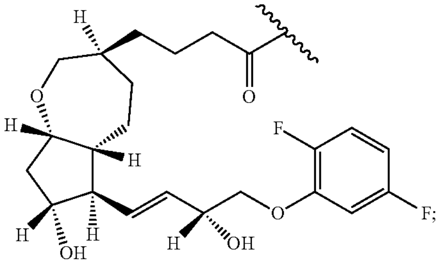
; and (ii) at least one co-monomer of formula (III) selected from the group consisting of;

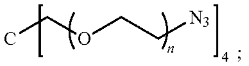
;

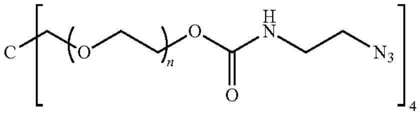
;

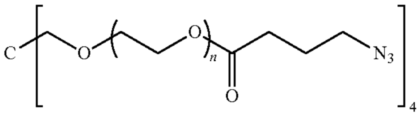
; and

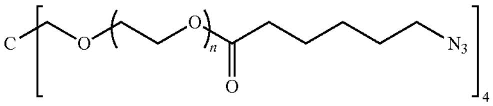
, wherein n is the number of ethyleneoxy groups and is an integer from 2 to 50.

26. An ocular implant comprising the drug polymer conjugate of claim 1.

* * * * *